United States Patent
Bisagni et al.

(10) Patent No.: US 12,162,816 B2
(45) Date of Patent: *Dec. 10, 2024

(54) METHOD OF REDUCING AROMATIC NITRO COMPOUNDS

(71) Applicant: Johnson Matthey Public Limited Company, London (GB)

(72) Inventors: Serena Bisagni, Cambridge (GB); Amin Bornadel, Cambridge (GB); Beatriz Dominguez, Cambridge (GB); Jacques Lepaih, Cambridge (GB); Ahir Pushpanath, Cambridge (GB); Iustina Slabu, Cambridge (GB); Jason Tedrow, Salem, MA (US); Steven Mennen, Boston, MA (US); Simon Hedley, West Boldon (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/296,440

(22) PCT Filed: Dec. 12, 2019

(86) PCT No.: PCT/GB2019/053518
§ 371 (c)(1),
(2) Date: May 24, 2021

(87) PCT Pub. No.: WO2020/128434
PCT Pub. Date: Jun. 25, 2020

(65) Prior Publication Data
US 2022/0017452 A1      Jan. 20, 2022

Related U.S. Application Data

(60) Provisional application No. 62/781,331, filed on Dec. 18, 2018.

(51) Int. Cl.
*C07C 209/36*       (2006.01)
*B01J 31/00*        (2006.01)

(52) U.S. Cl.
CPC ........... *C07C 209/36* (2013.01); *B01J 31/003* (2013.01)

(58) Field of Classification Search
CPC ............................. C07C 209/36; B01J 31/003
See application file for complete search history.

(56) References Cited

U.S. PATENT DOCUMENTS 5,777,190 A    7/1998  Shah et al.
6,096,924 A    8/2000  Studer et al.
2009/0297272 A1*  12/2009  Priester, III ............... B09C 1/10
                                                          252/372
2015/0045535 A1   2/2015  Berka
2022/0042055 A1*  2/2022  Bisagni ................ C12Y 106/99

FOREIGN PATENT DOCUMENTS

| CN | 103 642 861 A | 3/2014 | |
|---|---|---|---|
| JP | H11-505537 A | 5/1999 | |
| WO | WO1996036597 | * 11/1996 | ........... C07C 311/43 |
| WO | 2006/006961 A1 | 1/2006 | |
| WO | 2006/069610 A1 | 7/2006 | |
| WO | WO-2012008860 A2 | * 1/2012 | ............. A61K 38/44 |
| WO | 2015/048332 A2 | 4/2015 | |

OTHER PUBLICATIONS

Miller et al. Molecules, 2018, 23, 211.*
Berenguer-Murcia et al. Curr. Org. Chem. 14 (2010) 1000-1021, abstract provided.*
J. Park, Doctor of Philosophy Dissertation of Georgia Institute of Technology, (2014) (Year: 2014).*
B.Hall, et.al. 54(3) Antimicrobial Agents and Chemotherapy, 1193-1199(2010) (Year: 2010).*
Genbank: WP_003178951.1—Multispecies: NADPH-dependent oxidoreductase [Bacillus].
Orlandi, et al., "Recent Developments in the Reduction of Aromatic and Aliphatic Nitro Compounds to Amines", Organic process research & development, vol. 22, pp. 430-445, 2018.
Tran, et al., "Highly selective and controllable synthesis of arylhydroxylamines by the reduction of nitroarenes with an electron withdrawing group using a new nitroreductase BaNTR1", Chem Commun, vol. 50, pp. 2861-2864, 2014.
Database UniParc, 2004, N.N.: "Bacillus licheniformis (pp. 1-2)", XP002798056, Database accession No. UPI000043D088; See the sequence = SEQ ID No. 1 of the application.
Green, et al., "Investigating the promiscuity of the chloramphenicol nitroreductase from Haemophilus influenzae towards the reduction of 4-nitrobenzene derivatives", Bioorg Med Chem Lett., vol. 29(9), pp. 1127-1132, 2019.
Bisagni, et al., "From hit to process—examples of chiral amine synthesis from sma 11 to large seal e", 9th International Congress on Biocatalysis, Hamburg, Germany, Aug. 2018 Programme information, L5-3, 2018.
Zhang, et al., "Reduction of nitroarenes by magnetically recoverable nitroreductase immobilized on Fe3O4 nanoparticles", Scientific Reports, vol. 10, Article No. 2810, 2020.

* cited by examiner

*Primary Examiner* — Alexander R Pagano
*Assistant Examiner* — Frank S. Hou
(74) *Attorney, Agent, or Firm* — BakerHostetler

(57) ABSTRACT

Disclosed herein is a method of reducing an aromatic nitro compound. In some embodiments the method comprises the step of contacting an aromatic nitro compound with a catalyst, wherein, the catalyst comprises, a disproportionation agent, and a biocatalyst. Also disclosed is a biocatalyst for use in the method, use of a disproportionation agent, and a biocatalyst, as a catalyst for reducing an aromatic nitro compound, and a kit comprising a disproportionation agent, and a biocatalyst.

14 Claims, 14 Drawing Sheets

Specification includes a Sequence Listing.

METHOD OF REDUCING AROMATIC NITRO COMPOUNDS

JOINT RESEARCH AGREEMENT

The present disclosure was developed and the claimed invention was made by or on behalf of one or more parties to a joint research agreement. The joint research agreement was in effect on or before the date the present disclosure was made and the present disclosure was made as a result of activities undertaken within the scope of the joint research agreement. Johnson Matthey Public Limited Company and Amgen Inc. are parties to the joint research agreement.

FIELD OF THE INVENTION

The invention relates to a method for reducing a substrate using a catalyst comprising a disproportionation agent and a biocatalyst, the use of the catalyst for reducing a substrate, and kits comprising the catalyst. The invention also relates to a biocatalyst for use in the method.

BACKGROUND

The reduction of aromatic nitro compounds has attracted considerable interest as a quick and efficient method for the production of aromatic amine compounds, which are essential intermediates in the chemical, pharmaceutical and agrochemical industries. However, the reduction process is complex. The generally accepted mechanism is based on an electrochemical model, as shown Scheme 1. According to this model, two parallel chemical routes are responsible for the conversion of the nitro starting material to the amine product (Haber).

The main pathway involves the stepwise reduction of the nitro group 2 to the nitroso group 7, hydroxylamine 3 and finally the amine functional group 1. The three steps have different rates, with the reduction of hydroxylamine 3 as the slowest step. This leads to significant accumulation of the hydroxylamine 3 intermediate.

The parallel pathway involves a condensation route, in which an azoxy intermediate 6 is formed via condensation between the nitroso 7 and the hydroxylamine 3 intermediates. The azoxy intermediate 6 is reduced in a stepwise manner to the azo compound 4, hydrazo compound 5 and finally amine product 1.

The preferred industrial method for the reduction of aromatic nitro compounds to aromatic amine compounds is catalytic hydrogenation methods using hydrogen gas at high pressure with supported metal catalysts. Typical hydrogenation catalysts include Pd/C or Pd/Al$_2$O$_3$, (Hoogenraad at al.). Additionally, commercial formulations of Ni (Gallagher et al.), supported nanoparticles such as Au/TiO$_2$ and Au/Fe$_2$O$_3$ (Corma and Serna), or commercially available sulfided Pt catalysts (Kasparian et al.; Boymans et al.) are known. Catalytic transfer hydrogenation methods circumvent the need for specialised equipment for handling hydrogen gas at high pressures by in situ generation of hydrogen gas using NaBH$_4$, hydrazine hydrate or formic acid (Kadam et al.).

An improved catalytic hydrogenation method was developed by Studer et al. (Studer et al.; Studer and Baumeister), in which a catalytic quantity of a vanadium compound is used in combination with a noble metal, nickel or cobalt hydrogenation catalyst. The vanadium compound is thought to promote the disproportionation of hydroxylamine 3 to aniline 1 and nitroso 7.

However, the presence of residual metal contamination in both the product and organic waste stream is a major concern for catalytic chemical reduction methods.

Residual metal contamination can be prevented by the development of metal-free reduction strategies. However, these methods usually suffer from long reaction times and employ high temperatures (Orlandi et al.).

An alternative method for the reduction of aromatic nitro compounds to aromatic amine compounds is the use of flavin-dependent nitroreductases (NRs). Flavin-dependent nitroreductases (NRs) are enzymes able to reduce a broad range of aromatic nitro compounds, exploiting the versatility of flavin cofactors, such as flavin mononucleotide (FMN), flavin adenine dinucleotide (FAD) or other flavins. To a certain extent, bacterial enoate reductases that share the same flavin cofactor with nitroreductases, are also able to reduce the aromatic nitro group (Toogood and Scrutton; Williams and Bruce).

However, previous attempts at reducing aromatic nitro compounds using nitroreductases have resulted in only moderate success, with complete conversion to the desired amine still eluding researchers (Hoogenraad at al.; Pitsawong et al.; Yanto et al.). Generally, nitroreductases are only able to catalyse the reduction of aromatic nitro com- Scheme 1: Two parallel routes for the conversion of aromatic nitro compounds to aromatic amine compounds

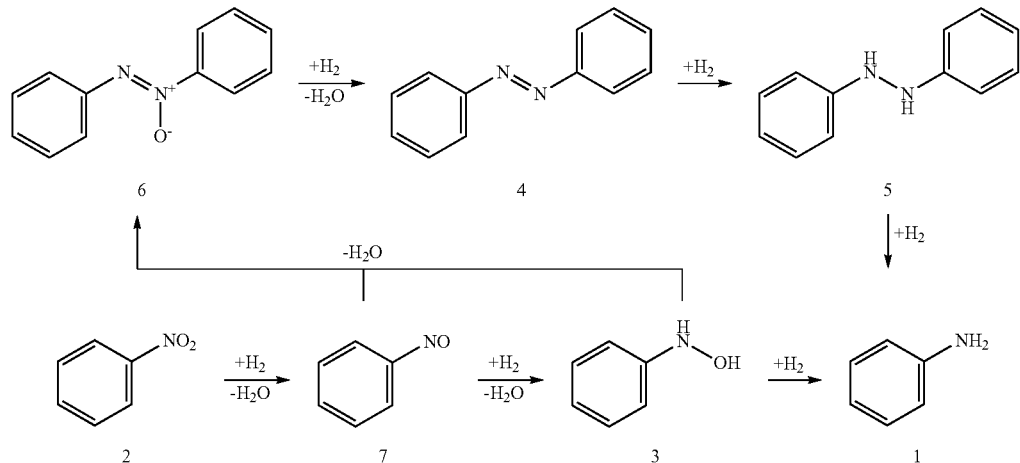

pounds 2 to the corresponding hydroxylamines 3. In addition, these reactive intermediates accumulate and form a series of side-products, lowering the efficiency of the biocatalytic process. In very rare cases, the reduction is taken forward to the aromatic amine 1, however this is highly dependent on the particular substrate involved (Miller et al.).

Accordingly, the reduction of aromatic nitro compounds still presents significant challenges regarding the efficient control of the degree of hydrogenation, as well as the selective hydrogenation of the nitro group in presence of other functional groups.

SUMMARY OF THE INVENTION

The present inventors have developed a catalytic method for the reduction of an aromatic nitro compound, in which the hydroxylamine generated following a biocatalytic nitroreduction rapidly enters a disproportionation cycle catalysed by a disproportionation agent, resulting in accumulation of the final aromatic amine product. This method has been demonstrated with a range of substrates and intensification (scale-up) of the reaction has also been demonstrated.

In a first aspect of the invention, there is provided a method of reducing an aromatic nitro compound comprising the step of:

(i) contacting an aromatic nitro compound with a catalyst, wherein, the catalyst comprises:
 (a) a disproportionation agent; and
 (b) a biocatalyst.

The disproportionation agent may comprise a metal, specifically a metal selected from the groups 3 to 13, and more preferably a transition metal selected from the groups 3 to 12. The disproportionation agent may comprise a metal selected from groups 5 to 11, preferably group 5.

The disproportionation agent may comprise a metal selected from vanadium, chromium, molybdenum, iron, cobalt, nickel or copper; preferably selected from vanadium, molybdenum, iron, cobalt or copper; more preferably vanadium.

The disproportionation agent may be selected from $CuCl_2$, $Cu(OAc)_2$, $Cu_2O$, $Cu(0)$ (copper metal), $FeCl_2$, $FeCl_3$, $Fe(acac)_3$, $FeCl_2$, $FeSO_4$, $Fe(0)$ (iron metal), $NaMoO_4$, $NH_4VO_3$, $VOSO_4$, $V(acac)_3$, $V_2O_5$, $V(0)$ (vanadium metal) and $CoCl_2$. Preferably, the disproportionation agent is selected from $CuCl_2$, $FeCl_2$, $NaMoO_4$, $NH_4VO_3$, $VOSO_4$, $V(acac)_3$, $V_2O_5$ and $CoCl_2$. More preferably, the disproportionation agent is selected from $NH_4VO_3$, $VOSO_4$ and $V_2O_5$.

The biocatalyst may be or comprise a polypeptide capable of catalysing the reduction of an aromatic nitro compound to an aromatic hydroxylamine compound. Optionally, the biocatalyst is or comprises a polypeptide capable of catalysing the reduction of an aromatic nitro compound to an aromatic amine compound.

The biocatalyst may be an oxidoreductase. Preferably, the biocatalyst is a nitroreductase.

The biocatalyst may be or comprise a polypeptide belonging to GO:0016491. Preferably, the biocatalyst is or comprises a polypeptide belonging to GO:0016657.

The biocatalyst may be or comprise a polypeptide belonging to EC 1.X.X.X, wherein X denotes any subfamily. Optionally, the biocatalyst is or comprises a polypeptide belonging to EC 1.5.1.X, 1.6.99.X or EC 1.3.1.X, where X denotes any subclass.

The biocatalyst may be or comprise a polypeptide belonging to CATH superfamily 3.40.109.10, 3.20.20.70 or 3.40.50.360.

The biocatalyst may be or comprise a polypeptide belonging to PF00724, PF00881 or PF02525. Preferably, the biocatalyst is or comprises a polypeptide belonging to PF00881.

The biocatalyst may be or comprise a polypeptide having the following sequence motif (1):

(1)    A-x(3,4)-G-x-[ADEGQST]-x(4)-[ADEGNQST]-
       [AEGNQST]

wherein:
x denotes any amino acid residue,
x(n) denotes a segment consisting of any amino acid residues of length n;
[ab] denotes a single residue selected from a or b; and amino acids are denoted by their single letter codes.

The biocatalyst may be or comprise a polypeptide having at least 9 amino acid residues similar or identical to those of SEQ ID NO:1 [NR-4] at the positions corresponding to:
 15, 39, 40, 41, 42, 64, 65, 67, 112, 132, 135, 136, 138, 220, 224, 229, 230 of SEQ ID NO:1 [NR-4].

The biocatalyst may be or comprise a polypeptide having at least 15 amino acid residues similar or identical to those of SEQ ID NO:1 [NR-4] at the positions corresponding to:
 13, 15, 38, 39, 40, 41, 42, 43, 64, 65, 67, 69, 104, 112, 132, 133, 134, 135, 136, 137, 138, 139, 172, 220, 221, 224, 225, 229, 230, 233.
of SEQ ID NO:1 [NR-4].

The biocatalyst may be or comprise a polypeptide having at least 50% similarity or identity to SEQ ID NO:1 [NR-4] and having the following amino acids at the residues corresponding to the following positions in SEQ ID NO:1 [NR-4]:

| Position | Residues |
|---|---|
| 41 | [SIMVAHNTWL]; |
| 136 | [GSAN]; |
| 224 | [KATYFREGIQV]; |
| 229 | [SKRYAQCGHNTV]; |
| 230 | [RKYE], | wherein:
[ab] denotes a single residue selected from a or b; and amino acids are denoted by their single letter codes.

The biocatalyst may be or comprise a polypeptide having at least 70% sequence identity to SEQ ID NO:1 [NR-4], 2 [NR-14], 3 [NR-17] or 4 [NR-24].

The method may be a method of reducing an aromatic nitro compound to produce an aromatic hydroxylamine compound.

The method may be a method of reducing an aromatic nitro compound to produce an aromatic amine compound.

The method may further comprise the step of isolating the product.

The method may further comprise the step of isolating the catalyst.

The method may further comprise the step of contacting the biocatalyst with a co-substrate.

The co-substrate may be a cofactor and the method may further comprise the step of regenerating the cofactor using a reduced cofactor regenerating system.

The step of contacting the aromatic nitro compound with the catalyst may comprise adding discreet portions of the aromatic nitro compound to the catalyst.

The step of contact the aromatic nitro compound with the catalyst may comprise continuously adding the aromatic nitro compound to the catalyst.

The temperature may be maintained in the range 0 to 100° C., preferably 10 to 80° C., more preferably 20 to 45° C., even more preferably 20 to 35° C.

The pH may be maintained in the range 3.0 to 10.0, preferably 5.0 to 9.0, more preferably 6.5 to 8.0.

In a further aspect of the invention, there is provided the use of:
(a) a disproportionation agent; and
(b) a biocatalyst
as a catalyst for reducing an aromatic nitro compound.

In a further aspect of the invention, there is provided a kit comprising:
(a) a disproportionation agent; and
(b) a biocatalyst.

In a further aspect of the invention, there is provided a biocatalyst for use in the method, wherein the biocatalyst is or comprises a polypeptide having at least 70% similarity or identity to SEQ ID NO:1 [NR-4] and having the following amino acids at the residues corresponding to the following positions of SEQ ID NO:1 [NR-4]:

| | |
|---|---|
| 41 | [SMVAHNTWL]; |
| 136 | [SAN]; |
| 224 | [KTYFREGIQV]; |
| 229 | [SKRYAQCGHNT]; |
| 230 | [RYE], | wherein:
[ab] denotes a single residue selected from a or b; and amino acids are denoted by their single letter codes.
These and other aspects are described in detail below.

SUMMARY OF THE SEQUENCES

Figure 1A:
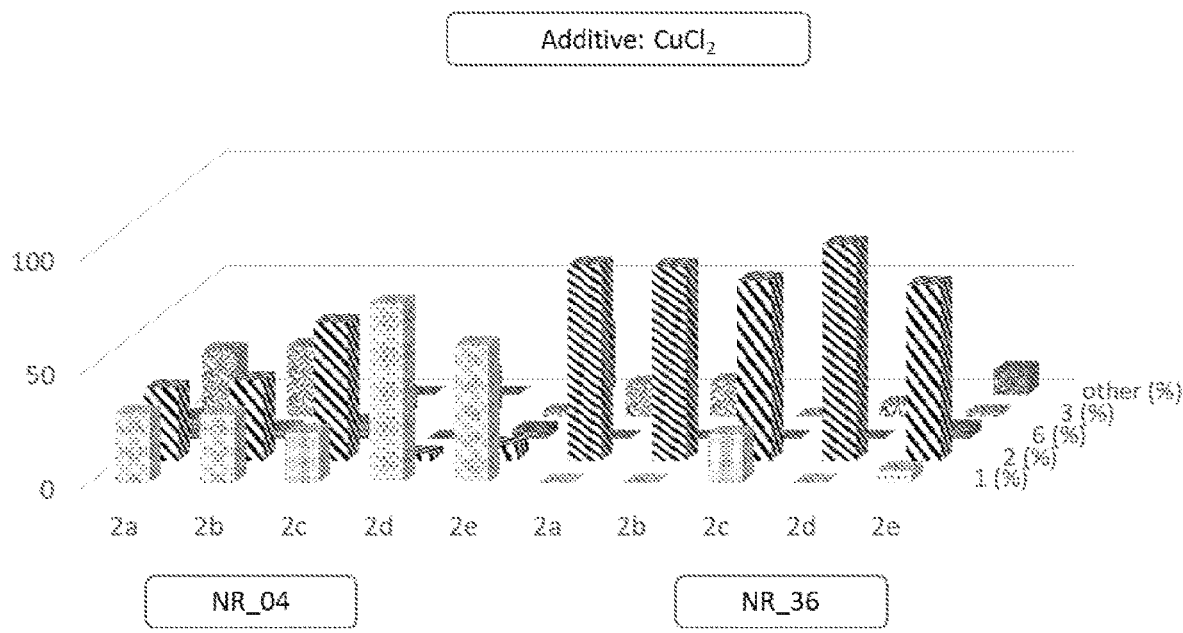
FIGS. 1A-E show percentage conversion of nitro substrates 2a-e to amine products 1a-e along with azoxy (6a-e) and hydroxylamine (3a-e) by-products using a catalyst comprising a nitroreductase (NR-4 or NR-36) and a disproportionation agent: (A) $CuCl_2$; (B) $FeCl_2$; (C) $NaMoO_4$; (D) $V_2O_5$ and (E) $CoCl_2$.

The methods of the present invention are described herein with reference to the sequence identification numbers listed below. The sequences are disclosed in the sequence listing.
SEQ ID NO:1 Nitroreductase amino acid sequence (NR-4)
SEQ ID NO:2 Nitroreductase amino acid sequence (NR-14)
SEQ ID NO:3 Nitroreductase amino acid sequence (NR-17)
SEQ ID NO:4 Nitroreductase amino acid sequence (NR-20)
SEQ ID NO:5 Nitroreductase amino acid sequence (NR-23)
SEQ ID NO:6 Nitroreductase amino acid sequence (NR-24)
SEQ ID NO:7 Nitroreductase amino acid sequence (NR-31)
SEQ ID NO:8 Nitroreductase amino acid sequence (NR-36)
SEQ ID NO:9 Nitroreductase amino acid sequence (NR—I-A5)
SEQ ID NO: 10 Nitroreductase amino acid sequence (NR—I-A11)
SEQ ID NO:11 Nitroreductase amino acid sequence (NR—I-A12)
SEQ ID NO: 12 Nitroreductase amino acid sequence (NR-I-C3)
SEQ ID NO: 13 Nitroreductase amino acid sequence (NR—I-D6)
SEQ ID NO: 14 Nitroreductase amino acid sequence (NR—I-E7)
SEQ ID NO:15 Nitroreductase amino acid sequence (NR-I-F5)
SEQ ID NO:16 Nitroreductase amino acid sequence (NR-I-H5)
SEQ ID NO:17 Nitroreductase amino acid sequence (NR-II-A1)
SEQ ID NO: 18 Nitroreductase amino acid sequence (NR-II-B10)
SEQ ID NO:19 Nitroreductase amino acid sequence (NR-II-D4)

SEQ ID NO:20 Nitroreductase amino acid sequence (NR-II-D11)
SEQ ID NO:21 Nitroreductase amino acid sequence (NR-II-D12)
SEQ ID NO:22 Nitroreductase amino acid sequence (NR-II-E1)
SEQ ID NO:23 ENE-reductase amino acid sequence (ENE-101)

DETAILED DESCRIPTION OF THE INVENTION

The present invention provides a method of reducing an aromatic nitro compound, the method comprising the step of contacting an aromatic nitro compound with a catalyst to provide a product. As described in further detail below, the catalyst comprises a disproportionation agent and a biocatalyst. The method allows for the production of a product in high yield, for example greater than 90% conversion. The method allows the reduction of a range of aromatic nitro compounds and can be performed at large scale. Moreover, the method can be performed at ambient temperature and pressure, without the need for hydrogen gas.

Disproportionation Agent

The catalyst comprises a disproportionation agent. Disproportionation agents are capable of promoting the reaction of a starting compound having an intermediate oxidation state to two different product compounds, one having a higher oxidation state than the starting compound and one having a lower oxidation state than the starting compound.

The activity of a disproportionation agent can be measured using routine methods, for example, by chromatography or nuclear magnetic resonance (NMR).

The disproportionation agent promotes the disproportionation of a hydroxylamine intermediate to a nitroso intermediate and an amine compound. The disproportionation agent may also promote the disproportionation of a hydrazo intermediate to an azo compound and one or more amine compounds.

The disproportionation agent comprises a metal additive. That is, the disproportionation agent comprises a metal selected from groups 3 to 13 in the periodic table. As such, the disproportionation agent does not comprise boron. Preferably, the disproportionation agent comprises a transition metal additive. That is, the disproportionation agent comprises a transition metal selected from the groups 3 to 12 of the periodic table.

More preferably, the disproportionation agent comprises a metal selected from groups 5 to 11 of the periodic table, even more preferably group 5 of the periodic table.

The disproportionation agent may comprise a metal selected from vanadium, chromium, molybdenum, iron, cobalt, nickel or copper. Preferably, the disproportionation agent comprises a metal selected from vanadium, molybdenum, iron, cobalt or copper. More preferably, the disproportionation agent comprises vanadium.

The disproportionation agent may comprise a metal having an oxidation state of from 0 to VI. Preferably, the disproportionation agent comprises a metal having an oxidation state of from II to V, more preferably IV or V.

The disproportionation agent may comprise a metal having more than one accessible oxidation states. The disproportionation agent may comprise a metal having accessible oxidation states separated by zero, one or two oxidation levels. For example, the disproportionation agent may comprise a metal having the accessible oxidation states 0 and II, I and III, or IV and V.

The disproportionation agent may comprise a counterion. The counterion may be any counterion suitable for stabilising the oxidation state of the metal in the disproportionation agent.

Typically the counterion is negatively charged. That is, typically the counterion is an anion. Typical examples of anions include inorganic anions such as halo, oxo, borate, aluminate, nitrate, phosphate, sulphate and hypochlorite. Typical examples of anions also include organic anions such as formate, carboxylate and acetate acetylacetonate.

Examples of halo anions include fluorate, chlorate, bromate and iodate.

Examples of borate anions include tertrahydroxyborate and tetrafluoroborate

Examples of phosphate anions include phosphate $(PO_4)^{3-}$ and hexafluorophosphate.

Alternatively, the counterion is positively charged. That is, the counterion is a cation. Typical examples of cations include inorganic cations such as alkali metals, alkali earth metals, phosphonium and ammonium.

Examples of alkali metal cations include lithium, sodium, potassium and caesium.

Examples of alkali earth metal cations include magnesium and calcium.

Examples of phosphonium cations include tetraphenylphosphonium.

Examples of ammonium cations include ammonium $(NH_4)^+$, tetramethylammonium and tetrabutylammonium.

The disproportionation agent may comprise water. That is, the disproportionation agent may be a hydrate.

The disproportionation agent may comprise one or more ligands. Typical ligands include EDTA, dipicolinic acid, imidazole, histidine, iminodiacetic acid, triethylenetriamine, methylaminoethanol, proline, N-(2-hydroxybenzoyl) pyrrolidine and dipivaloylmethane.

Typical disproportionation agents include $CuCl_2$, $Cu(OAc)_2$, $Cu_2O$, $Cu(0)$ (copper metal), $FeCl_2$, $FeCl_3$, $Fe(acac)_3$, $FeCl_2$, $FeSO_4$, $Fe(0)$ (iron metal), $NaMoO_4$, $NH_4VO_3$, $VOSO_4$, $V(acac)_3$, $V_2O_5$, $V(0)$ (vanadium metal) or $CoCl_2$. Preferably, the disproportionation agent is selected from $CuCl_2$, $FeCl_2$, $NaMoO_4$, $NH_4VO_3$, $VOSO_4$, $V(acac)_3$, $V_2O_5$ or $CoCl_2$.

In one embodiment, the disproportionation agent is selected from $V_2O_5$, $VO_2$, $NH_4VO_3$, $VOSO_4$, $VO(NO_3)_3$, $V(acac)_3$, $VOX_3$, $VX_4$, $VX_3$ or $VX_2$, wherein X is F, Cl or Br. Preferably, the disproportionation agent is selected from $NH_4VO_3$, $VOSO_4$ and $V_2O_5$.

The inventors have observed that V(III) and V(IV) disproportionation agents such as $VOSO_4$ have higher water solubility than V(V) disproportionation agents such as $NH_4VO_3$ and $V_2O_5$. However, V(V) disproportionation agents such as $NH_4VO_3$ and $V_2O_5$ have lower toxicity than V(III) and V(IV) disproportionation agents.

Biocatalyst—Function

The catalyst comprises a biocatalyst. That is, the catalyst comprises a polypeptide having enzymatic activity.

Typically, the biocatalyst is a nitroreductase. That is, the biocatalyst is or comprises a polypeptide having nitroreductase activity. The biocatalyst may comprise a polypeptide or variant polypeptide as defined herein having nitroreductase activity.

Polypeptides having nitroreductase activity are capable of catalysing the reduction of an aromatic nitro group to an aromatic hydroxylamine group, for example, catalysing the reduction of 2 to 3 in Scheme 1. Polypeptides having nitroreductase activity may also be capable of catalysing the reduction of an aromatic nitro group to an aromatic amine group, for example, catalysing the reduction of 2 to 1 in Scheme 1.

Nitroreductase activity can be determined by measuring the reduction of an aromatic nitro compound to an aromatic hydroxylamine compound. This can be done using routine methods, for example, by monitoring absorption at 205 nm (which measures adsorption by the aromatic group), 340 nm (which measures adsorption by NAD(P)H), or by a colorimetric assay (e.g. the INT dye assay described herein).

For example, a polypeptide having nitroreductase activity is capable of catalysing the reduction of 3-nitrostyrene (1-ethenyl-3-nitrobenzene) to 3-vinylaniline (3-ethenylaniline) in greater than 30% yield under the following reaction conditions: 375 µL of buffer 250 mM potassium phosphate (pH 6.0; 7.0 or 8.0)+1 mM NADP$^+$ and 1 mM NAD$^+$, 100 mM D-glucose, 1 mg/mL GDH+5 mg/mL polypeptide+25 µL 3-nitrostyrene solution (0.4 M in MTBE, final concentration of substrate 20 mM) at 35° C. for 18 hours.

Polypeptides having nitroreductase activity may be classified using the gene ontology database maintained by the Gene Ontology Consortium (http://www.geneontology.org/). Polypeptides having nitroreductase activity are oxidoreductases and are members of GO:0016491 and may be further classified as members of GO:0016657 (e.g. GO version 20181108 of November 2018). GO:0016657 may define enzymes capable of catalysing an oxidation-reduction (redox) reaction in which NADH or NADPH acts as a hydrogen or electron donor and reduces a nitrogenous group.

Polypeptides having nitroreductase activity may be classified using Enzyme Commission numbers maintained by the International Union of Biochemistry and Molecular Biology (http://www.sbcs.qmul.ac.uk/iubmb/enzyme/). Polypeptides having nitroreductase activity may be members of EC 1 (oxidoreductases). Polypeptides having nitroreductase activity may be further classified into separate detailed EC numbers including 1.5.1.X (oxidoreductases acting on the CH—NH group of donors with NAD or NADP as the acceptor) and 1.6.99.X (oxidoreductases acting on NADH or NADPH with other acceptors). Furthermore, polypeptides having nitroreductase activity may belong E.C 1.3.1.X (oxidoreductases acting on CH—CH group donors with NAD or NADP as acceptor) as a promiscuous side activity of these enzymes.

Biocatalyst—Structure

The biocatalyst may be classified using the CATH protein structure classification database maintained by the Orengo group at University College London (http://www.cathdb.info/). The biocatalyst may comprise a polypeptide having a structure classified as belonging to the CATH superfamily 3.40.109.10, 3.20.20.70 or 3.40.50.360 (e.g. CATH-Plus 4.2.0 released May 2017). Preferably the biocatalyst is a polypeptide belonging to 3.40.109.10 (CATH-Plus 4.2.0).

The biocatalyst may be classified using the protein family database (Pfam) maintained by the European Bioinformatics Institute (https://pfam.xfam.org/). The biocatalyst may comprise a polypeptide having a structure classified as belonging to PF00724 (old yellow enzyme structural family), PF00881 (nitroreductase family) or PF02525 (flavodoxin-like fold family) (e.g. Pfam version 31.0 released March 2017). Preferably the biocatalyst is a polypeptide belonging to PF00881 (version 31.0).

Biocatalyst—Motif Sequence

The biocatalyst may comprise a polypeptide belonging to PF00881 and having a characteristic motif (1):

(1)   A-x(3,4)-G-x-[ADEGQST]-x(4)-[ADEGNQST]-
      [AEGNQST]

where: x denotes any amino acid residue, x(n) denotes a segment consisting of any amino acid residues of length n (the residues may be the same as or different from each other); [ab] denotes a single residue selected from a or b; and amino acids are denoted by their single letter codes. This means that the polypeptide comprises a motif of 13 or 14 amino acids which are, in the following order: (position 1) alanine; (positions 2-4/5) three or four residues of any amino acids; (position 5/6) glycine; (position 6/7) one residue of any amino acid; (position 7/8) one residue which is any one of: alanine, aspartate, glutamate, glycine, glutamine, serine, threonine; (positions 8/9-11/12) four residues of any amino acids; (positions 12/13) one residue which is any one of: alanine, aspartate, glutamate, glycine, asparagine, glutamine, serine, threonine; and (positions 13/14) one residue which is any one of: alanine glutamate, glycine, asparagine, glutamine, serine, threonine.

Motif (1) identifies a flavin cofactor binding domain of a polypeptide belonging to PF00881. Polypeptides comprising motif (1) are capable of binding a flavin cofactor, such as an FMN cofactor.

Polypeptides comprising motif (1) may be identified using the PROSITE scanning tool (https://prosite.expasy.org). By scanning within the UniProt database (https://www.uniprot.org/) for polypeptides having motif (1), potential nitroreductases can be identified. Nitroreductase activity can be confirmed using routine methods, such as those summarised above.

The biocatalyst may comprise a polypeptide belonging to PF00881, having motif (1) and having nitroreductase activity.

Biocatalyst—Active Site Sequence

Seventeen amino acid residues defining an active site region of NR-4 were identified by their proximity to a substrate using structural modelling. These are amino acid residues 15, 39, 40, 41, 42, 64, 65, 67, 112, 132, 135, 136, 138, 220, 224, 229, 230 of SEQ ID NO:1 [NR-4].

The biocatalyst may comprise a polypeptide having amino acid residues that are identical or similar to the seventeen amino acid residues of the active site region of NR-4. Thus, the biocatalyst may comprise a polypeptide having amino acid residues similar or identical to those of SEQ ID NO:1 [NR-4] at the positions corresponding to residue 15, 39, 40, 41, 42, 64, 65, 67, 112, 132, 135, 136, 138, 220, 224, 229, 230 of SEQ ID NO:1 [NR-4]. The biocatalyst may comprise a polypeptide having at least 9 amino acid residues similar or identical to those of NR-4 at the positions corresponding to the 17 amino acid residues of the active site region of NR-4. That is, the nitroreductase may comprise a polypeptide having amino acid residues at least 50% similar or identical to those of NR-4 at the positions corresponding to the 17 amino acid residues of the active site region of NR-4. The biocatalyst may comprise a polypeptide having at least 9, 10, 11, 12, 13, 15, 14, 15, 16 or 17 amino acid residues similar or identical to those of NR-4 at the positions corresponding to the 17 amino acid residues of the active site region of NR-4.

The biocatalyst may be a polypeptide belonging to PF00881, having amino acid residues identical or similar to the active site region of NR-4 and having nitroreductase activity.

Thirty amino acid residues defining an extended active site region of NR-4 were identified by their proximity to a substrate using structural modelling. These are amino acid residues 13, 15, 38, 39, 40, 41, 42, 43, 64, 65, 67, 69, 104, 112, 132, 133, 134, 135, 136, 137, 138, 139, 172, 220, 221, 224, 225, 229, 230, 233 of SEQ ID NO:1 [NR-4].

The biocatalyst may comprise a polypeptide having amino acid residues that are identical or similar to the thirty amino acid residues of the extended active site region of NR-4. Thus, the biocatalyst may comprise a polypeptide having amino acid residues similar or identical to those of SEQ ID NO:1 [NR-4] at the positions corresponding to amino acid residue 13, 15, 38, 39, 40, 41, 42, 43, 64, 65, 67, 69, 104, 112, 132, 133, 134, 135, 136, 137, 138, 139, 172, 220, 221, 224, 225, 229, 230, 233 of SEQ ID NO:1 [NR-4]. The biocatalyst may comprise a polypeptide having at least 15 amino acid residues similar or identical to those of NR-4 at the positions corresponding to the 30 amino acid residues of the extended active site region of NR-4. That is, the nitroreductase may comprise a polypeptide having amino acid residues at least 50% similar or identical to those of NR-4 at the positions corresponding to the 30 amino acid residues of the extended active site region of NR-4. The biocatalyst may comprise a polypeptide having at least 15, 16, 17, 18, 19, 20, 21, 22, 23, 24, 25, 26, 27, 28, 29 or 30 amino acid residues similar or identical to those of NR-4 at the positions corresponding to the 30 amino acid residues of the extended active site region of NR-4.

The biocatalyst may comprise a polypeptide belonging to PF00881, having amino acid residues identical or similar to the extended active site region of NR-4 and having nitroreductase activity.

Five amino acid residues defining a conserved active site region of NR-4 were identified by their proximity to a substrate using structural modelling. These are amino acid residues 41, 136, 224, 229, 230 of SEQ ID NO:1 [NR-4].

The biocatalyst may comprise a polypeptide having at least 70% similarity or identity to SEQ ID NO: 1 [NR-4] and having the following amino acid residues at the at the following positions corresponding to conserved active site residues of SEQ ID NO:1 [NR-4]:

```
41     [SIMVAHNTWL];
136    [GSAN];
224    [KATYFREGIQV];
229    [SKRYAQCGHNTV];
230    [RKYE],
```

Where [ab] denotes a single residue selected from a or b; and amino acids are denoted by their single letter codes. This means that the polypeptide comprises, in the following order: (position 41) one residue which is any one of: serine, isoleucine, methionine, valine, alanine, histidine, asparagine, threonine, tryptophan, leucine; (position 136) one residue which is any one of: glycine, serine, alanine, asparagine; (position 224) one residue which is any one of: lysine, alanine, threonine, tyrosine, phenylalanine, arginine, glutamic acid, glycine, isoleucine, glutamine, valine; (position 229) one residue which is any one of: serine, lysine, arginine, tyrosine, alanine, glutamine, cysteine, glycine, histidine, asparagine, threonine, valine; and (position 230) one residue which is any one of: arginine, lysine, tyrosine, glutamic acid.

The biocatalysts may comprise a polypeptide having at least 80%, 85%, 90% or 95% similarity or identity to SEQ ID NO:1 [NR-4] and having the above amino acid residues at the five positions corresponding to the conserved active site region of SEQ ID NO:1 [NR-4].

The biocatalysts may comprise a polypeptide having at least 70% similarity or identity to SEQ ID NO: 1 [NR-4], having the above amino acid residues at the five positions corresponding to the conserved active site region of SEQ ID NO:1 [NR-4] and having nitroreductase activity.

Preferred biocatalysts comprise a polypeptide having at least 70% similarity or identity to SEQ ID NO:1 [NR-4], and having the amino acid residues at the five positions corresponding to the conserved active site region of SEQ ID NO:1 [NR-4] as set out in Table 1:

TABLE 1

Preferred biocatalysts

| SEQ ID NO | position in SEQ ID NO: 1 [NR-4] | | | | |
|---|---|---|---|---|---|
| | 41 | 136 | 224 | 229 | 320 |
| 1 [NR-4] | I | A | Y | Y | Y |
| 9 [NR-I-A5] | I | A | Y | Y | E |
| 10 [NR-I-A11] | T | A | Y | Y | Y |
| 11 [NR-I-A12] | I | A | H | Y | Y |
| 12 [NR-I-C3] | I | G | Y | N | Y |
| 13 [NR-I-D6] | I | A | H | Y | Y |
| 14 [NR-I-E7] | I | G | K | N | Y |
| 15 [NR-I-F5] | V | G | Y | R | K |

| SEQ ID NO | position in SEQ ID NO: 1 [NR-4] | | | | |
|---|---|---|---|---|---|
| | 41 | 136 | 224 | 229 | 320 |
| 1 [NR-4] | I | A | Y | Y | Y |
| 16 [NR-I-H5] | H | G | F | K | K |
| 17 [NR-II-A1] | S | G | K | Q | K |
| 18 [NR-II-B10] | V | G | M | N | K |
| 19 [NR-II-D4] | V | G | K | Y | F |
| 20 [NR-II-D11] | H | G | Y | K | Y |
| 21 [NR-II-D12] | S | G | F | K | F |
| 22 [NR-II-E1] | S | G | Y | K | Y |

Preferred biocatalysts comprise a polypeptide having at least 70%, at least 70%, at least 80%, at least 90%, at least 95%, at least 97%, at least 98% or at least 99% sequence identity to SEQ ID NO:1 [NR-4], and having the amino acid residues at the five positions corresponding to the conserved active site region of SEQ ID NO:1 [NR-4] as set out in Table 1.

Biocatalyst—Global Sequence

The biocatalyst may comprise a polypeptide comprising an amino acid sequence as set out as SEQ ID NO:1 [NR-4], 2 [NR-14], 3 [NR-17] or 4 [NR-24]. The biocatalyst may comprise a variant polypeptide comprising an amino acid sequence having at least 70% sequence identity to SEQ ID NO:1 [NR-4], 2 [NR-14], 3 [NR-17] or 4 [NR-24]. The biocatalyst may comprise a variant polypeptide comprising an amino acid sequence having at least 70%, at least 80%, at least 90%, at least 95%, at least 97%, at least 98% or at least 99% sequence identity to SEQ ID NO:1 [NR-4], 2 [NR-14], 3 [NR-17] or 4 [NR-24]. The biocatalyst may comprise a variant polypeptide comprising an amino acid sequence having at least 70%, at least 80%, at least 90%, at least 95%, at least 97%, at least 98% or least 99% sequence identity to SEQ ID NO:1 [NR-4], 2 [NR-14], 3 [NR-17] or 4 [NR-24] and having the amino acid residues at the five positions corresponding to the conserved active sire region of SEQ IN NO: 1 [NR-4] as set out in Table 1.

The biocatalyst may comprise a variant polypeptide having the amino acid sequence of NR-4 as set out in SEQ ID NO:1 [NR-4], and comprising one or more amino acid substitutions.

The biocatalyst may comprise a polypeptide having the amino acid sequence set out as SEQ ID NO: 14 [NR—I-E7]. The biocatalyst may comprise a variant polypeptide having an amino acid sequence having at least 70% identity to SEQ ID NO: 14 [NR—I-E7]. The biocatalyst may comprise a variant polypeptide having an amino acid sequence having at least 70%, at least 80%, at least 90%, at least 95%, at least 97%, at least 98% or at least 99% sequence identity to SEQ ID NO:14 [NR—I-E7]. The biocatalyst may comprise a variant polypeptide having an amino acid sequence having at least 70%, at least 80%, at least 90%, at least 95%, at least 97%, at least 98% or at least 99% sequence identity to SEQ ID NO:14 [NR—I-E7] and having the amino acid residues at the five positions corresponding to the conserved active site region of SEQ ID NO: 1 [NR-4] as set out in Table 1.

The biocatalyst may comprise a polypeptide having the amino acid sequence set out as SEQ ID NO: 22 [NR-II-E1]. The biocatalyst may comprise a variant polypeptide having an amino acid sequence having at least 70% identity to SEQ ID NO:22 [NR-II-E1]. The biocatalyst may comprise a variant polypeptide having an amino acid sequence having at least 70%, at least 80%, at least 90%, at least 95%, at least 97%, at least 98%, at least 99%, or 100% identity to SEQ ID NO:22 [NR-II-E1]. The biocatalyst may comprise a variant polypeptide having an amino acid sequence having at least 70%, at least 80%, at least 90%, at least 95%, at least 97%, at least 98% or at least 99% sequence identity to SEQ ID NO:22 [NR-II-E1] and having the amino acid residues at the five positions corresponding to the conserved active site region of SEQ ID NO:1 [NR-4] as set out in Table 1.

Preferred biocatalysts have nitroreductase activity and have motif (1) and have amino acid residues identical to the active site region of NR-4. Preferred biocatalysts comprise a polypeptide having nitroreductase activity and having motif (1) and having at least 70%, at least 70%, at least 80%, at least 90%, at least 95%, at least 97%, at least 98%, or at least 99% sequence identity to SEQ ID NO:1 [NR-4], and having the amino acid residues at the five positions corresponding to the conserved active site region of SEQ ID NO:1 [NR-4] as set out in Table 1.

Biocatalyst—General Information

All amino acid sequences described herein are reported starting from the N-terminus to the C-terminus.

Reference to "corresponding to" a residue of a polypeptide, such as "corresponding to residue 13 of NR-4" should be taken to mean the position in a query sequence that corresponds to residue 13 of NR-4 when that query sequence is optimally aligned with the full length NR-4 sequence.

The term "sequence identity" or "similarity" refers to nucleic acid sequence identity or amino acid sequence identity depending on the context as can be inferred by the skilled reader from the reference sequence.

Amino acid sequence identity and similarity and nucleic acid sequence identity may be measured using standard bioinformatics software tools, such as the freely available EMBOSS, or BLAST, software tools. Default parameters are generally used. For example EMBOSS Needle pairwise sequence alignment can be used to determine amino acid sequence identity. EMBOSS Needle pairwise sequence alignment, which uses the Needleman-Wunsch algorithm (J. Mol. Biol. (48): 444-453 (1970)), can be used to determine amino acid sequence similarity, for example using default parameters and using a BLOSUM scoring matrix such as the BLOSUM62 scoring matrix. Default parameters may be used with a gap creation penalty=12 and gap extension penalty=4. Use of GAP may be preferred but other algorithms may be used, e.g. BLAST or TBLASTN (which use the method of Altschul et al. (1990) J. Mol. Biol. 215:405-410), FASTA (which uses the method of Pearson and Lipman (1988) PNAS USA 85:2444-2448), or the Smith-Waterman algorithm (Smith and Waterman (1981) J. Mol Biol. 147:195-197), generally employing default parameters.

Percent (%) amino acid sequence identity with respect to a reference sequence is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Percent identity values may be determined by WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Percent (%) amino acid sequence alignment coverage with respect to a reference sequence is defined as the percentage of amino acid residues in the candidate sequence in comparison to the number of amino acid residues in the reference sequence, after aligning the sequences.

A variant polypeptide may be a truncated polypeptide. Any truncation may be used as long as the truncated polypeptide still has nitroreductase activity. Truncations may remove one or more residues from the N- and/or C-terminus of the polypeptide, which residues are non-essential for nitroreductase activity. Appropriate truncations may be routinely identified by systematic truncation of sequences of varying length from the N- and/or C-terminus.

A variant polypeptide may comprise one or more additional amino acids. A variant polypeptide may comprise an affinity tag for purifying the variant polypeptide, such as a poly-histidine tag, a T7 tag or a GST tag. An affinity tag may be located at the N- or C-terminus. Alternatively or additionally, the variant polypeptide may further comprise a leader sequence at the N-terminus. The leader sequence may be useful for directing secretion and/or intracellular targeting of the polypeptide in a recombinant expression system. Leader sequences are also known as signal peptides and are well known in the art. Alternatively or additionally, the polypeptide may further comprise a label such as a fluorescent label.

Amino acid substitutions may be conservative amino acid substitutions, in which an amino acid of a given sequence is substituted by an amino acid having similar characteristics. For example, where a hydrophobic amino acid (e.g. Leu) is substituted by another hydrophobic amino acid (e.g. Ile). Amino acids and conservative substitutions are shown in the table below. A conservative substitution may be defined as a substitution within an amino acid class and/or a substitution that scores positive in the BLOSUM62 matrix.

| Amino acid | Conservative substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Biocatalyst—Preparation

The biocatalyst may be provided in a pure, or substantially pure, form. The biocatalyst in a pure, or substantially pure, form is separated from other molecules or cellular components which naturally accompany a protein (e.g. ribosomes, cell membrane components).

The biocatalyst may be provided in a relatively crude form as a biocatalyst preparation, for example the biocatalyst preparation may be a lysate or clarified lysate of recombinant cells that express the biocatalyst. The biocatalyst preparation may be a homogenate or paste of recombinant cells that express the biocatalyst.

The biocatalyst may be comprised in a host cell. The biocatalyst may be provided in a free form or in an immobilised form. In immobilised form the biocatalyst may be attached to an inert carrier such as a cellulose powder or synthetic polymer such as polyethene (Lalonde and Margolin, 2002).

Provided herein are methods of producing the biocatalyst, which methods include expressing a nucleic acid encoding the biocatalyst in a host cell, and isolating the biocatalyst from the host cell. The method may include lysing the host cell to provide a cell lysate, and may further include removing host cell debris (e.g. by centrifugation) to provide a clarified cell lysate. The step of lysing the cell may use sonication. The step of lysing the host cell may use a lysis buffer that comprises flavin mononucleotide (FMN), for example the lysis buffer may comprise about 1-50 µM FMN, or about 5-25 µM FMN, or about 20 µM FMN. Additionally or alternatively, the step of lysing the host cell may use a lysis buffer that contains MgSO$_4$, for example the lysis buffer may comprise about 1-50 mM MgSO$_4$, about 1-5 mM MgSO$_4$, or about 5 mM MgSO$_4$. The lysis buffer may comprise FMN and MgSO$_4$.

The biocatalyst or biocatalyst preparation may be purified prior to use, for example a biocatalyst comprising an N-terminal Nis-tag may be purified using a suitable affinity column. Water may be removed from the biocatalyst or biocatalyst preparation to provide the biocatalyst in a lyophilised form. The biocatalyst may be provided as a lyophilisate. The biocatalyst or biocatalyst preparation may be frozen.

Substrate

The present invention provides a method of reducing an aromatic nitro compound. Thus, the method comprises the reaction of a substrate.

The substrate is an aromatic nitro compound. That is, the substrate is a compound in which the nitrogen atom of a nitro group (—NO$_2$) is directly bonded to a carbon ring atom of an aromatic group, such as a $C_{5-14}$ carboaryl or heteroaryl group.

The prefixes (e.g. $C_{5-14}$, $C_{5-7}$, $C_{5-6}$) denote the number of ring atoms, or range of number of ring atoms, whether carbon atoms or heteroatoms. For example, the term "$C_{5-6}$ aryl" as used herein, pertains to an aryl group having 5 or 6 ring atoms.

A $C_{5-14}$ carboaryl group comprises an aromatic ring in which all of the ring atoms are carbon atoms. A $C_{5-14}$ carboaryl group may be a $C_{6-14}$ or a $C_{6-10}$ carboaryl group. Examples of moonocyclic $C_{5-14}$ carboaryl groups include those derived from benzene (i.e. phenyl).

The $C_{5-14}$ carboaryl group may be part of a fused ring system. In a fused ring system the carboaryl group has a ring system comprising two or more rings, wherein at least one of the rings is an aromatic ring, and wherein each ring shares two adjacent ring atoms with each neighbouring (fused) ring. Thus, the bridgehead atoms are directly bonded. Examples of
$C_{5-14}$ carboaryl groups which comprise fused rings include groups derived from:
  (C9 groups) indane (2,3-dihydro-1H-indene), indene, isoindene;
  (C10 groups) naphthalene, dialin (1,2-dihydronaphthalene), tetralin (1,2,3,4-tetrahydronaphthalene), azulene;
  (C12 groups) acenaphthene;
  (C13 groups) fluorene, phenalene; and
  (C14 groups) anthracene and phenanthrene.

A $C_{5-14}$ heteroaryl group comprises an aromatic ring in which one or more ring atoms are heteroatoms. A $C_{5-14}$ heteroaryl group may be a $C_{5-14}$, $C_{5-10}$, or $C_{5-6}$ heteroaryl group. Examples of monocyclic $C_{5-14}$ heteroaryl groups include groups derived from:
  (C5 groups containing nitrogen) pyrrole (azole), pyrazole (1,2-diazole), imidazole (1,3-diazole), triazole, tetrazole;
  (C5 groups containing oxygen or sulfur) furan (oxole); thiophene (thiole);
  (C5 groups containing nitrogen and oxygen) oxazole, isoxazole, oxadiazole (e.g. furazan), oxatriazole;
  (C5 groups containing nitrogen and sulfur) thiazole, isothiazole;
  (C6 groups containing nitrogen) pyridine (azine), pyridazine (1,2-diazine), pyrimidine (1,3-diazine), pyrazine (1,4-diazine), triazine; and
  (C6 groups containing nitrogen and oxygen) isoxazine.

The $C_{5-14}$ heteroaryl group may be part of a fused ring system. In a fused ring system the heteroaryl group has a ring system comprising two or more rings, wherein at least one of the rings is an aromatic ring, and wherein each ring shares two adjacent ring atoms with each neighbouring (fused) ring. Thus, the bridgehead atoms are directly bonded. Examples of $C_{5-14}$ heteroaryl groups which comprise fused rings include groups derived from:
  (C9 groups with 2 fused rings) benzofuran, isobenzofuran, indole, isoindole, indolizine, indoline, isoindoline, purine, benzimidazole, indazole, benzoxazole, benzisoxazole, benzodioxole, benzofurazan, benzotriazole, benzothiofuran, benzothiazole, benzothiadiazole;
  (C10 groups with 2 fused rings) chromene, isochromene, chroman, isochroman, benzodioxan, quinoline, isoquinoline, quinolizine, benzoxazine, benzodiazine, pyridopyridine, quinoxaline, quinazoline cinnoline, phthalazine, naphthyridine, pteridine;

(C11 with 2 fused rings) benzodiazepine;

(C13 groups with 3 fused rings) carbazole, dibenzofuran, dibenzothiophene, carboline, perimidine, pyridoindole; and (C14 groups with 3 fused rings) acridine, xanthene, thioxanthene, oxanthrene, phenoxathiin, phenazine, phenoxazine, phenothiazine, thianthrene, phenanthridine, phenanthroline, phenazine.

The $C_{5-14}$ carboaryl or heteroaryl groups may be optionally substituted. The $C_{5-14}$ carboaryl or heteroaryl groups may have one, two or three substituents. That is, the $C_{5-14}$ carboaryl or heteroaryl groups may be mono-, di- or tri-substituted.

Where a carbon atom is present in a $C_{5-14}$ carboaryl or heteroaryl group, that carbon atom may be unsubstituted (CH) or optionally substituted with any substituent described below.

Where a nitrogen atom is present in a $C_{5-14}$ heteroaryl group, that nitrogen atom may be unsubstituted (NH) or optionally substituted with alkyl, alkenyl, alkynyl, cycloalkyl, heterocyclyl, aryl, acyl and acyloxy as described below.

Substituents

An alkyl group is a saturated hydrocarbon group, which is linear or branched. The alkyl group may be a $C_{1-20}$ alkyl group, for example a $C_{1-10}$, $C_{1-6}$ or a $C_{1-4}$ alkyl group. Examples of linear alkyl groups include methyl (-Me), ethyl (-Et), n-propyl (-nPr), n-butyl (-nBu), n-pentyl (-Amyl), n-hexyl and n-heptyl. Examples of branched alky groups include iso-propyl (-iPr), iso-butyl (-iBu), sec-butyl (-sBu), tert-butyl (-tBu), iso-pentyl, and neo-pentyl.

An alkenyl group is an alkyl group which contains one or more carbon-carbon double bonds. The alkenyl group may be a $C_{2-20}$ alkenyl group, for example a $C_{2-10}$, $C_{2-6}$ or a $C_{2-4}$ alkenyl group. The alkenyl group may be linear or branched. Examples of alkenyl groups include ethenyl (vinyl, 1-propenyl, 2-propenyl (allyl), isopropenyl (1-methylvinyl), butenyl, pentenyl, and hexenyl.

An alkynyl is an alkyl group having one or more carbon-carbon triple bonds. The alkynyl group may be a $C_{2-20}$ alkynyl group, for example a $C_{2-10}$, $C_{2-6}$ or a $C_{2-4}$ alkynyl group. The alkynyl group may be linear or branched. Examples of alkynyl groups include ethynyl and 2-propynyl (propargyl).

A heteroalkyl group is an alkyl group in which one or more carbon atoms is replaced with a heteroatom, for example N, O and S, and which is joined to the patent (substituted) group through a carbon atom. The heteroalkyl group may be a $C_{1-20}$ heteroalkyl group, for example a $C_{1-10}$, $C_{1-6}$ or a $C_{1-4}$ heteroalkyl group. Where a nitrogen atom is present in a heteroalkyl group, that nitrogen atom may be unsubstituted (NH) or optionally substituted with alkyl, alkenyl, alkynyl cycloalkyl, heterocyclyl, aryl, acyl and acyloxy as described below. Where a sulfur atom is present in a heteroalkyl group, that sulfur atom may be S, S(=O) or S(=O)$_2$. Examples of heteroalkyl groups include —CH$_3$OCH$_3$ and —CH$_2$OCH$_2$CH$_2$OCH$_3$.

A cycloalkyl group is an alkyl group which comprises a ring in which all of the ring atoms are carbon atoms. The cycloalkyl group may be a $C_{3-14}$ cycloalkyl group, for example a $C_{3-10}$, $C_{3-7}$ or a $C_{5-6}$ cycloalkyl group. Examples of monocylic cycloalkyl groups include cyclopropane, methylcyclopropane, dimethylcyclopropane, cyclobutane, methylcyclobutane, dimethylcyclobutane, cyclopentane, methylcyclopentane, dimethylcyclopentane, cyclohexane, methylcyclohexane and cycloheptane.

The cycloalkyl group may be part of a spiro ring system. In a spiro ring system the cycloalkyl group has a ring system comprising two or more rings, wherein in at least one of the rings all of the ring atoms are carbon atoms, and wherein each ring shares a single ring atom with each neighbouring (spiro) ring. Thus, there is a single bridgehead atom. Examples of cycloalkyl groups which comprise spiro rings are spiro [4.4]nonane, spiro [4.5]decane and spiro [5.5] undecane.

The cycloalkyl group may be part of a fused ring system. In a fused ring system the cycloalkyl group has a ring system comprising two or more rings, wherein in at least one of the rings all of the ring atoms are carbon atoms, and wherein each ring shares two adjacent ring atoms with each neighbouring (fused) ring. Thus, the bridgehead atoms are directly bonded. Examples of cycloalkyl groups which comprise fused rings include decalin.

The cycloalkyl group may be part of a bridged ring system. In a bridged ring system the cycloalkyl group has a ring system comprising two or more rings, wherein in at least one of the rings all of the ring atoms are carbon atoms, and wherein each ring shares three or more adjacent ring atoms with each neighbouring (bridged) ring. Thus, the bridgehead atoms are separated by one or more ring atoms. Examples of cycloalkyl groups which comprise bridged rings include norbornane, bornane and adamantane.

A heterocyclyl group comprises a ring in which one or more ring atoms are heteroatoms, for example N, O and S. The heterocyclyl group may be a $C_{5-10}$ heterocyclyl group, for example a $C_{5-7}$, $C_{5-6}$ or a Ce heterocyclyl group. Where a nitrogen ring atom is present in a heterocyclyl group, that nitrogen ring atom may be unsubstituted (NH) or optionally substituted with alkyl, alkenyl, alkynyl cycloalkyl, heterocyclyl, aryl, acyl and acyloxy as described herein. Where a sulfur ring atom is present in a heterocyclyl group, that sulfur ring atom may be S, S(=O) or S(=O)$_2$. Examples of monocyclic heterocycles include:

(C3 and C4 groups containing nitrogen) aziridine, azetidine;

(C3 and C4 groups containing oxygen or sulfur) oxirane, thiirane, oxetane, thietane;

(C5 groups containing nitrogen) pyrrolidine (tetrahydropyrrole), pyrroline (2,5-dihydropyrrole), imidazolidine, pyrazolidine (diazolidine), imidazoline, pyrazoline (dihydropyrazole);

(C5 groups containing oxygen and sulfur) oxolane (tetrahydrofuran), oxole (dihydrofuran), thiolane (tetrahydrothiophene), dioxolane, dioxolane, oxathiole;

(C5 groups containing nitrogen and oxygen) tetrahydrooxazole, dihydrooxazole, tetrahydroisoxazole, dihydroisoxazole;

(C5 groups containing nitrogen and sulfur) thiazoline, thiazolidine;

(C6 groups containing nitrogen) piperidine, dihydropyridine, tetrahydropyridine, piperazine;

(C6 groups containing oxygen and sulfur) oxane (tetrahydropyran), dihydropyran, pyran, thiane (tetrahydrothiopyran), dioxane, trioxane, oxathiane (thioxane), oxathiazine;

(C6 groups containing nitrogen and oxygen) morpholine, tetrahydrooxazine, dihydrooxazine, oxazine, oxadiazine;

(C6 groups containing nitrogen and sulfur) thiomorpholine;

(C7 groups containing nitrogen) azepine, diazepine; and (C7 groups containing oxygen and sulfur) oxepin, thiepane and dioxepane.

A halo group is independently selected from —F, —Cl, —Br and —I.

A hydroxyl group is —OH or the hydroxide form of this group.

An oxy group is a group —OR, where R is independently selected from alkyl, alkenyl, alkynyl, cycloalkyl, heterocyclyl, and aryl. Where R is alkyl, the oxy group is an alkoxy group. Examples of alkoxy groups include -OMe (methoxy), -OEt (ethoxy), —O(n-Pr) (n-propoxy), —O(iPr) (iso-propoxy), —O(nBu) (n-butoxy), —O(sBu) (sec-butoxy), —O(iBu) (iso-butoxy), and —O(tBu) (tert-butoxy).

A thio group is a group —SH or —SR, where R is independently selected from alkyl, alkenyl, alkynyl, cycloalkyl, heterocyclyl, and aryl.

An amino group is a group selected from —$NH_2$, —NHR, and —$N(R)_2$, where each R is independently selected from alkyl, alkenyl, alkynyl, cycloalkyl, heterocyclyl, and aryl, such as alkyl, cycloalkyl, and aryl.

A cyano group (nitrile) is —CN.

An acyl group is a group —C(=O)H or —C(=O)R, where —R is selected from alkyl, alkenyl, alkynyl, cycloalkyl, heterocyclyl, and aryl. Where an acyl group is a substituent to a nitrogen ring atom, the acyl group together with the nitrogen ring atom form an amido group. Examples of acyl groups include formyl, acetyl (—Ac), tert-butyryl and benzoyl (-Bz).

A carboxy group is —C(=O)OH or the carboxylate form of this group.

An acyloxy group (ester) is a group —C(=O)OR, where —R is selected from alkyl, alkenyl, alkynyl, cycloalkyl, heterocyclyl, and or aryl. Where an acyl group is a substituent to a nitrogen ring atom, the acyloxy group together with the nitrogen ring atom form a carbamate group.

An oxyacyl group (reverse ester) is a group —OC(=O)R, where —R is selected from alkyl, alkenyl, alkynyl, cycloalkyl, heterocyclyl, and aryl. Examples of oxyacyl groups include acetoxy (—OAc).

An amido group is a group —C(=O)$NH_2$, —C(=O)NHR or —C(=O)$NR_2$, where —R is independently selected from alkyl, alkenyl, alkynyl, cycloalkyl, heterocyclyl, and aryl, or two R groups may together with the nitrogen atom to which they are attached from a nitrogen heterocycle, optionally containing one further ring heteroatom.

An acylamino group is a group —NHC(=O)R, —NRC(=O)R where —R is independently selected from alkyl, alkenyl, alkynyl, cycloalkyl, heterocyclyl, and aryl, such as alkyl.

A sulfonic acid group is a group —$S(=O)_2$OH or the sulfonate form of this group.

A sulfonyl group is a group —$S(=O)_2$R where —R is selected from alkyl, alkenyl, alkynyl, cycloalkyl, heterocyclyl, and aryl. Examples of sulfonyl groups include methanesulfonyl (-OMs), trifluoromethanesulfonyl (-OTf) and 4-methanephenylsulfonyl (-OTs).

A sulfonamide group is a group —$S(=O)_2NH_2$, —$S(=O)_2$NHR or —$S(=O)_2NR_2$, where —R is independently selected from alkyl, alkenyl, alkynyl, cycloalkyl, heterocyclyl, and aryl.

A sulfoximide group (sulfoximine) is a group —S(=O)=NR, where —R is independently selected from alkyl, alkenyl, alkynyl, cycloalkyl, heterocyclyl, and aryl.

A phosphonate group is a group —P(=O)$(OH)_2$, —P(=O)(OH)(OR) or —P(=O)$(OR)_2$ where —R is independently selected from alkyl, alkenyl, alkynyl, cycloalkyl, heterocyclyl, and aryl.

Co-substrate

In the methods of the invention the substrate may react together with a co-substrate to yield a product. In a reduction reaction, the co-substrate may formally provide hydride ($H^-$) for the reduction. The co-substrate is typically a co-factor.

Cofactors

The biocatalyst may use NAD(P)H as a cofactor to provide reducing equivalents for the reduction reaction. For example, in catalysing the reduction of an aromatic nitro group the biocatalyst may use reducing equivalents from NAD(P)H, thereby oxidising it to NAD(P)+. The ratio of reduced cofactor to oxidised cofactor, for example the ratio of NAD(P)H to NAD(P)+, should be relatively high in order to favour cofactor oxidation and concomitant reduction of the substrate.

Cofactors are also known as coenzymes, and may also be known as co-substrates. The term "NAD(P)H" is used to indicate NADH and/or NADPH, and the term and "NAD (P)+" is used to indicate NAD+ and/or NADP+. For example a biocatalyst that uses "NAD(P)H" as a cofactor may use NADH as a cofactor and may additionally or alternatively use NADPH as a cofactor.

In one embodiment, the biocatalyst uses NADPH as cofactor.

In an in vitro reaction, the reduced cofactor may be present in a stoichiometric amount with the substrate. Alternatively, the reduced cofactor may be present in significantly less than a stoichiometric amount with the substrate. The reduced cofactor may be regenerated using a reduced cofactor regenerating system, which reduces the cofactor oxidised during the reaction and thereby allows the cofactor to be present in significantly less than a stoichiometric amount with the substrate. Reduced cofactor regeneration systems are known in the art. Such systems may comprise a hydride source optionally together with an enzyme capable of transferring reducing equivalents from the hydride source to the oxidised cofactor. Hydride sources include sugars, in particular hexoses such as glucose, mannose, fructose, hydride sources also include oxidisable alcohols such as ethanol, propanol, and isopropanol, and hydride sources also include formate, phosphite and molecular hydrogen. Such systems may comprise a sugar as a hydride source optionally with a compatible sugar dehydrogenase to catalyse the transfer of reducing equivalents from the sugar to the oxidised cofactor. For NADH or NADPH as cofactor, a reduced cofactor regenerating system may comprise glucose and glucose dehydrogenase (GDH). For NADH or NADPH as cofactor, a reduced cofactor regenerating system may comprise formate and formate dehydrogenase. For NADPH as cofactor, a cofactor regeneration system may comprise glucose-6-phosphate and glucose-6-phosphatase. For NADH or NADPH as cofactor, a cofactor regeneration system may comprise phosphite and phosphite dehydrogenase.

In an in vivo reaction, when the biocatalyst is provided in a cell, reduced NAD(P)H is regenerated by intracellular enzymes. Such enzymes may be endogenous or recombinant. For example intracellular enzymes involved in glycolysis such as glyceraldehyde phosphate dehydrogenase may reduce NAD+ to NADH.

The biocatalyst may be a flavin-dependent enzyme. That is, the biocatalyst may accept reducing equivalents from a cofactor to reduce an aromatic nitro group via a flavin prosthetic group, such as flavin mononucleotide (FMN), flavin adenine dinucleotide (FAD) or other flavins.

Methods

The present invention provides a method of reducing an aromatic nitro compound, comprising the step of contacting an aromatic nitro compound with a catalyst comprising (a) a disproportionation agent; and (b) a biocatalyst. Thus, the method is a method of synthesis comprising contacting a substrate with a catalyst to produce a product.

In one embodiment, the product is an aromatic hydroxylamine compound. That is, the method is a method of reducing an aromatic nitro compound to produce an aromatic hydroxylamine compound without further reduction or disproportionation.

In another embodiment, the product is an aromatic amine compound. That is, the method is a method of reducing an aromatic nitro compound to produce an aromatic amine compound. More specifically, the method is a method of reducing an aromatic nitro compounds to produce an aromatic hydroxylamine compound followed by further reduction or disproportionation to produce an aromatic amine compound.

Optionally, the substrate may react together with a co-substrate to provide the product. That is, the method further comprises the step of contact the biocatalyst with a co-substrate. The co-substrate may formally provide hydride ($H^-$) for the reduction. Thus, the co-substrate is oxidised during the reaction. The co-substrate is typically a co-factor. The cofactor may be NAD(P)H, as described herein.

Optionally, the cofactor may present in less than stoichiometric amount with respect to the substrate. The cofactor may be regenerated using a reduced cofactor regenerating system. That is, the method comprises the step of regenerating the cofactor using a reduced cofactor regeneration system, as described herein.

Optionally, the method further comprises the step of isolating the product, such as isolating the product from the catalyst and any remaining substrate. The isolation step may include the isolation of the product from by-products, such as those products that are derived from the substrate by partial- or over-reduction, or those products that are derives from the product by further reactions such as N-glycosylation. The isolating step may also include the step of isolating the product from the reaction medium.

Optionally, the method comprises the step of isolating the catalyst. The catalyst may be subsequently reused in a further method of the invention, as required.

In one embodiment, the method comprises the step of isolating the biocatalyst. For example, where the biocatalyst is provided in an immobilised form, for example attached to an inert carrier such as a cellulose powder or synthetic polymer such as polyethene, the biocatalyst may be isolated by filtration.

In another embodiment, the method comprises the step of isolating the disproportionation agent. For example, the disproportionation agent may be isolated by filtration.

The methods of the invention may be conducted in water or in an organic solvent. The methods of the invention may be conducted in a single solvent, or in a mixture of co-solvents. The reaction medium may be monophasic or biphasic.

The organic solvent may be selected from the group consisting of toluene, xylene, n-heptane, ethanol, isopropanol, diethyl ether, cyclopentyl methyl ether, tetrahydrofuran (THF), 2-methyl tetrahydrofuran, ethyl acetate, isopropyl acetate, isoamyl acetate, tert-butyl acetate, acetonitrile, methyl tert-butyl ether (MTBE), isopropanol, dimethylformamide (DMF), and dimethyl sulfoxide (DMSO) and other organic solvents whether miscible or immiscible in water.

In one embodiment, the co-solvent is selected from toluene, MTBE and DMSO.

The co-solvent may be present in an amount of at least 0.5 vol %, at least 1 vol % or at least 2 vol %.

The co-solvent may be present in an amount of at most 10 vol %, at most 15 vol % or at most 25 vol %.

In one embodiment, the co-solvent is present in an amount of around 5 vol %.

The reaction may be performed in a reaction medium where water is present at very low quantities, such as 5 v/v % or less with respect to the total volume of solvent. This is less preferred.

The reaction may be performed at ambient temperature, at an elevated temperature or at a lowered temperature.

The reaction may be performed at a temperature that is at least 30° C., at least 25° C., at least 20° C., at least 15° C., at least 10° C. or at least 0° C.

The reaction may be performed at a temperature that is at most 35° C., at most 40° C., at most 45° C. at most 50° C., at most 60° C., at most 70° C., at most 80° C. or at most 100° C. The inventors have found that the biocatalysts disclosed herein are tolerate of high and sustained temperatures. However, high and sustained temperatures are generally associated with loss of enzymatic activity, for example where a cofactor reaeration system is used.

The inventors have found that optimal results are obtained when the catalyst is used at a temperature that is in a range selected from the upper and lower amounts given above, for example in the range 20 to 45° C. or in the range 20 to 35° C.

A reaction in an aqueous medium may be performed at a pH within a limited range.

The pH of the reaction medium may be at least 3, at least 5, at least 6, at least 6.5 or at least 7.

The pH of the reaction medium may be at most 8, at most 9 or at most 10.

The inventors have found that optimal results are obtained when the catalyst is used at a pH that is in a range selected from the upper and lower amounts given above, for example in the range pH 6.5 to 8.

The pH of the reaction medium may refer to the pH of the reaction medium at the start of the reaction.

The reaction may be performed in the presence or absence of a buffer.

A buffer may be provided in the reaction medium to maintain the pH of the reaction medium with a range selected from the upper and lower values given above. Example buffers include those containing potassium phosphate, Tris, HEPES, Bicine, MOPS and CAPS.

The buffer may be provided in the reaction medium at the beginning of the reaction, or it may be added to the reaction medium as the reaction progresses. The buffer may be added batch-wise or continuously.

The reaction may be performed in a portion-wise manner. That is, the substrate may be added in discrete portions (batches) to a reaction mixture comprising the catalyst. The substrate may be added neat or as a solution in a solvent.

The substrate may be added in 2 to 10 portions, for example, 2 to 8 portions or 2 to 4 portions.

The portions may be the same size, or they may be different. For example, a first portion may comprise 50% of the total substrate amount followed by two further portions each comprising 25% of the total substrate amount.

The interval (time) between adding portions of substrate may be the same or may be different. For example, the interval between a first and second portion may be 30 minutes, while the interval between the second and a third portion may be 1 hour.

The reaction may be performed in a continuous-feed manner. That is, the substrate may be continuously added to a reaction mixture comprising the catalyst. For example, substrate may be added in a drop-wise manner. Alternatively, the substrate may be added using a pump, for example a syringe pump. The substrate may be added neat or as a solution in a solvent.

The reaction may be performed in a step-wise manner. This is, the substrate may be transformed first to an intermediate. Subsequently, the intermediate may be transformed into a final product. The intermediate may be isolated prior to transformation into a final product. Alternatively, the intermediate may remain in the initial reaction medium prior to transformation into a final product. Typically the intermediate is a hydroxylamine compound.

The substrate may be present at a concentration of at least 0.1 mM, at least 0.5 mM, at least 1 mM, at least 5 mM, at least 10 mM, at least 20 mM, at least 50 mM, at least 100 mM, at least 200 mM, at least 300 mM, at least 400 mM or at least 500 mM.

The substrate may be present at a concentration of at most 50 mM, at most 100 mM, at most 200 mM, at most 300 mM, at most 500 mM, at most 1,000 mM, at most 1,500 mM or at most 2,000 mM.

The inventors have found that optimal results are obtained when the substrate is used at a concentration that is in a range selected from the upper and lower amounts given above, for example in the range 20 mM to 1,000 mM, such as 20 mM to 200 mM.

The substrate may be present at a concentration of at least 5 mg/L, 10 mg/L, at least 50 mg/L, at least 100 mg/L, at least 500 mg/L, at least 1,000 mg/L, at least 5 g/L, at least 10 g/L, at least 20 g/L, at least 30 g/L, at least 40 g/L or at least 50 g/L.

The substrate may be present at a concentration of at most 1,000 mg/L, 5 g/L, at most 10 g/L, at most 20 g/L, at most 30 g/L, at most 50 g/L, at most 100 g/L, at most 150 g/L or at most 200 g/L.

The amount of catalyst required in a reaction may be small in relation to the amount of substrate present and low in terms of its concentration in the reaction medium.

The biocatalyst may be present at a concentration of at least 0.05 g/L, at least 0.10 g/L, at least 0.25 g/L, at least 0.5 g/L, at least 1.0 g/L or at least 2.0 g/L.

The biocatalyst may be present at a concentration of at most 0.05 g/L, at most 0.50 g/L, at most 1.0 g/L, at most 2.0 g/L, at most 5.0 g/L or at most 10.0 g/L.

In one embodiment, the biocatalyst is present at a concentration of around 5.0 g/L.

The disproportionation agent may be present at a concentration of at least 0.1 mM, at least 0.2 mM, at least 0.5 mM, at least 1 mM, at least 2 mM, at least 5 mM, at least 10 mM, at least 20 mM, at least 50 mM, or at least 100 mM.

The disproportionation agent may be present at a concentration of at most 1 mM, at most 2 mM, at most 5 mM, at most 10 mM, at most 20 mM, at most 50 mM at most 100 mM, at most 200 mM or at most 500 mM.

In one embodiment, the disproportionation agent is present at a concentration of around 5 mM.

The disproportionation agent may be present in a ratio of at least 0.00001 equivalents, at least 0.0001 equivalents, at least 0.001 equivalents or at least 0.01 equivalents with respect to the substrate.

The disproportionation agent may be present in a ratio of at most 0.1 equivalents, at most 1 equivalent or at most 10 equivalents with respect to the substrate.

In one embodiment, the disproportionation agent is present at a ratio of around 0.1 equivalents with respect to the substrate.

The reaction may be conducted for sufficient time to allow for the generation of a desirable quantity of material. Subsequently, the reaction mixture may be worked up to isolate the product material.

In one embodiment, the reaction time is at least 20 minutes, at least 30 minutes, at least 40 minutes, at least 1 hour or at least 2 hours.

In one embodiment, the reaction time is at most 18 hours, at most 24 hours, at most 36 hours, at most 48 hours, at most 72 hours, at most 96 hours, or at most 120 hours.

The end of the reaction may be the point at which the catalyst and the product are separated.

The reaction may be deemed complete when the yield of the desired product does not increase substantially over time.

In one embodiment, the reaction is performed ex vivo, such as an in vitro. An in vitro reaction refers to an extracellular or cell-free reaction.

Uses

The present invention provides the use of (a) a disproportionation agent; and (b) a biocatalyst as a catalyst for reducing an aromatic nitro compound. Thus, the catalyst may be used in a method of synthesis to transform a substrate into a product.

The substrate is an aromatic nitro compound as described herein.

In one embodiment, the product is an aromatic hydroxylamine compound. That is, the catalyst may be used to reduce an aromatic nitro compound to an aromatic hydroxylamine compound without further reduction or disproportionation.

In another embodiment, the product is an aromatic amine compound. That is, the catalyst may be used to reduce an aromatic nitro compound to an aromatic hydroxylamine compound followed by further reduction or disproportionation to give an aromatic amine compound.

The catalyst may be used in combination with a co-substrate. The co-substrate may formally provide hydride (H$^-$) for the reduction. The co-substrate is typically a cofactor. The biocatalyst may use NAD(P)H as cofactor, as described herein.

The catalyst may be used in water or in an organic solvent, either as a single solvent or as a mixture of co-solvents, as described herein.

The catalyst may be used at ambient temperature, elevated temperature or lowered temperature, as described herein.

The catalyst may be used in an aqueous medium at a pH within a limited range, as described herein. The catalyst may be used in combination with a buffer to maintain the pH of the reaction medium within a range, as described herein.

The catalyst may be used in an amount that may be small in relation to the amount of substrate present and low in terms of its concentration in the reaction mixture. The biocatalyst and disproportionation agent may be present at a concentration as described herein.

The catalyst may be used in an ex vivo reaction, such as an in vitro. An in vitro reaction refers to an extracellular or cell-free reaction.

Kits

The present invention provides a kit comprising (a) a disproportionation agent; and (b) a biocatalyst. Thus, the kit may be used to implement a method of synthesis comprising contacting a substrate with a catalyst to produce a product.

The disproportionation agent may be spatially separated from the biocatalyst in the kit. Thus, the disproportionation agent may be provided in a well of a well plate, or in a separate vial or other container.

The kit may comprise a set of instructions for completing a method as described herein.

The kit may comprise additional reagents for use with the catalyst.

The kit may comprise a co-substrate, for example a reducing agent. The reducing agent may formally provide hydride (H) for a reduction reaction. The reducing agent is typically a co-factor. The kit may comprise NAD(P)H as cofactor, as described herein.

The kit may comprise a solvent, for example water, typically with another solvent ("co-solvent"), as described herein.

The kit may comprise a buffer to maintain the pH of a reaction medium within a range, as described herein.

The kit may comprise the disproportionation agent and biocatalyst in different amounts, for example the kit may comprise a greater amount of disproportionation agent than biocatalyst.

The kit may comprise one or more further catalysts. A further catalyst may be for use in a reduction reaction, such as the reduction of an aromatic nitro group as described herein. Additionally or alternatively, a further catalyst may be for use in a reaction that is not a reduction reaction, or is not the reduction of an aromatic nitro group.

The further catalyst may be a biocatalyst. Thus, the further catalyst may have enzymatic activity. The further catalyst may have cofactor regenerating activity.

The kit may comprise a reference substrate, for example, to establish the activity of each catalyst within the kit.

A catalyst may be spatially separated from other catalysts or other components of the kit. Thus, a catalyst may be provided in a well of a well plate, or in a separate vial or other container.

Other Embodiments

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental

Biocatalyst—Preparation

The biocatalysts reported in this paper were identified from publicly available database NCBI and have the following RefSeq Accession code in the NCBI database: NR-4 WP_003178951.1, NR-14 WP_006881391.1, NR-17 WP_003683965.1, NR-24 WP_011135791.1, NR-32 WP_050864130.1 and NR-35 WP_001001176.1, ENE-101 WP_013592569.1, ENE-102 WP_011137048.1, ENE-103 WP_009794721.1. Gene strings were ordered from Life Science Technologies and cloned into the plasmid pJEx401 using the flanking restriction sites NdeI/XhoI according to standard cloning procedures. For biocatalyst expression, the plasmids were transformed in E. coli BL21, one colony from the LB-kanamycin plate was used to inoculate 2 mL LB-kanamycin liquid medium pre-culture. Pre-cultures were incubated for 18 hours at 37° C. and 180 rpm. The whole preculture was used to inoculate 200 mL TB medium containing 50 µg/mL kanamycin in 1 L baffled shake flasks. The cultures were incubated at 37° C. and 180 rpm until $OD_{600}$ reached approximately 1 and then were induced using 0.1 mM IPTG and the temperature was lowered to 30° C. After overnight incubation, the cells were harvested at 4200 rpm for 20 minutes (Heraeus Multifuge X3R) and cells were resuspended in Potassium Phosphate buffer 100 mM pH 7. Cell lysis was performed by sonication using Sonica Vibra Cell ultrasonicator (2 minutes, pulse on 5 seconds, pulse off 2 seconds, 60% amplitude). Cell lysates were clarified at 11.000 rpm for 15 minutes, the supernatant was filtered using 0.22 µm syringe filters and the resulting clarified cell extract was frozen at −80° C. Lyophilisation of was performed for using Christ Alpha 1-2 LDplus Freeze Dryer, a single drying cycle of 24 hours was applied at a vacuum pressure of 0.27 mbar.

For purification purposes, the recombinant biocatalysts with an N-terminal His-tag were expressed following the above-described procedure. The supernatant was used for enzyme purification on a Bio-Rad BioLogic LP Chromatography System machine. The crude extract was loaded on a 5 mL HisTrap GE column and eluted with a semi-linear gradient (0-500 mM imidazole), using binding buffer (100 mM phosphate buffer pH 7.5 with 300 mM NaCl and 5 mM imidazole) and elution buffer (100 mM phosphate buffer pH 7.5 with 300 mM NaCl and 500 mM imidazole). During the elution phase, fractions of 5 mL were collected and a protein gel was run to identify the fractions containing the biocatalyst protein. The correct fractions were then combined and concentrated in Sartorius™ Vivaspin™ 20 Centrifugal Concentrators, desalted using GE Healthcare PD-10 Columns, flash-frozen and stored at −80° C.

The proteins were analysed by SDS-PAGE (15% resolving gel and 5% stacking gel in a Tris-glycine buffer system) and were found to be more than 95% pure.

Nitro and Amine Starting Materials

Nitro compounds 2a-2l, 2n, 2o, 2p and the corresponding amine compounds were purchased from Sigma Aldrich. 2-Chloro-3-nitropyridine 2m and the corresponding amine was purchased from Apollo Scientific.

Analytical HPLC Method—HPLC Settings

HPLC analysis was performed on JASCO Pu-2080 plus equipped with Zorbax SB-Phenyl column 5 µm, 4.6×250 mm (Agilent), using the conditions shown below.

Mobile phase (A): water with 0.1% v/v TFA

Mobile phase (B): acetonitrile with 0.1% v/v TFA

Flow rate: 1 mL/min.

Column temperature: 25° C.

Detector: 220 nm.

TABLE 2

| Time (min) | % Mobile Phase B |
|---|---|
| HPLC gradient method 1 | |
| 0.0 | 5 |
| 2.0 | 5 |
| 15.0 | 95 |
| 15.1 | 5 |
| 20.0 | 5 |
| HPLC gradient method 2 | |
| 0.0 | 5 |
| 2.0 | 5 |
| 17.0 | 95 |
| 22.0 | 95 |
| 22.1 | 5 |
| 24.0 | 5 |

The observed retention times of the nitro compounds are shown in Table 3.

TABLE 3

Retention times of analytes

| Substrate | HPLC method | Nitro 2 $R_t$ (min) | Amine 1 $R_t$ (min) | Hydroxylamine 3 $R_t$ (min) | Azoxy 6 $R_t$ (min) | Azo 4 $R_t$ (min) |
|---|---|---|---|---|---|---|
| 2a | 1 | 15.1 | 10.3 | 9.5 | 12.8 | nd |
| 2b | 1 | 15.1 | 9.8 | 9.5 | 12.5 | nd |
| 2c | 1 | 14.9 | 9.2 | 9.25 | 12 | nd |
| 2d | 1 | 14.9 | 9.1 | 9.5 | 11 | nd |
| 2e | 1 | 13.4 | 5.4 | 8.1 | 10.8 | nd |
| 2f | 2 | 15.5 | 8.9 | 12.8 | 18.6 | nd |
| 2g | 2 | 15.6 | 9.1 | 12.9 | 18.7 | nd |
| 2h | 2 | 15.2 | 11.1 | 12.3 | 17.4 | nd |
| 2i | 1 | 13.2 | 11.9 | Nd | nd | nd |
| 2j | 1 | 13.2 | 8.8 | Nd | 11 | nd |
| 2k | 1 | 13.3 | 11.2 | Nd | 10.6 | nd |
| 2l | 1 | 12.2 | 9.2 | Nd | 11.2 | nd |
| 2m | 1 | 12.7 | 9.3 | 8.8 | nd | nd |
| 2n | 2 | 17.5 | 12.1 | 19.9 | nd | nd |
| 2o | 1 | 12.8 | 8.7 | Nd | nd | 9.8 |
| 2p | 1 | 15.1 | 13.2 | 10.7 | nd | nd |

Biocatalyst—Initial Screen

An initial screen of biocatalysts was conducted using 2-ethyl-nitrobenzene 2d and nitrobenzene 2e as reference in order to identify potential candidates for this biocatalytic transformation. Each reaction contained 475 µL of buffer 250 mM potassium phosphate (pH 6.0; 7.0 or 8.0)+1 mM NADP$^+$ and 1 mM NAD$^+$, 100 mM D-glucose, 1 mg/mL GDH+5 mg/mL NR enzyme+25 µL substrate 2d or 2e solution (0.4 M in MTBE, final concentration of substrate 20 mM)+50 µL V$_2$O$_5$ (20 mM stock, final concentration 2 mM). The reactions were shaken at 35° C. for 18 hours. The reactions were quenched with ACN (1 mL), vortexed and centrifuged. Samples were then collected and analysed by HPLC. The results of the screen are shown in Table 4 and Table 5.

TABLE 4

Screening of biocatalysts using 2d as substrate

| Example (2) | Nitro | Enzyme | V$_2$O$_5$ (mM) | 3 (%)$^a$ | 1 (%)$^a$ | 6 (%)$^a$ | 2 (%)$^a$ | Other (%) |
|---|---|---|---|---|---|---|---|---|
| 1 | 2d | NR-3 | 2 mM | 0 | 5.6 | 1.6 | 92.7 | 0 |
| 2 | 2d | NR-4 | 2 mM | 0 | 80.2 | 2.6 | 1.9 | 15.1 |
| 3 | 2d | NR-6 | 2 mM | 0 | 0.5 | 5.7 | 93.7 | 0 |
| 4 | 2d | NR-7 | 2 mM | 0 | 0 | 0 | 100 | 0 |
| 5 | 2d | NR-8 | 2 mM | 0 | 0 | 8.8 | 91.1 | 0 |
| 6 | 2d | NR-9 | 2 mM | 0 | 0 | 4.1 | 95.9 | 0 |
| 7 | 2d | NR-10 | 2 mM | 0 | 0.2 | 3.8 | 95.8 | 0 |
| 8 | 2d | NR-12 | 2 mM | 0 | 8.2 | 6.6 | 83.1 | 2.2 |
| 9 | 2d | NR-13 | 2 mM | 0 | 0 | 0.9 | 99.1 | 0 |
| 10 | 2d | NR-14 | 2 mM | 0 | 4.4 | 0 | 93.6 | 1.9 |
| 11 | 2d | NR-16 | 2 mM | 0 | 0 | 13.4 | 86.5 | 0 |
| 12 | 2d | NR-17 | 2 mM | 0 | 16.4 | 0 | 81.9 | 1.6 |
| 13 | 2d | NR-18 | 2 mM | 0 | 0 | 4.5 | 95.5 | 0 |
| 14 | 2d | NR-19 | 2 mM | 0 | 0 | 11.3 | 88.7 | 0 |
| 15 | 2d | NR-20 | 2 mM | 0 | 8.1 | 0.9 | 89.5 | 1.5 |
| 16 | 2d | NR-22 | 2 mM | 0 | 2.8 | 0 | 97.2 | 0 |
| 17 | 2d | NR-23 | 2 mM | 0 | 4.3 | 3.9 | 91.7 | 0 |
| 18 | 2d | NR-24 | 2 mM | 0 | 68.9 | 6.8 | 15.9 | 8.3 |
| 19 | 2d | NR-25 | 2 mM | 0 | 2.7 | 0 | 95.3 | 1.9 |
| 20 | 2d | NR-26 | 2 mM | 0 | 2.3 | 0 | 97.6 | 0 |
| 21 | 2d | NR-27 | 2 mM | 0 | 0 | 0 | 100 | 0 |
| 22 | 2d | NR-28 | 2 mM | 0 | 2.3 | 0 | 97.7 | 0 |
| 23 | 2d | NR-30 | 2 mM | 0 | 1.4 | 0 | 97.2 | 1.3 |
| 24 | 2d | NR-31 | 2 mM | 0 | 3.1 | 4.4 | 92.5 | 0 |
| 25 | 2d | NR-32 | 2 mM | 0 | 2.7 | 1.6 | 93.3 | 2.3 |
| 26 | 2d | NR-33 | 2 mM | 0 | 0 | 0 | 100 | 0 |
| 27 | 2d | NR-34 | 2 mM | 0 | 0 | 0 | 100 | 0 |
| 28 | 2d | NR-35 | 2 mM | 0 | 0 | 0 | 100 | 0 |
| 29 | 2d | NR-36 | 2 mM | 0 | 5.7 | 4.3 | 89.9 | 0 |
| 30 | 2d | ENE-101 | 2 mM | 0 | 1.2 | 0 | 94.4 | 4.4 |
| 31 | 2d | NR-37 | 2 mM | 0 | 4.2 | 0 | 94.1 | 1.7 |
| 32 | 2d | NR-38 | 2 mM | 0 | 0 | 11.8 | 88.1 | 0 |
| 33 | 2d | NR-39 | 2 mM | 0 | 1.6 | 2.3 | 96.1 | 0 |
| 34 | 2d | NR-40 | 2 mM | 0 | 1 | 0 | 97.5 | 1.4 |
| 35 | 2d | NR-41 | 2 mM | 0 | 0 | 0 | 97.9 | 2 |
| 36 | 2d | NR-43 | 2 mM | 0 | 3.5 | 0 | 82.3 | 14.4 |
| 37 | 2d | NR-44 | 2 mM | 0 | 3.9 | 3.6 | 92.4 | 0 |
| 38 | 2d | NR-45 | 2 mM | 0 | 0.5 | 3.7 | 95.6 | 0 |
| 39 | 2d | NR-46.2 | 2 mM | 0 | 3.3 | 0 | 96.7 | 0 |
| 40 | 2d | NR-46.3 | 2 mM | 0 | 3.2 | 0 | 96.8 | 0 |

$^a$Uncorrected values

TABLE 5

Screening of biocatalysts using 2e as substrate

| Example (2) | Nitro | Enzyme | V$_2$O$_5$ (mM) | 3 (%)$^a$ | 1 (%)$^a$ | 4 (%)$^a$ | 6 (%)$^a$ | 2 (%)$^a$ | Other (%) |
|---|---|---|---|---|---|---|---|---|---|
| 1 | 2e | NR-3 | 2 mM | 0 | 1.1 | 0 | 8 | 90.8 | 0 |
| 2 | 2e | NR-4 | 2 mM | 0 | 74.3 | 3.4 | 17.3 | 0 | 4.9 |
| 3 | 2e | NR-6 | 2 mM | 0 | 9.7 | 4.9 | 10.7 | 72.3 | 0 |
| 4 | 2e | NR-7 | 2 mM | 0 | 4 | 1.7 | 11.4 | 80.7 | 0 |
| 5 | 2e | NR-8 | 2 mM | 0 | 1.5 | 0 | 8.4 | 88.7 | 0 |
| 6 | 2e | NR-9 | 2 mM | 0 | 1.9 | 0 | 17.2 | 80.7 | 0 |
| 7 | 2e | NR-10 | 2 mM | 0 | 1.7 | 0 | 2.8 | 95.4 | 0 |
| 8 | 2e | NR-12 | 2 mM | 0 | 71.9 | 1.8 | 24.9 | 1.3 | 0 |
| 9 | 2e | NR-13 | 2 mM | 0 | 0 | 0 | 1.5 | 98.5 | 0 |
| 10 | 2e | NR-14 | 2 mM | 0 | 71.3 | 2.3 | 24.9 | 1.3 | 0 |
| 11 | 2e | NR-16 | 2 mM | 0 | 2.1 | 0 | 5.4 | 92.5 | 0 |
| 12 | 2e | NR-17 | 2 mM | 0 | 80.7 | 1.8 | 17.1 | 0.4 | 0 |
| 13 | 2e | NR-18 | 2 mM | 0 | 1.4 | 0 | 14 | 84.7 | 0 |
| 14 | 2e | NR-19 | 2 mM | 0 | 3.7 | 1.9 | 12 | 82.3 | 0 |
| 15 | 2e | NR-20 | 2 mM | 0 | 78.7 | 3.1 | 18.1 | 0 | 0 |
| 16 | 2e | NR-22 | 2 mM | 0 | 43.3 | 8.7 | 18.5 | 29.3 | 0 |
| 17 | 2e | NR-23 | 2 mM | 0 | 79.7 | 3.5 | 16.8 | 0 | 0 |
| 18 | 2e | NR-24 | 2 mM | 0 | 81 | 2.6 | 12.5 | 0 | 3.8 |
| 19 | 2e | NR-25 | 2 mM | 0 | 12.6 | 5.5 | 13.1 | 68.8 | 0 |
| 20 | 2e | NR-26 | 2 mM | 0 | 5.8 | 9.9 | 8.6 | 75.7 | 0 |
| 21 | 2e | NR-27 | 2 mM | 0 | 1.5 | 0 | 3.2 | 95.2 | 0 |
| 22 | 2e | NR-28 | 2 mM | 0 | 64 | 3.7 | 22.2 | 10.1 | 0 |
| 23 | 2e | NR-30 | 2 mM | 0 | 54.5 | 8.7 | 19.2 | 17.5 | 0 |
| 24 | 2e | NR-31 | 2 mM | 0 | 37.5 | 5.5 | 15.1 | 38.6 | 3.3 |
| 25 | 2e | NR-32 | 2 mM | 0 | 19.8 | 6.8 | 10.7 | 62.6 | 0 |
| 26 | 2e | NR-33 | 2 mM | 0 | 15.2 | 5.6 | 14.1 | 65.1 | 0 |
| 27 | 2e | NR-34 | 2 mM | 0 | 9 | 2.9 | 15.7 | 72.3 | 0 |

TABLE 5-continued

Screening of biocatalysts using 2e as substrate

| Example | Nitro (2) | Enzyme | $V_2O_5$ (mM) | 3 (%)$^a$ | 1 (%)$^a$ | 4 (%)$^a$ | 6 (%)$^a$ | 2 (%)$^a$ | Other (%) |
|---|---|---|---|---|---|---|---|---|---|
| 28 | 2e | NR-35 | 2 mM | 0 | 1.4 | 0 | 5.8 | 92.7 | 0 |
| 29 | 2e | NR-36 | 2 mM | 0 | 77.5 | 1.6 | 18.5 | 0 | 2.7 |
| 30 | 2e | ENE-101 | 2 mM | 0 | 13.6 | 7.8 | 9.2 | 69.3 | 0 |
| 31 | 2e | NR-37 | 2 mM | 0 | 12.6 | 8.1 | 6.6 | 72.6 | 0 |
| 32 | 2e | NR-38 | 2 mM | 0 | 65.9 | 6.1 | 22.1 | 5.8 | 0 |
| 33 | 2e | NR-39 | 2 mM | 0 | 22.5 | 7.5 | 20.1 | 49.5 | 0 |
| 34 | 2e | NR-40 | 2 mM | 0 | 75.2 | 6.2 | 18.5 | 0 | 0 |
| 35 | 2e | NR-41 | 2 mM | 0 | 5.4 | 4.6 | 4.7 | 88.3 | 0 |
| 36 | 2e | NR-43 | 2 mM | 0 | 71.8 | 8.2 | 19.8 | 0 | 0 |
| 37 | 2e | NR-44 | 2 mM | 0 | 75.7 | 7.2 | 16.9 | 0.2 | 0 |
| 38 | 2e | NR-45 | 2 mM | 0 | 56.2 | 7.3 | 22.4 | 14 | 0 |
| 39 | 2e | NR-46.2 | 2 mM | 0 | 72.2 | 7.8 | 11.8 | 8.1 | 0 |
| 40 | 2e | NR-46.3 | 2 mM | 0 | 76.9 | 5.9 | 16.1 | 1 | 0 |

$^a$Uncorrected values

Two of the enzymes screened, NR-4 and NR-24 display a high activity of 2-ethyl-nitrobenzene 2d (Table 4, entries 2 and 18), while the other enzymes only show marginal activity. The nitrobenzene 2e is much better accepted by the enzyme panel, 13 out of 40 enzymes showing >70% conversion of the substrate 2e to the corresponding amine 1e. In addition, the proportion of starting material in these examples is very low, typically under 5%, the remaining 25% being formed of intermediates 6e (azoxy) and 4e (diazo).

These results allow a process of selection of enzymes for future applications based on their preference for certain substrates.

Disproportionation Agent—Initial Screen

An initial screen of metal additives for the disproportionation of the hydroxylamine intermediate 3 was conducted using two nitroreductases, NR-4 and NR-36 and a selection of five metal additives (CuCl$_2$, FeCl$_2$, NaMoO$_4$ and CoCl$_2$, and V$_2$O$_5$). Each reaction contained 475 µL of buffer 250 mM potassium phosphate (pH 6.0; 7.0 or 8.0)+1 mM NADP$^+$ and 1 mM NAD$^+$, 100 mM D-glucose, 1 mg/mL GDH+5 mg/mL NR enzyme+25 µL substrate 2a-e solution (0.4 M in MTBE, final concentration of substrate 20 mM)+50 µL metal additive (20 mM stock, final concentration 2 mM). The reactions were shaken at 35° C. for 18 hours. The reactions were quenched with ACN (1 mL), vortexed and centrifuged. Samples were then collected and analysed by HPLC. The results of the screen are shown in Table 6.

TABLE 6

Screening of metal additives using NR-4 and NR-36 as nitroreductases

| Example | Nitro (2) | Enzyme | Metal Additive | 3 (%)$^a$ | 1 (%)$^a$ | 6 (%)$^a$ | 2 (%)$^a$ | Other (%) |
|---|---|---|---|---|---|---|---|---|
| 1 | 2a | NR-4 | CuCl$_2$ | 28.7 | 30.2 | 9.5 | 31.5 | 0 |
| 2 | 2b | NR-4 | CuCl$_2$ | 30.7 | 29.9 | 4.4 | 35.1 | 0 |
| 3 | 2c | NR-4 | CuCl$_2$ | 10.8 | 22 | 6.9 | 60.1 | 0 |
| 4 | 2d | NR-4 | CuCl$_2$ | 18.9 | 78.3 | 0 | 2.8 | 0 |
| 5 | 2e | NR-4 | CuCl$_2$ | 1.9 | 60.2 | 3.9 | 6.6 | 28.3 |
| 6 | 2a | NR-36 | CuCl$_2$ | 14.3 | 0 | 0 | 85.6 | 0 |
| 7 | 2b | NR-36 | CuCl$_2$ | 15.3 | 0 | 0 | 84.7 | 0 |
| 8 | 2c | NR-36 | CuCl$_2$ | 0 | 21.1 | 0 | 78.9 | 0 |
| 9 | 2d | NR-36 | CuCl$_2$ | 5.4 | 0 | 0 | 94.6 | 0 |
| 10 | 2e | NR-36 | CuCl$_2$ | 1.7 | 5.7 | 4.5 | 77.1 | 10.9 |
| 11 | 2a | NR-4 | FeCl$_2$ | 7.3 | 11.9 | 78.6 | 2.2 | 0 |
| 12 | 2b | NR-4 | FeCl$_2$ | 8.4 | 64.3 | 13.8 | 13.4 | 0 |
| 13 | 2c | NR-4 | FeCl$_2$ | 71.5 | 0 | 4.9 | 23.5 | 0 |
| 14 | 2d | NR-4 | FeCl$_2$ | 0.6 | 19.7 | 75.6 | 4.1 | 0 |
| 15 | 2e | NR-4 | FeCl$_2$ | 45.7 | 41.7 | 6.8 | 2.1 | 3.5 |
| 16 | 2a | NR-36 | FeCl$_2$ | 0 | 4.8 | 79.6 | 15.5 | 0 |
| 17 | 2b | NR-36 | FeCl$_2$ | 0 | 10.1 | 31.1 | 58.8 | 0 |
| 18 | 2c | NR-36 | FeCl$_2$ | 13 | 0 | 12.1 | 74.8 | 0 |
| 19 | 2d | NR-36 | FeCl$_2$ | 0 | 8.2 | 19.9 | 71.8 | 0 |
| 20 | 2e | NR-36 | FeCl$_2$ | 39.1 | 40.1 | 7.3 | 1.6 | 11.8 |
| 21 | 2a | NR-4 | NaMoO$_4$ | 0 | 7.6 | 90.5 | 1.8 | 0 |
| 22 | 2b | NR-4 | NaMoO$_4$ | 6.5 | 49.4 | 26.9 | 17.1 | 0 |
| 23 | 2c | NR-4 | NaMoO$_4$ | 13.6 | 14.8 | 20.3 | 51.1 | 0 |
| 24 | 2d | NR-4 | NaMoO$_4$ | 1.8 | 21.7 | 62.9 | 13.5 | 0 |
| 25 | 2e | NR-4 | NaMoO$_4$ | 82.4 | 12.6 | 2.1 | 2.7 | 0 |
| 26 | 2a | NR-36 | NaMoO$_4$ | 0 | 6.9 | 79.5 | 13.5 | 0 |
| 27 | 2b | NR-36 | NaMoO$_4$ | 0 | 6.8 | 20.7 | 72.4 | 0 |
| 28 | 2c | NR-36 | NaMoO$_4$ | 14.1 | 14.5 | 4.6 | 66.7 | 0 |
| 29 | 2d | NR-36 | NaMoO$_4$ | 2.4 | 24.3 | 39.8 | 33.3 | 0 |
| 30 | 2e | NR-36 | NaMoO$_4$ | 79.8 | 13.5 | 2.6 | 1.8 | 2.1 |
| 31 | 2a | NR-4 | V$_2$O$_5$ | 0 | 59.3 | 28.2 | 12.5 | 0 |
| 32 | 2b | NR-4 | V$_2$O$_5$ | 0 | 66.5 | 19.2 | 14.3 | 0 |
| 33 | 2c | NR-4 | V$_2$O$_5$ | 0 | 58.3 | 6.2 | 35.4 | 0 |
| 34 | 2d | NR-4 | V$_2$O$_5$ | 0 | 81.1 | 12.5 | 6.3 | 0 |
| 35 | 2e | NR-4 | V$_2$O$_5$ | 1.9 | 65.3 | 28.5 | 4.2 | 0 |
| 36 | 2a | NR-36 | V$_2$O$_5$ | 0 | 29.5 | 18.1 | 52.4 | 0 |
| 37 | 2b | NR-36 | V$_2$O$_5$ | 0 | 13.5 | 5.2 | 81.3 | 0 |
| 38 | 2c | NR-36 | V$_2$O$_5$ | 0 | 1.9 | 8.1 | 89.9 | 0 |
| 39 | 2d | NR-36 | V$_2$O$_5$ | 0 | 24.3 | 3.1 | 72.6 | 0 |
| 40 | 2e | NR-36 | V$_2$O$_5$ | 1.6 | 74.5 | 15.8 | 3.9 | 4.2 |
| 41 | 2a | NR-4 | CoCl$_2$ | 1.1 | 3.8 | 91.3 | 3.7 | 0 |
| 42 | 2b | NR-4 | CoCl$_2$ | 9.3 | 39 | 20.4 | 31.3 | 0 |
| 43 | 2c | NR-4 | CoCl$_2$ | 4.6 | 23.2 | 12.1 | 60 | 0 |
| 44 | 2d | NR-4 | CoCl$_2$ | 0 | 6.2 | 88.8 | 4.9 | 0 |
| 45 | 2e | NR-4 | CoCl$_2$ | 83.1 | 13.6 | 1.1 | 2.1 | 0 |
| 46 | 2a | NR-36 | CoCl$_2$ | 0.9 | 4.3 | 66.9 | 27.8 | 0 |
| 47 | 2b | NR-36 | CoCl$_2$ | 0 | 15.9 | 6.5 | 77.5 | 0 |
| 48 | 2c | NR-36 | CoCl$_2$ | 0 | 0 | 9.3 | 90.7 | 0 |
| 49 | 2d | NR-36 | CoCl$_2$ | 0 | 0.8 | 20.9 | 78.2 | 0 |
| 50 | 2e | NR-36 | CoCl$_2$ | 79.9 | 15.1 | 2.6 | 2.4 | 0 |

$^a$Uncorrected values

Figure 1B:
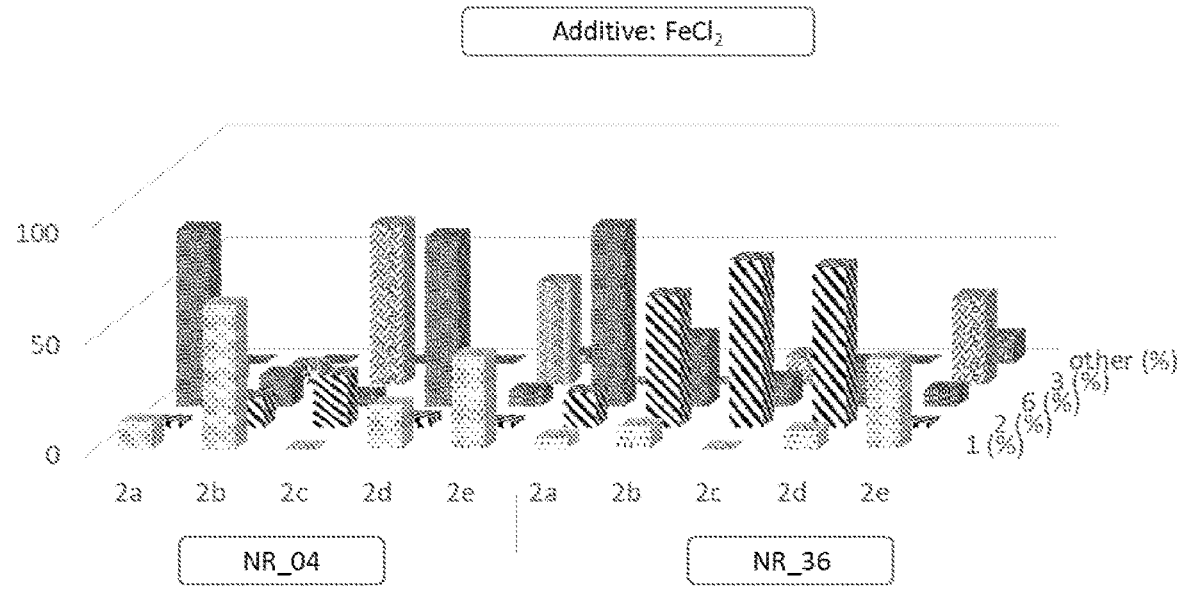
Figure 1C:
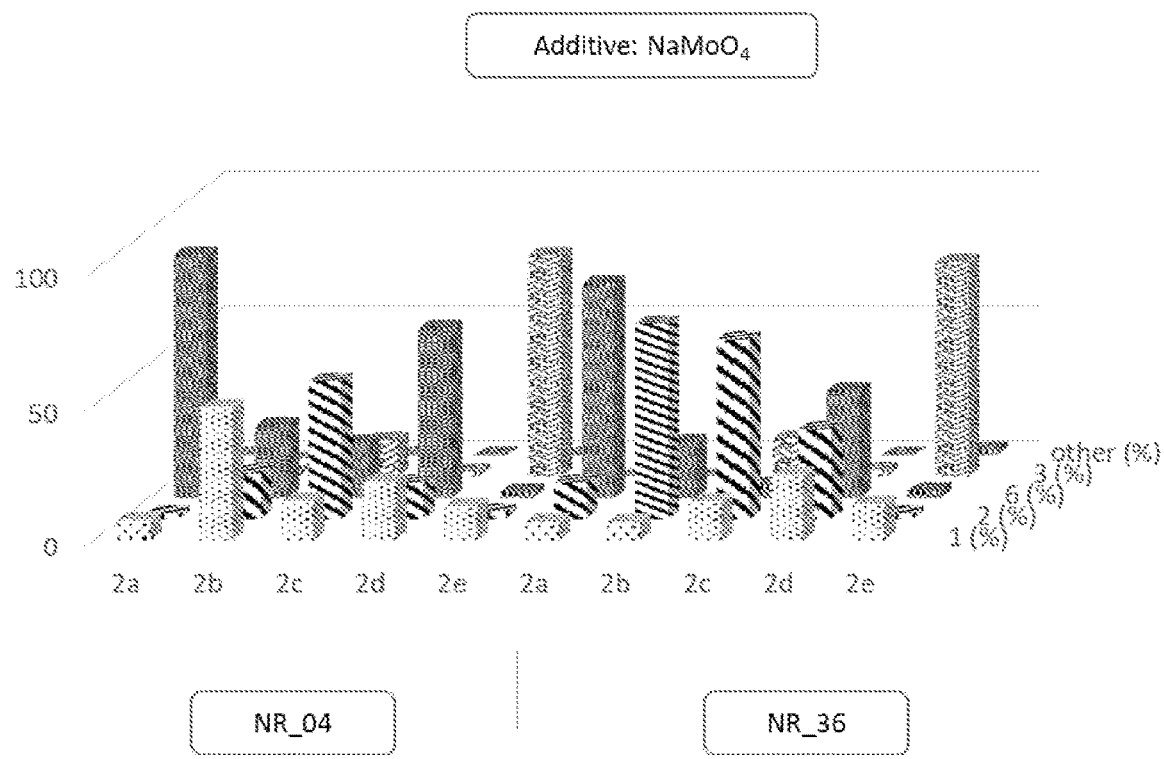
Figure 1D:
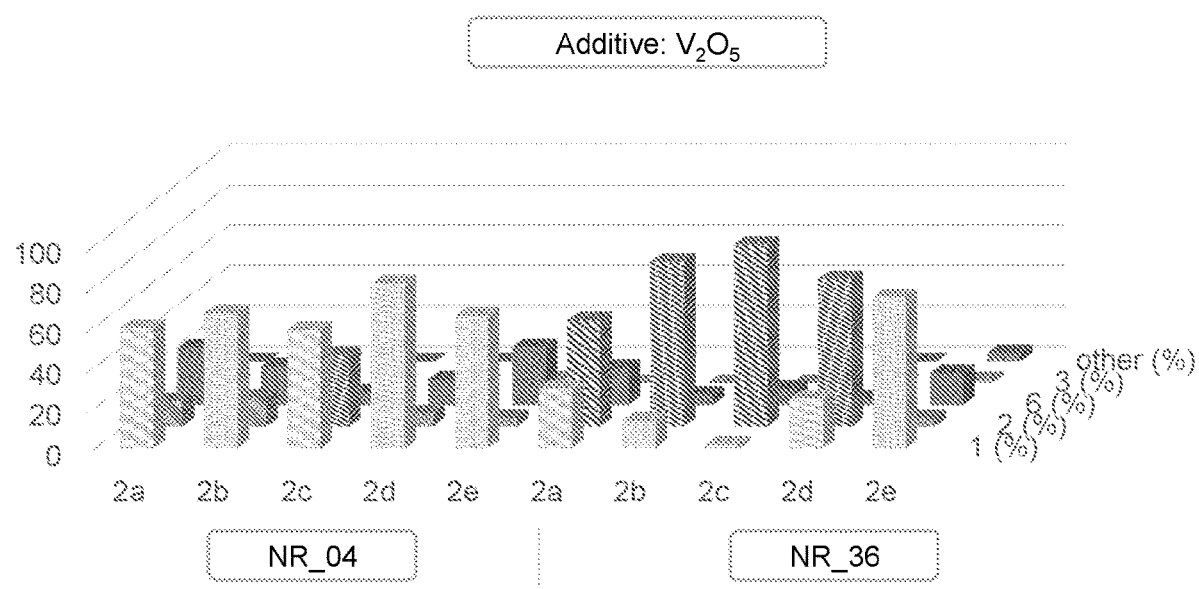

The screening of various metal additives showed that the disproportionation of the hydroxylamines intermediates is strongly dependant of the enzyme/metal additive combination. In general, higher amounts of amine products are obtained in presence of vanadium (V) oxide and enzyme NR-4, while the same metal with enzyme NR-36 appears to result in much lower substrate conversion, the final reaction mixtures containing significant amounts of non-converted nitro substrates (FIG. 1D).

Figure 1E:
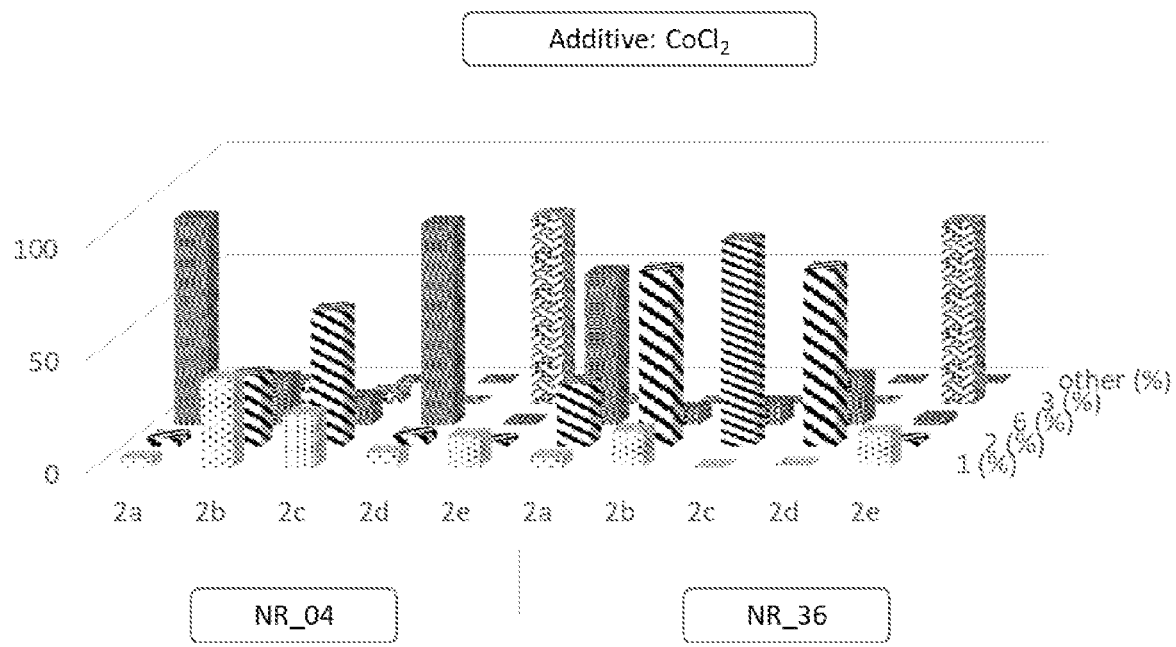

Substrate 2b shows relatively good conversions with all the metals investigated, while its regioisomer 2a prefers V$_2$O$_5$ as the best metal additive. In addition, the reaction containing substrate 2a contains large amounts of the azoxy intermediate 6a, with modest amounts of non-converted starting material, suggesting that the disproportionation of the hydroxylamine is slow when metal additives other than vanadium are used (FIG. 1B, 1C, 1E). The challenging sterically substrate 2d gives similar conversions to the corresponding amine 1d in presence of either CuCl$_2$ or V$_2$O$_5$, while the simple nitrobenzene 2e shows significant amounts of hydroxylamine intermediate present when using CoCl$_2$, NaMoO$_4$ or FeCl$_2$ additives.

Substrate Spectrum Study

Screening of the nitroreductase collection identified four nitroreductases (NR-4, NR-14, NR-17, NR-24) with broad substrate and metal additive tolerance. This group of enzymes was used for investigating an expanded substrate panel, shown below.

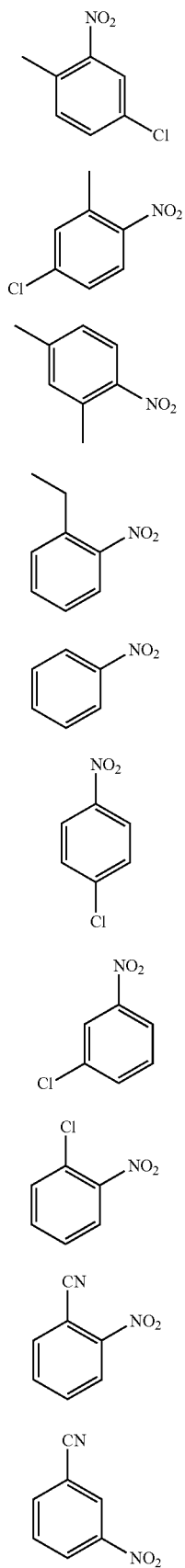
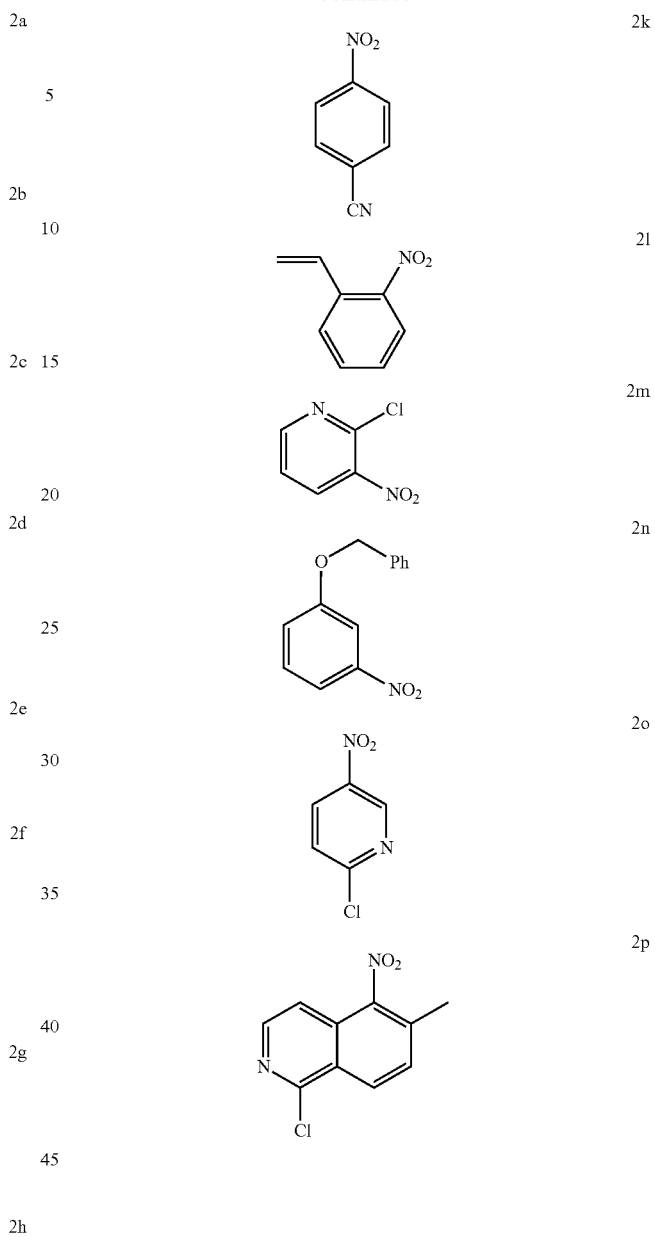

Each reaction contained 325 μL of buffer 250 mM potassium phosphate (pH 6.0; 7.0 or 8.0)+1 mM NADP+ and 1 mM NAD+, 100 mM D-glucose, 1 mg/mL GDH+5 mg/mL NR enzyme+25 μL substrate 2 solution (0.4 M in MTBE, final concentration of substrate 20 mM)+50 μL $V_2O_5$ (20 mM stock, final concentration 2 mM). The reactions were shaken at 35° C. for 18 hours. The reactions were quenched with ACN (1 mL), vortexed and centrifuged. Samples were then collected and analysed by HPLC. For the reactions without the metal additive, the amount of master mix (buffer, cofactor, GDH, glucose) was 375 μL, with all the other components identical as above.

Substrate Spectrum Study—Ortho-Methyl and Chloro Groups (2a and 2b)

The results of the nitroreduction of substrates 2a and 2b are presented in Table 7 and Table 8.

TABLE 7

Nitroreduction of substrate 2a

| Example | Nitro (2) | Enzyme | V$_2$O$_5$ | 3 | 1 | 5 | 4 | 6 | 2 | Other |
|---|---|---|---|---|---|---|---|---|---|---|
| 1 | 2a | NR-4 | 0 | 0 | 4.3 | nd | Nd | 95.2 | 0.5 | 0 |
| 2 | 2a | NR-14 | 0 | 0 | 0.7 | nd | Nd | 87.3 | 12 | 0 |
| 3 | 2a | NR-17 | 0 | 0 | 12.1 | nd | Nd | 87.2 | 0.7 | 0 |
| 4 | 2a | NR-24 | 0 | 0 | 1.6 | nd | Nd | 97.9 | 0.7 | 0 |
| 5 | 2a | NR-4 | 2 | 0 | 76.1 | nd | Nd | 18.8 | 1.2 | 3.8 |
| 6 | 2a | NR-14 | 2 | 0 | 22.1 | nd | Nd | 12.2 | 65.3 | 0 |
| 7 | 2a | NR-17 | 2 | 0 | 70 | nd | Nd | 17.3 | 12.7 | 0 |
| 8 | 2a | NR-24 | 2 | 0 | 70.1 | nd | Nd | 26 | 1.9 | 1.9 |

$^a$Uncorrected values

TABLE 8

Nitroreduction of substrate 2b

| Example | Nitro (2) | Enzyme | V$_2$O$_5$ | 3 | 1 | 5 | 4 | 6 | 2 | Other |
|---|---|---|---|---|---|---|---|---|---|---|
| 1 | 2b | NR-4 | 0 | 0 | 3.2 | nd | Nd | 95.7 | 1.1 | 1 |
| 2 | 2b | NR-14 | 0 | 0 | 0.8 | nd | Nd | 27.5 | 70.6 | 0 |
| 3 | 2b | NR-17 | 0 | 0 | 9.8 | nd | Nd | 87.2 | 2.9 | 0 |
| 4 | 2b | NR-24 | 0 | 0 | 4.3 | nd | Nd | 93.7 | 1.9 | 0 |
| 5 | 2b | NR-4 | 2 | 0 | 48.9 | nd | Nd | 46.2 | 4.9 | 0 |
| 6 | 2b | NR-14 | 2 | 0 | 5.7 | nd | Nd | 9.1 | 85.2 | 0 |
| 7 | 2b | NR-17 | 2 | 0 | 26.1 | nd | Nd | 16.8 | 57.1 | 0 |
| 8 | 2b | NR-24 | 2 | 0 | 46.4 | nd | Nd | 46.7 | 6.9 | 0 |

$^a$Uncorrected values

Figure 2A:
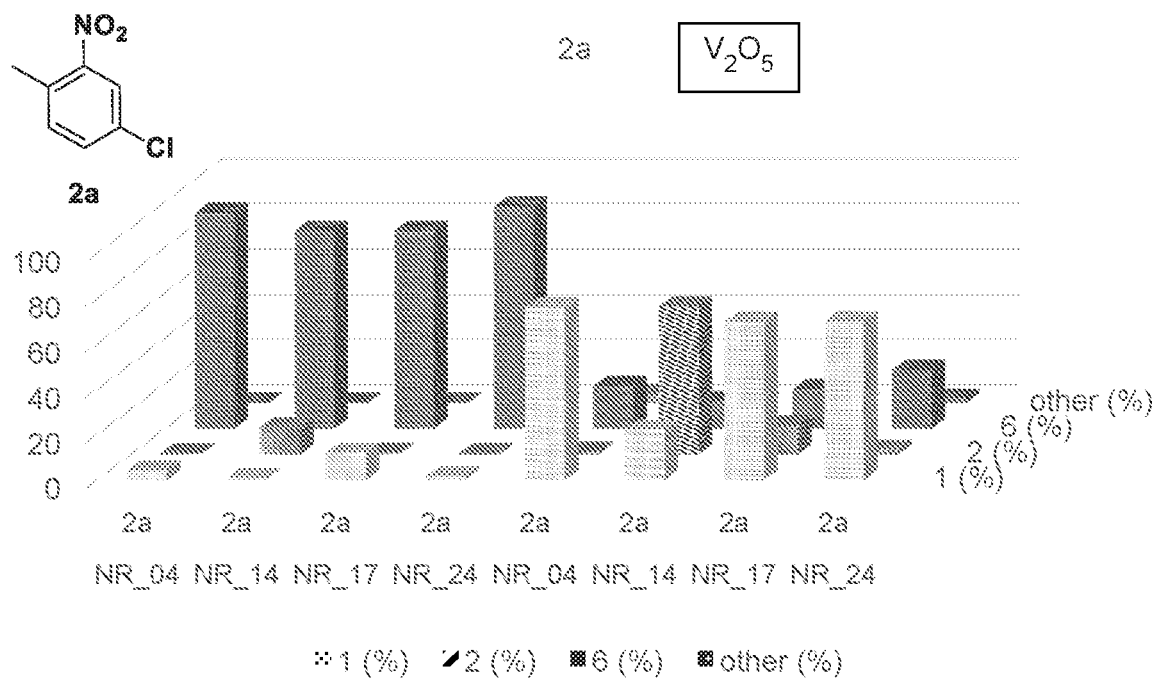
FIGS. 2A-B show percentage conversion of example ortho-substituted substrates to their corresponding products using a catalyst comprising a nitroreductase (NR-4, NR-14, NR-17, NR-24) and vanadium (V) oxide ($V_2O_5$): (A) substrate 2a and (B) substrate 2b.
Figure 2B:
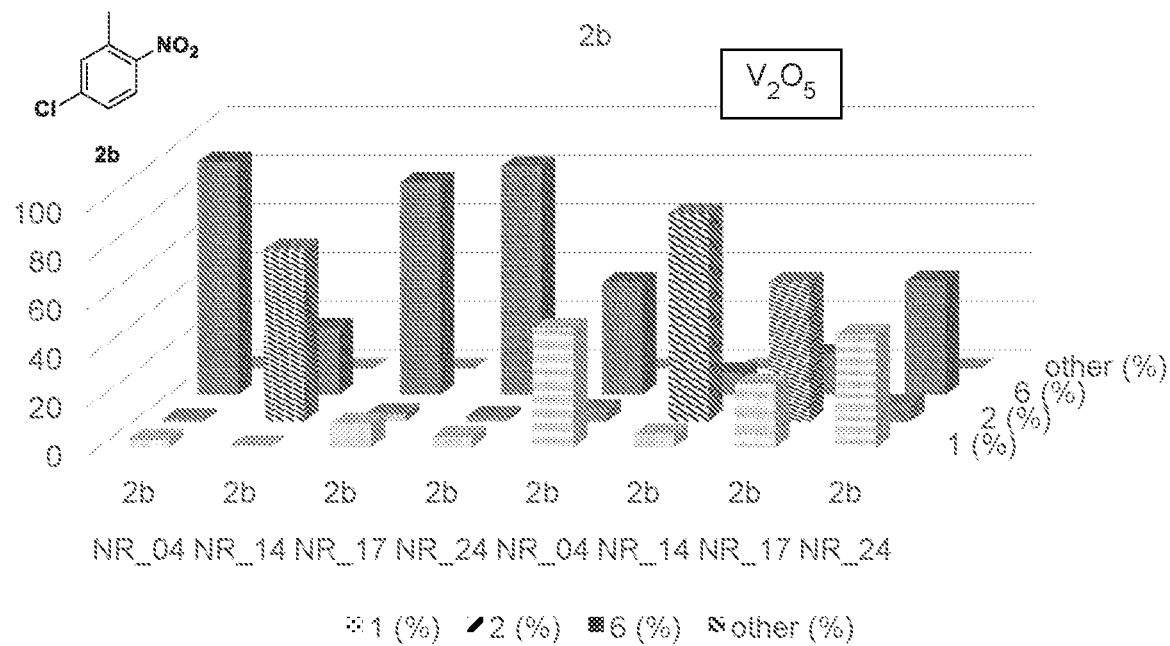

The substrates 2a and 2b presented several challenges to the biocatalysed nitroreduction reaction. These substrates have a methyl group in ortho position from the nitro group, providing a certain degree of steric hindrance and a halogen atom, responsible for electronic effects on the ring. Our results on substrates 2a and 2b suggest that the position of the halogen could influence the reaction outcome; a slightly larger amount of amine is formed when the Cl atom is in meta position rather than in the para position, however, this effect should be investigated further (FIG. 2A-C).

The most active enzyme appears to be NR-4, which consistently displays the highest activity on a very broad range of substrates. In contrast, NR-14 does not appear to accept very well these type of compounds, showing a very modest activity. Interestingly, no dechlorination is observed. The azoxy intermediate formed remains significant even in the presence of vanadium additive and a screening of different other metal additives failed to show an improvement on the vanadium results.

Substrate Spectrum Study—Ortho-Alkyl Groups (2c, 2d and 2e)

The results of the nitroreduction of substrates 2c, 2d and 2e are presented in Table 9, Table 10 and Table 11.

TABLE 9

Nitroreduction of substrate 2c

| Example | Nitro (2) | Enzyme | V$_2$O$_5$ (mM) | 3 (%)$^a$ | 1 (%)$^a$ | 6 (%)$^a$ | 2 (%)$^a$ | Other (%) |
|---|---|---|---|---|---|---|---|---|
| 1 | 2c | NR-4 | 0 | 84.5 | 4.1 | 8.8 | 0.4 | 0 |
| 2 | 2c | NR-14 | 0 | 63.1 | 5.3 | 22.4 | 7.6 | 0 |
| 3 | 2c | NR-17 | 0 | 74.2 | 1.8 | 22.4 | 0.2 | 0 |
| 4 | 2c | NR-24 | 0 | 82.1 | 1.9 | 13.7 | 2.2 | 0 |
| 5 | 2c | NR-4 | 2 | 13.4 | 44.5 | 26.9 | 15.1 | 0 |
| 6 | 2c | NR-14 | 2 | 0 | 0 | 1.9 | 96.7 | 0 |
| 7 | 2c | NR-17 | 2 | 0 | 1.5 | 4.2 | 91.5 | 0 |
| 8 | 2c | NR-24 | 2 | 13.2 | 7.2 | 36.6 | 42.9 | 0 |

$^a$Uncorrected values

TABLE 10

Nitroreduction of substrate 2d

| Example | Nitro (2) | Enzyme | V$_2$O$_5$ (mM) | 3 (%)$^a$ | 1 (%)$^a$ | 6 (%)$^a$ | 2 (%)$^a$ | Other (%) |
|---|---|---|---|---|---|---|---|---|
| 1 | 2d | NR-4 | 0 | 0 | 15.1 | 75.7 | 6.2 | 2.9 |
| 2 | 2d | NR-14 | 0 | 0 | 0.8 | 14.5 | 81.9 | 2.6 |
| 3 | 2d | NR-17 | 0 | 0 | 20.3 | 72.3 | 7.2 | 0 |
| 4 | 2d | NR-24 | 0 | 0 | 17.6 | 74.6 | 4.4 | 3.2 |
| 5 | 2d | NR-4 | 2 | 0 | 74.8 | 11.2 | 2.3 | 11.6 |
| 6 | 2d | NR-14 | 2 | 0 | 6.3 | 7.7 | 85.9 | 0 |
| 7 | 2d | NR-17 | 2 | 0 | 21.8 | 6.5 | 68.7 | 2.8 |
| 8 | 2d | NR-24 | 2 | 0 | 78.9 | 4.4 | 2.3 | 14.3 |

$^a$Uncorrected values

TABLE 11

Nitroreduction of substrate 2e

| Example | Nitro (2) | Enzyme | V$_2$O$_5$ (mM) | 3 (%)$^a$ | 1 (%)$^a$ | 6 (%)$^a$ | 2 (%)$^a$ | Other (%) |
|---|---|---|---|---|---|---|---|---|
| 1 | 2e | NR-4 | 0 | 0 | 16.8 | 78.7 | 3.2 | 1.4 |
| 2 | 2e | NR-14 | 0 | 0 | 6.1 | 72.1 | 6.9 | 14.9 |
| 3 | 2e | NR-17 | 0 | 0 | 28.7 | 67.5 | 3.8 | 0 |
| 4 | 2e | NR-24 | 0 | 0 | 20.8 | 70.5 | 2 | 6.4 |
| 5 | 2e | NR-4 | 2 | 0 | 64.2 | 6.7 | 0 | 20.8 |
| 6 | 2e | NR-14 | 2 | 0 | 63.7 | 9.7 | 0 | 26.5 |
| 7 | 2e | NR-17 | 2 | 0 | 64 | 7.7 | 0 | 23.1 |
| 8 | 2e | NR-24 | 2 | 0 | 71.9 | 11.6 | 0 | 16.4 |

$^a$Uncorrected values

The substrates 2c, 2d and 2e were chosen to investigate further the steric hindrance effect of a group in the ortho position to the nitro group. A previous screen of nitroreductases using 2-ethyl-nitrobenzene identified the enzymes NR-4, NR-17 and NR-24 as the only active biocatalysts for this substrate, with good conversions to the corresponding aniline.

Figure 3A:
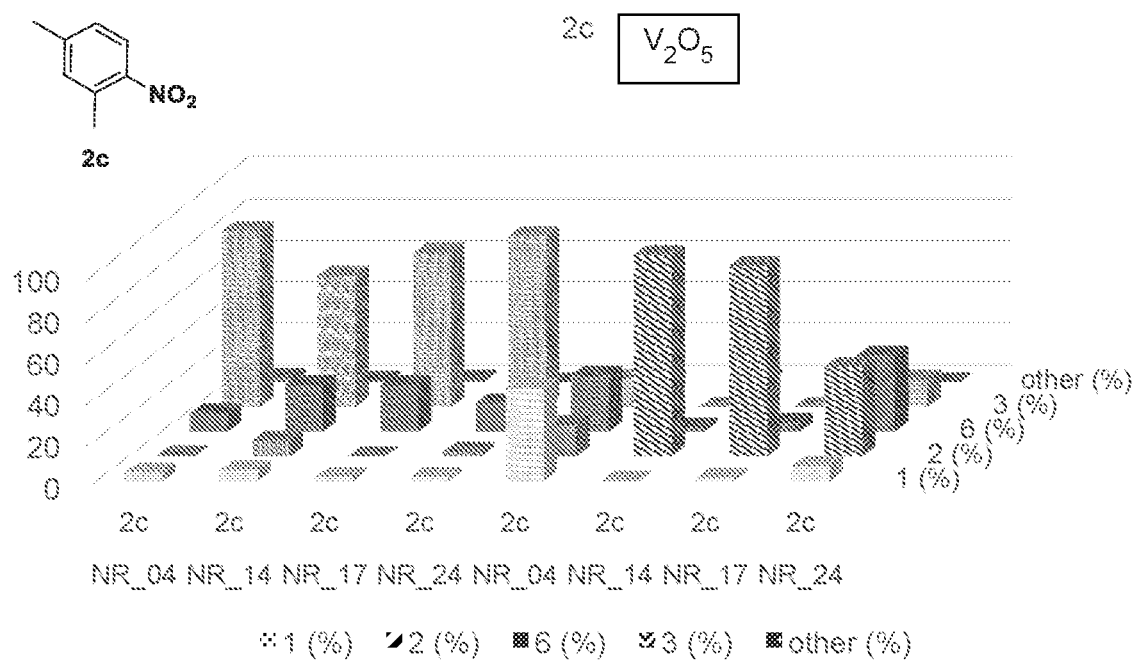
FIGS. 3A-C show percentage conversion of example orthoalkyl-substituted substrates to their corresponding products using a catalyst comprising a nitroreductase (NR-4, NR-14, NR-17, NR-24) and vanadium (V) oxide ($V_2O_5$): (A) substrate 2c; (B) substrate 2d and (C) substrate 2e.
Figure 3B:
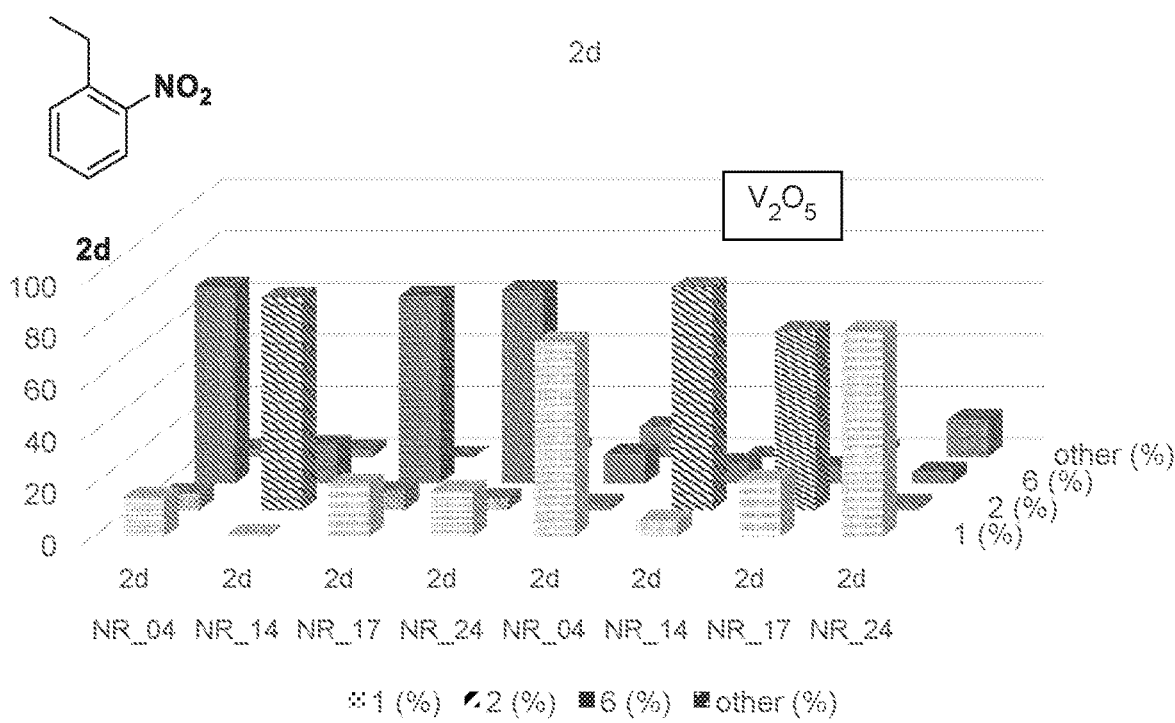
Figure 3C:
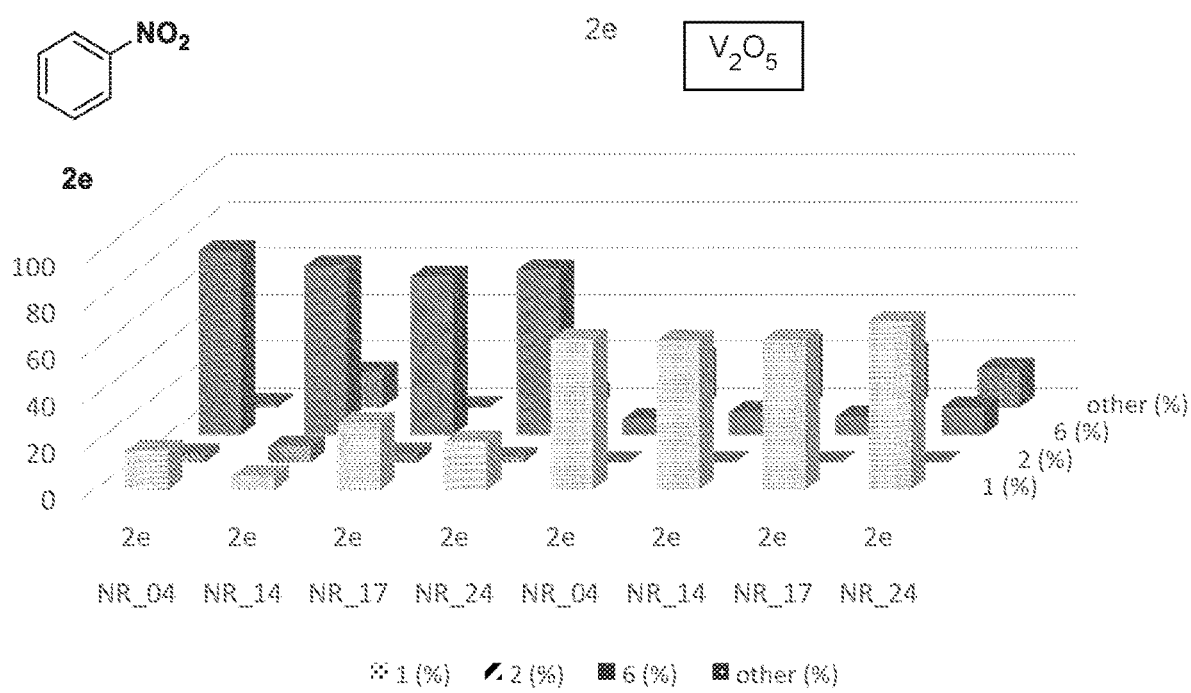

The 2,4-dimethyl-nitrobenzene substrate 2c showed a very interesting behaviour. Although it seems to be well-accepted by the enzymes and large amounts of hydroxylamine 3c is formed (see FIG. 3A-C), the addition of vanadium to the reaction appears to have a negative impact on the starting material conversion. In particular, reactions catalysed by enzymes NR-14 and NR-17 results in little to no conversion of the nitro compound.

Substrate Spectrum Study—Vinyl Group (2l)

The results of the nitroreduction of substrate 2l is presented in Table 13.

TABLE 12

Nitroreduction of substrate 2l

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2l | NR-4  | 0 | 0 | 46.2 | 53  | 0.7 | 0   |
| 2 | 2l | NR-14 | 0 | 0 | 34.2 | 59.2| 1.7 | 4.8 |
| 3 | 2l | NR-17 | 0 | 0 | 93.4 | 3.9 | 0.6 | 1.9 |
| 4 | 2l | NR-24 | 0 | 0 | 53.8 | 42.5| 1.2 | 2.4 |
| 5 | 2l | NR-4  | 2 | 0 | 95.9 | 0   | 2.2 | 1.8 |
| 6 | 2l | NR-14 | 2 | 0 | 91.5 | 0.6 | 6.6 | 1.2 |
| 7 | 2l | NR-17 | 2 | 0 | 95.7 | 0   | 4.3 | 0   |
| 8 | 2l | NR-24 | 2 | 0 | 96.8 | 0   | 3.2 | 0   |

[a]Uncorrected values

Figure 4A:
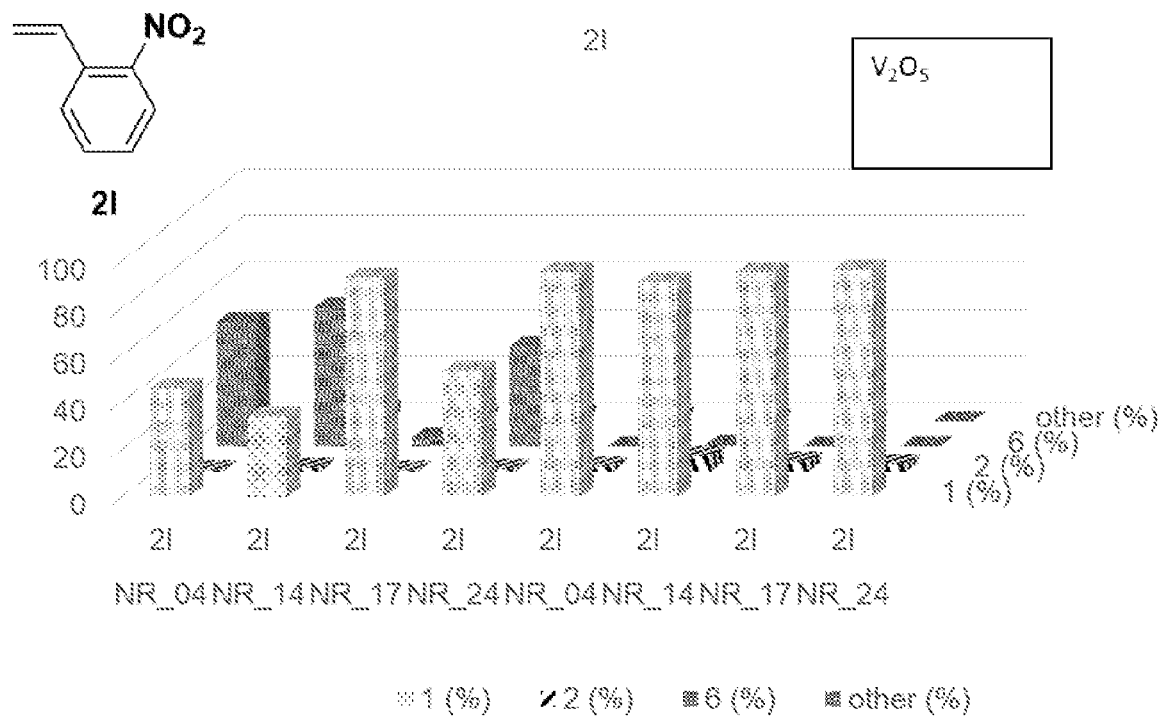
FIG. 4A shows percentage conversion of example vinyl-substituted substrate 2l to the corresponding product using a catalyst comprising a nitroreductase (NR-4, NR-14, NR-17, NR-24) and vanadium (V) oxide ($V_2O_5$).

Competitive reduction of aliphatic double bonds was investigated using 3-vinyl-nitrobenzene 2l. The substrate was very well tolerated by the enzymes, with only traces of non-converted material detected at the end of reaction (FIG. 4A).

When the vanadium salt was added, the conversions to the amine product reached values of over 90%, with minimum side-products and no evidence of double bond reduction. The presence of significant amounts of amine in the reactions without vanadium additive could be explained by a faster disproportionation of the hydroxylamine intermediate.

Substrate Spectrum Study-Chloro Group (2f, 2g and 2h)

The results of the nitroreduction of substrates 2f, 2g and 2h are presented in Table 13, Table 14 and Table 15.

TABLE 13

Nitroreduction of substrate 2f

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2f | NR-4  | 0 | 91.3 | 7.0 | 0   | 1.7 | 0 |
| 2 | 2f | NR-14 | 0 | 90.3 | 0.8 | 7.1 | 1.7 | 0 |
| 3 | 2f | NR-17 | 0 | 89.1 | 3.2 | 5.8 | 1.9 | 0 |
| 4 | 2f | NR-24 | 0 | 90.6 | 0.8 | 5.9 | 2.6 | 0 |
| 5 | 2f | NR-4  | 2 | 0 | 98.7 | 0 | 1.2 | 0 |
| 6 | 2f | NR-14 | 2 | 0 | 98.8 | 0 | 1.1 | 0 |
| 7 | 2f | NR-17 | 2 | 0 | 98.8 | 0 | 1.1 | 0 |
| 8 | 2f | NR-24 | 2 | 0 | 99   | 0 | 1   | 0 |

[a]Uncorrected values

TABLE 14

Nitroreduction of substrate 2g

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2g | NR-4  | 0 | 94.6 | 0.9 | 3.8 | 0.5 | 0 |
| 2 | 2g | NR-14 | 0 | 94.1 | 1.2 | 2.5 | 1.1 | 0 |
| 3 | 2g | NR-17 | 0 | 92.7 | 3.4 | 3.8 | 1.2 | 0 |
| 4 | 2g | NR-24 | 0 | 95.1 | 0   | 3.6 | 1.1 | 0 |
| 5 | 2g | NR-4  | 2 | 0 | 99   | 0 | 1   | 0 |
| 6 | 2g | NR-14 | 2 | 0 | 99.8 | 0 | 0.2 | 0 |
| 7 | 2g | NR-17 | 2 | 0 | 99.5 | 0 | 0.5 | 0 |
| 8 | 2g | NR-24 | 2 | 0 | 98.8 | 0 | 1.2 | 0 |

[a]Uncorrected values

TABLE 15

Nitroreduction of substrate 2h

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2h | NR-4  | 0 | 63.8 | 2.4 | 31.9 | 1.9 | 0 |
| 2 | 2h | NR-14 | 0 | 66.4 | 2.5 | 28.3 | 2.7 | 0 |
| 3 | 2h | NR-17 | 0 | 60.9 | 4.8 | 34.3 | 0   | 0 |
| 4 | 2h | NR-24 | 0 | 74.7 | 3.1 | 22.3 | 0   | 0 |
| 5 | 2h | NR-4  | 2 | 0 | 99   | 0 | 0 | 1   |
| 6 | 2h | NR-14 | 2 | 0 | 98.9 | 0 | 0 | 1.1 |
| 7 | 2h | NR-17 | 2 | 0 | 98.9 | 0 | 0 | 1.1 |
| 8 | 2h | NR-24 | 2 | 0 | 98.8 | 0 | 0 | 1.2 |

[a]Uncorrected values

Figure 5A:
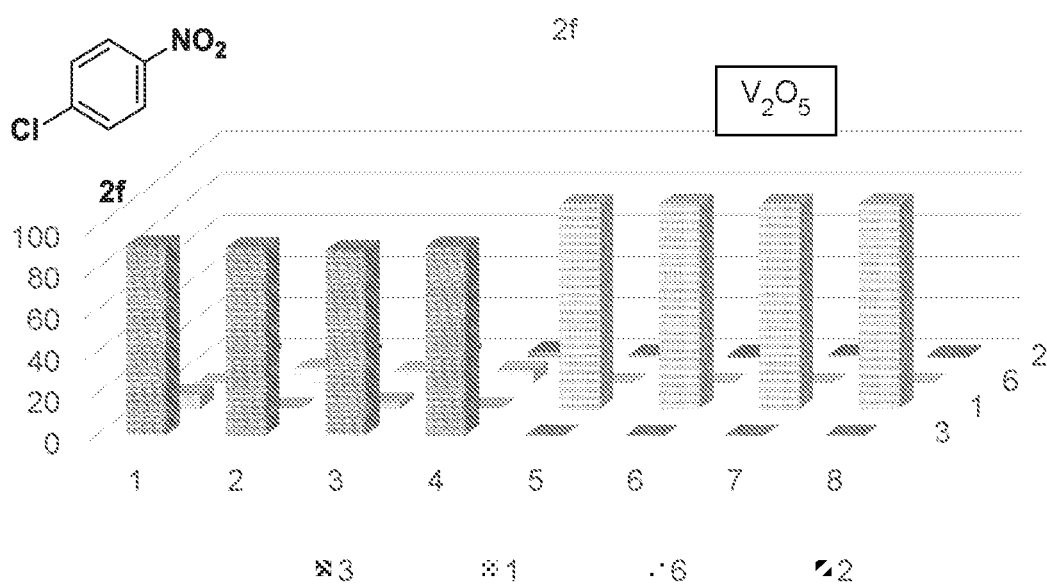
FIGS. 5A-C show percentage conversion of example chloro-containing substrates to their corresponding products using a catalyst comprising a nitroreductase (NR-4, NR-14, NR-17, NR-24) and vanadium (V) oxide ($V_2O_5$): (A) substrate 2f; (B) substrate 2g and (C) substrate 2h.
Figure 5B:
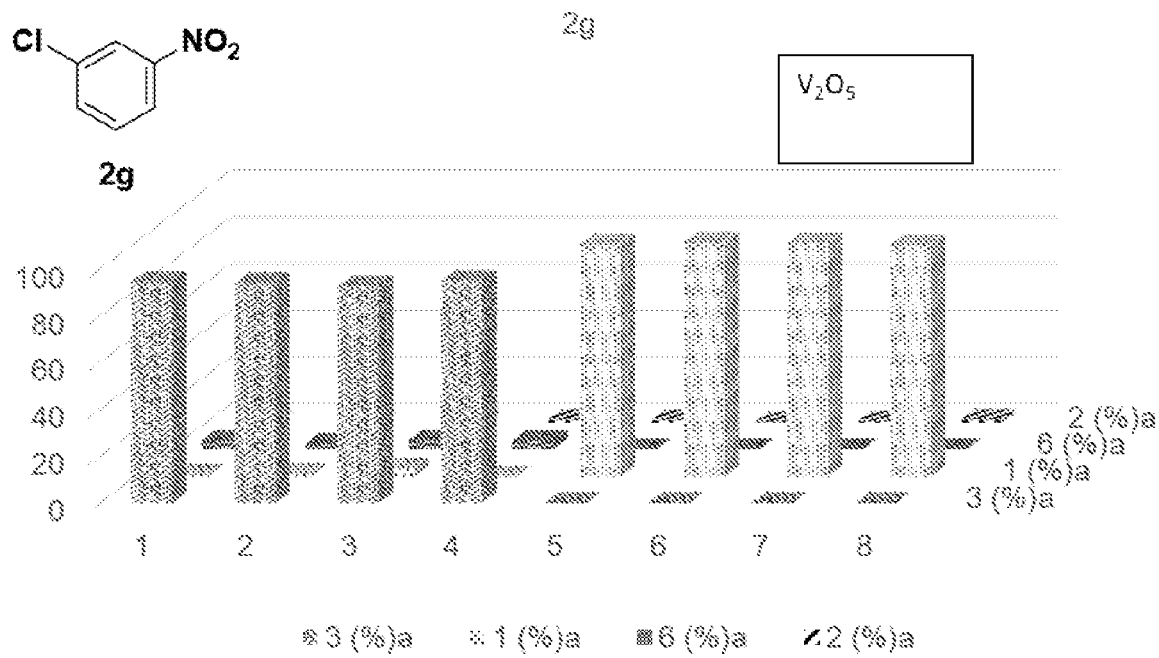
Figure 5C:
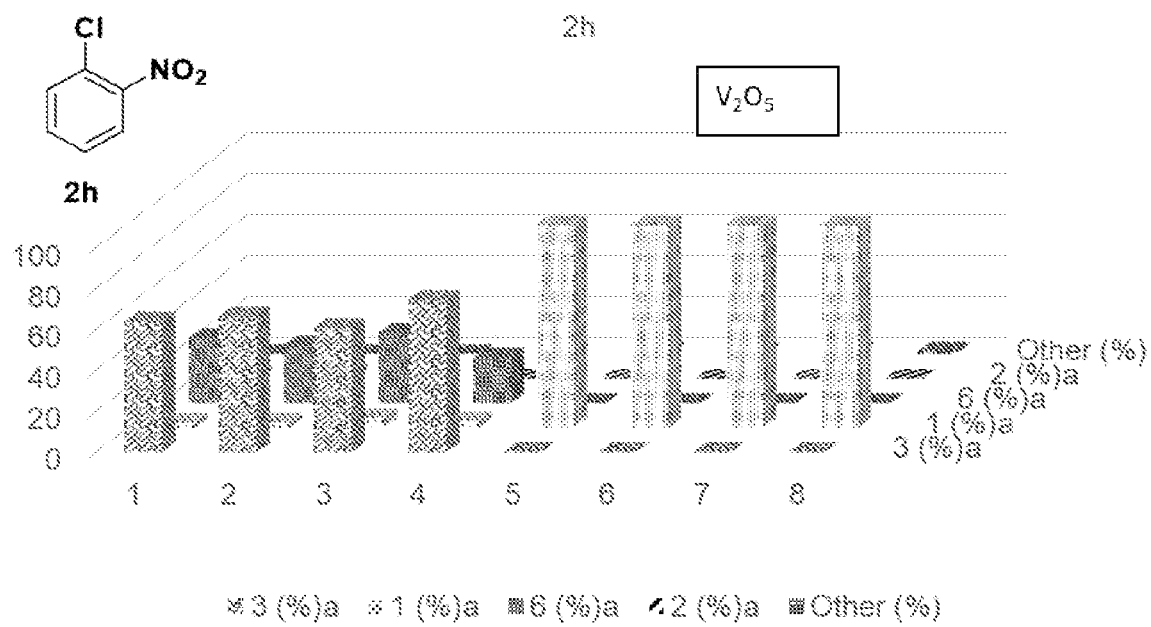

The simple chloro-nitrobenzenes 2f, 2g and 2h were well-accepted by the enzymes tested and no de-chlorination was observed (FIG. 5A-C). The addition of vanadium to the reaction resulted in completely chemoselective and almost quantitative conversions to the corresponding anilines.

Substrate Spectrum Study-Nitrile Group (2j and 2k)

The results of the nitroreduction of substrates 2j and 2k are presented in Table 16 and Table 17.

TABLE 16

Nitroreduction of substrate 2j

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2j | NR-4  | 0 | 0 | 2.7 | 88.5 | 0   | 8.8 |
| 2 | 2j | NR-14 | 0 | 0 | 1.3 | 93.6 | 1.7 | 3.2 |
| 3 | 2j | NR-17 | 0 | 0 | 6.2 | 88.1 | 0.7 | 5   |
| 4 | 2j | NR-24 | 0 | 0 | 3.3 | 88.1 | 0   | 8.5 |
| 5 | 2j | NR-4  | 2 | 0 | 73.8 | 16.5 | 0 | 9.6 |
| 6 | 2j | NR-14 | 2 | 0 | 79.1 | 16.8 | 0 | 4.1 |
| 7 | 2j | NR-17 | 2 | 0 | 79   | 15.7 | 0 | 5.3 |
| 8 | 2j | NR-24 | 2 | 0 | 72.9 | 18.4 | 0 | 8.6 |

[a]Uncorrected values

TABLE 17

Nitroreduction of substrate 2k

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2k | NR-4  | 0 | 0 | 5   | 94.9 | 0 | 0    |
| 2 | 2k | NR-14 | 0 | 0 | 0   | 98   | 0 | 2    |
| 3 | 2k | NR-17 | 0 | 0 | 3.6 | 96.4 | 0 | 0    |
| 4 | 2k | NR-24 | 0 | 0 | 0   | 96   | 0 | 4    |
| 5 | 2k | NR-4  | 2 | 0 | 89.1 | 0   | 0   | 10.3 |
| 6 | 2k | NR-14 | 2 | 0 | 94.5 | 2.1 | 3.3 | 0    |
| 7 | 2k | NR-17 | 2 | 0 | 93.8 | 1.3 | 2.9 | 1.8  |
| 8 | 2k | NR-24 | 2 | 0 | 85.9 | 2.2 | 0   | 11.8 |

[a]Uncorrected values

Figure 6A:
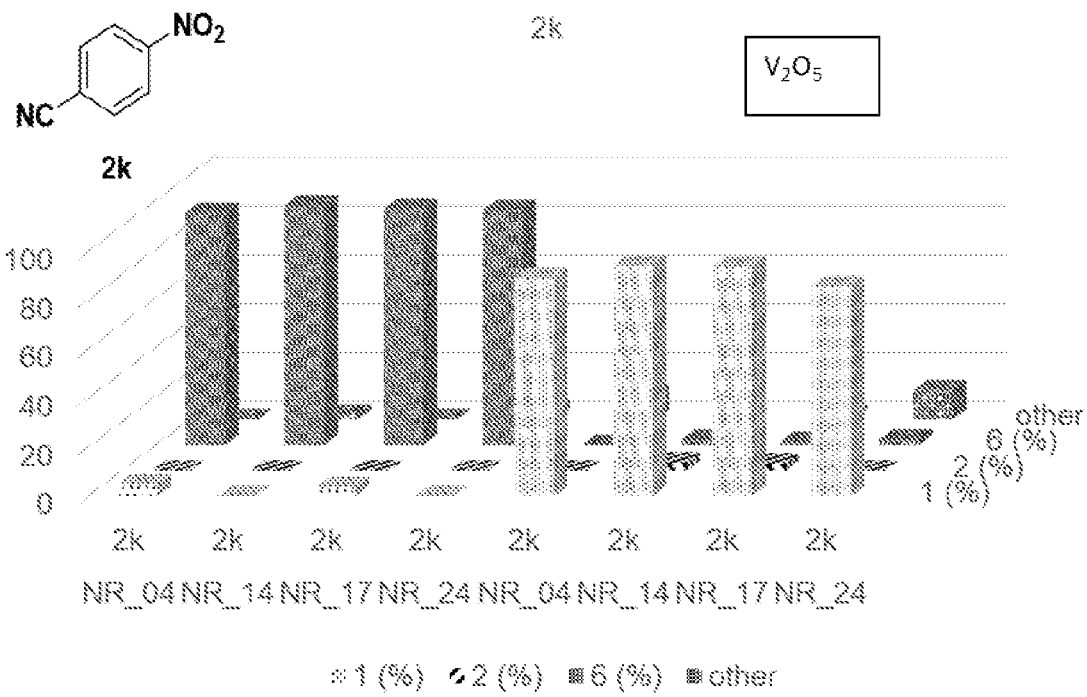
FIGS. 6A-B show percentage conversion of nitrile-substituted substrates to their corresponding products using a catalyst comprising a nitroreductase (NR-4, NR-14, NR-17, NR-24) and vanadium (V) oxide ($V_2O_5$): (A) substrate 2k and (B) substrate 2j.
Figure 6B:
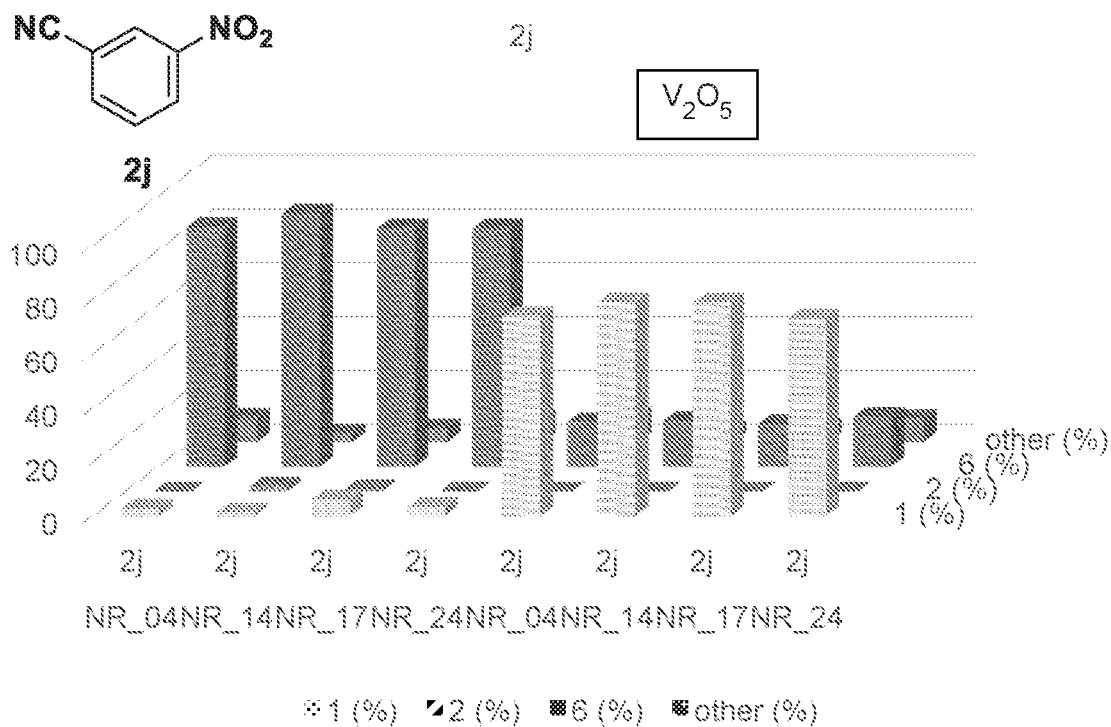

The nitriles 2j and 2k were also well accepted by the enzymes, again with minimum amounts of side products formed (FIG. 6A-B). No reduction of the nitrile group has been observed.

Substrate Spectrum Study-Nitropyridines (2m and 2o)

The results of the nitroreduction of substrates 2m and 2o are presented in Table 18 and

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2m | NR-4 | 0 | 97.3 | 2.7 | 0 | 0 | 0 |
| 2 | 2m | NR-14 | 0 | 83.7 | 4.2 | 0 | 0 | 12.1 |
| 3 | 2m | NR-17 | 0 | 86.7 | 7 | 0 | 0 | 6.3 |
| 4 | 2m | NR-24 | 0 | 88.9 | 4.3 | 0 | 0 | 6.6 |
| 5 | 2m | NR-4 | 2 | 0 | 88.3 | 6.5 | 0 | 5.1 |
| 6 | 2m | NR-14 | 2 | 0 | 90.4 | 6.9 | 0 | 2.6 |
| 7 | 2m | NR-17 | 2 | 0 | 92.3 | 0 | 0 | 7.7 |
| 8 | 2m | NR-24 | 2 | 0 | 90.7 | 0 | 0 | 9.3 |

[a]Uncorrected values

Table 19.

TABLE 18

Nitroreduction of substrate 2m

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2m | NR-4 | 0 | 97.3 | 2.7 | 0 | 0 | 0 |
| 2 | 2m | NR-14 | 0 | 83.7 | 4.2 | 0 | 0 | 12.1 |
| 3 | 2m | NR-17 | 0 | 86.7 | 7 | 0 | 0 | 6.3 |
| 4 | 2m | NR-24 | 0 | 88.9 | 4.3 | 0 | 0 | 6.6 |
| 5 | 2m | NR-4 | 2 | 0 | 88.3 | 6.5 | 0 | 5.1 |
| 6 | 2m | NR-14 | 2 | 0 | 90.4 | 6.9 | 0 | 2.6 |
| 7 | 2m | NR-17 | 2 | 0 | 92.3 | 0 | 0 | 7.7 |
| 8 | 2m | NR-24 | 2 | 0 | 90.7 | 0 | 0 | 9.3 |

[a]Uncorrected values

TABLE 19

Nitroreduction of substrate 2o

| Example | Nitro (2) | Enzyme | $V_2O_5$ (mM) | 4 (%)[a] | 1 (%)[a] | 6 (%)[a] | 2 (%)[a] | Other (%) |
|---|---|---|---|---|---|---|---|---|
| 1 | 2o | NR-4 | 0 | 93.1 | 6.9 | 0 | 0 | 0 |
| 2 | 2o | NR-14 | 0 | 82.6 | 17.4 | 0 | 0 | 0 |
| 3 | 2o | NR-17 | 0 | 78.4 | 21.6 | 0 | 0 | 0 |
| 4 | 2o | NR-24 | 0 | 78.3 | 21.7 | 0 | 0 | 0 |
| 5 | 2o | NR-4 | 2 | 0 | 91.1 | 0 | 0 | 8.8 |
| 6 | 2o | NR-14 | 2 | 0 | 91.4 | 8.5 | 0 | 0 |
| 7 | 2o | NR-17 | 2 | 0 | 96.4 | 0 | 0 | 3.7 |
| 8 | 2o | NR-24 | 2 | 0 | 90.4 | 0 | 0 | 9.5 |

[a]Uncorrected values

Figure 7A:
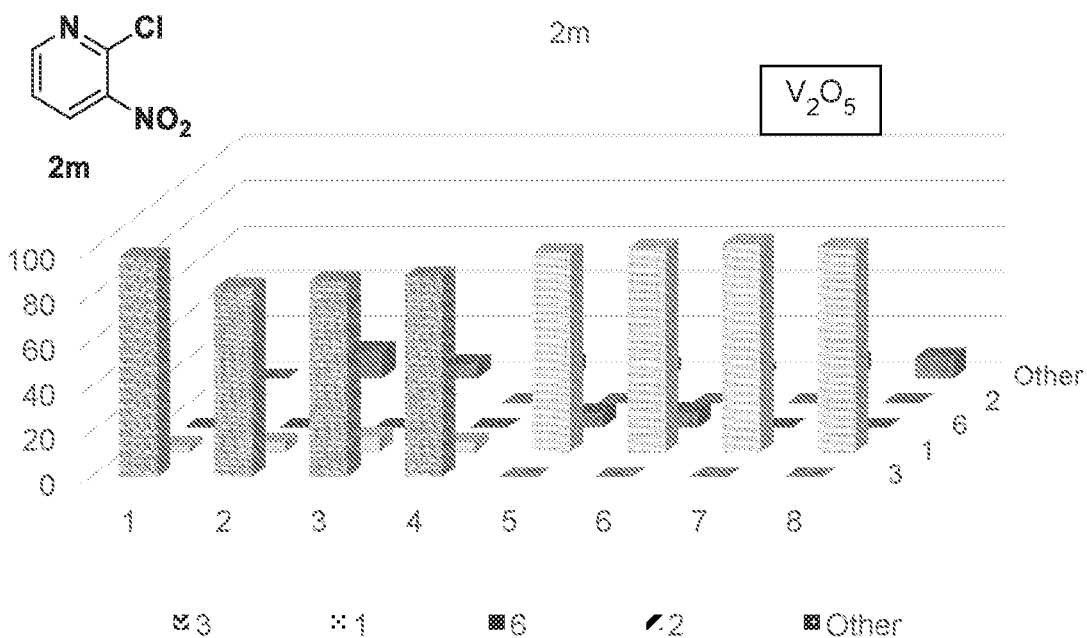
FIGS. 7A-B show percentage conversion of nitropyridine substrates to their corresponding products using a catalyst comprising a nitroreductase (NR-4, NR-14, NR-17, NR-24) and vanadium (V) oxide ($V_2O_5$): (A) substrate 2m and (B) substrate 2o.
Figure 7B:
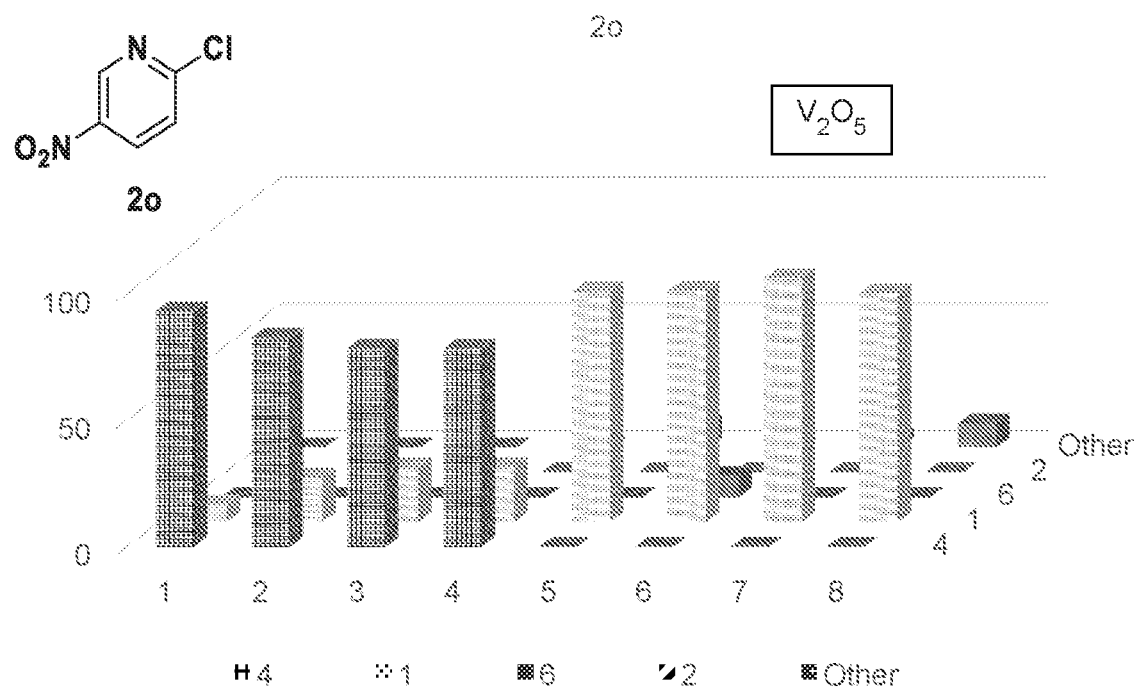
Figure 8A:
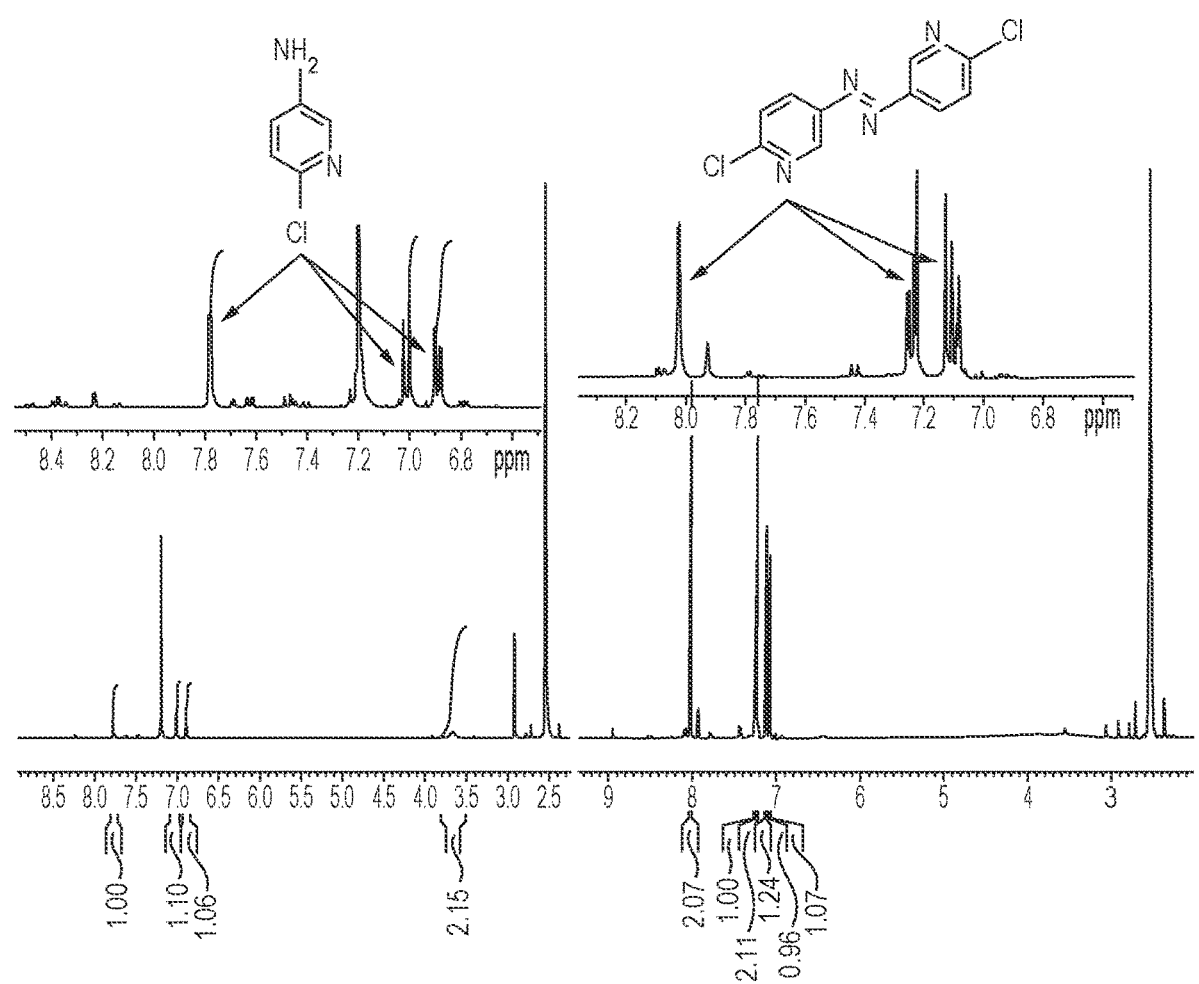
FIGS. 8A-B are 1H NMR of the conversion of nitropyridine substrates to their corresponding products using a catalyst comprising (left) a nitroreductase and vanadium (V) oxide ($V_2O_5$) or (right) a nitroreductase alone: (A) substrate 2m and (B) substrate 2o.
Figure 8B:
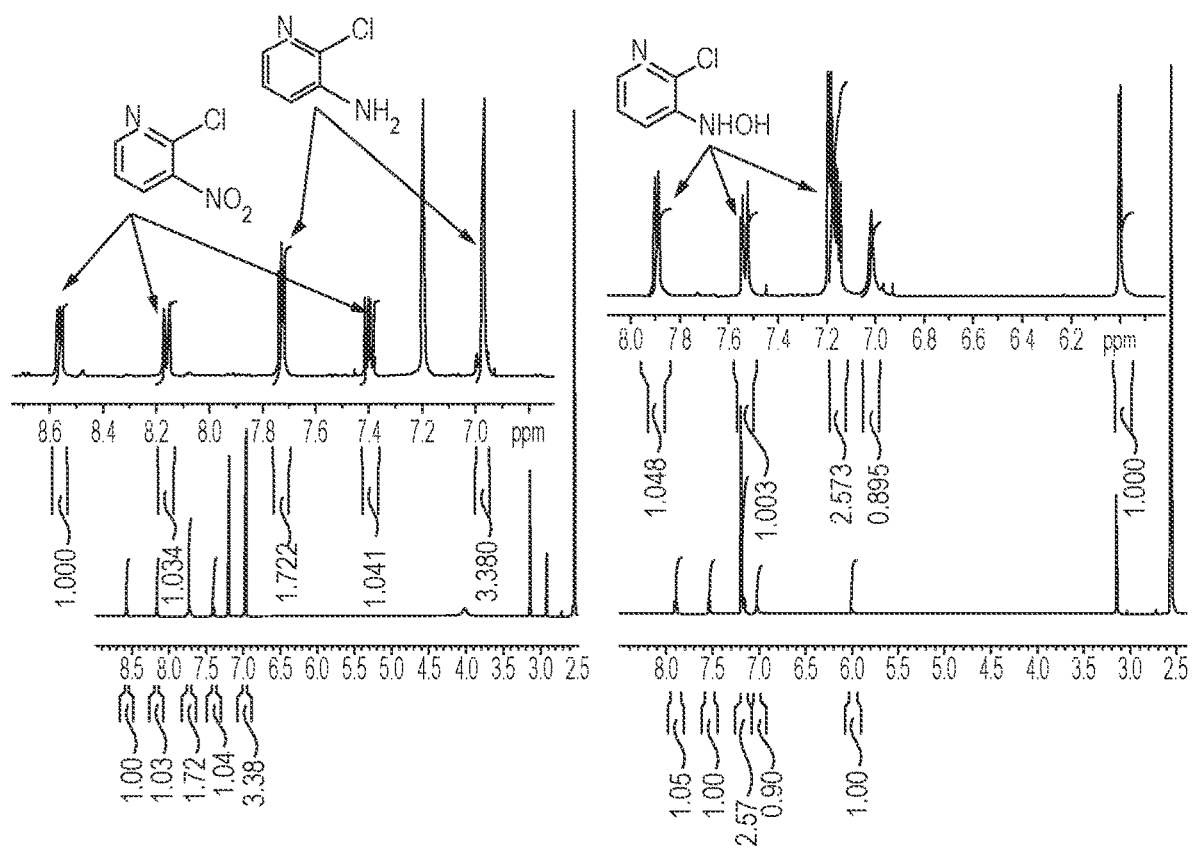

The nitropyridines 2m and 2o were readily reduced to the corresponding anilines in good yields, with minimal side product formed (FIG. 7A-B). As noted above, no dehydrochlorination or competitive reduction reactions were observed.

Substrate Spectrum Study—Benzyl Ether (2n)

Figure 10:
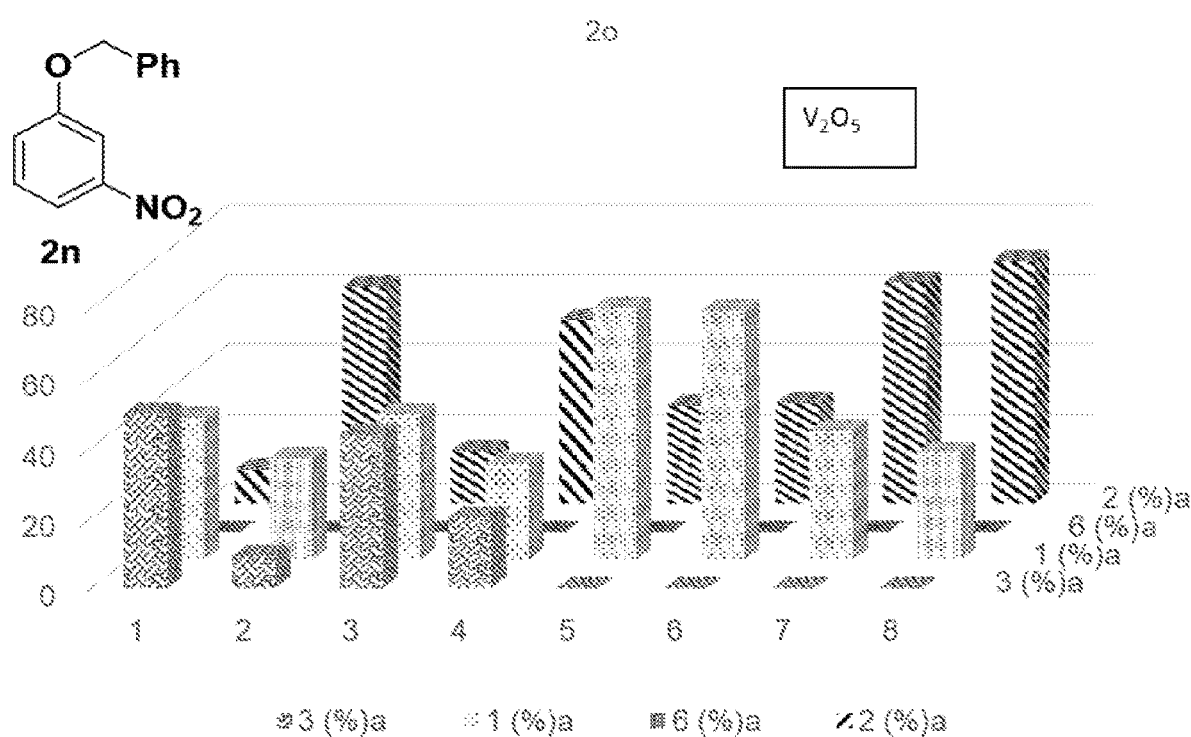
FIG. 10 shows percentage conversion of example benzyl ether substrate 2n to the corresponding product using a catalyst comprising a nitroreductase (NR-4, NR-14, NR-17, NR-24) and vanadium (V) oxide ($V_2O_5$).

The results of the nitroreduction of substrate 2n are presented in Table 20 and FIG. 10.

TABLE 20

Nitroreduction of substrate 2n

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2n | NR-4 | 0 | 49.6 | 40.6 | 0 | 9.7 | 0 |
| 2 | 2n | NR-14 | 0 | 9 | 29 | 0 | 62 | 0 |
| 3 | 2n | NR-17 | 0 | 43.5 | 41.5 | 0 | 15 | 0 |
| 4 | 2n | NR-24 | 0 | 20 | 27.3 | 0 | 52.6 | 0 |
| 5 | 2n | NR-4 | 2 | 0 | 72.1 | 0 | 27.9 | 0 |
| 6 | 2n | NR-14 | 2 | 0 | 71.4 | 0 | 28.6 | 0 |
| 7 | 2n | NR-17 | 2 | 0 | 36.9 | 0 | 63.1 | 0 |
| 8 | 2n | NR-24 | 2 | 0 | 30.6 | 0 | 69.4 | 0 |

[a]Uncorrected values

The benzyl 3-nitrophenyl ether 2n was accepted moderately well by NR-4 and NR-14, with conversions of over 70% to the corresponding anilines, in presence of vanadium salts. Significantly, the reduction was highly selective for the nitro group, with no debenzylated product observed.

Substrate Spectrum Study—Isoquinoline (2p)

The results of the nitroreduction of substrate 2p is presented in Table 21.

TABLE 21

Nitroreduction of substrate 2p

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2p | NR-4 | 0 | 0 | 66.4 | 0 | 33.6 | 0 |
| 2 | 2p | NR-14 | 0 | 0 | 0 | 0 | 100 | 0 |
| 3 | 2p | NR-17 | 0 | 0 | 0.7 | 0 | 99.3 | 0 |
| 4 | 2p | NR-24 | 0 | 0 | 0 | 0 | 100 | 0 |
| 5 | 2p | NR-4 | 2 | 0 | 21.7 | 0 | 78.3 | 0 |
| 6 | 2p | NR-14 | 2 | 0 | 0 | 0 | 100 | 0 |
| 7 | 2p | NR-17 | 2 | 0 | 0 | 0 | 100 | 0 |
| 8 | 2p | NR-24 | 2 | 0 | 0 | 0 | 100 | 0 |

[a]Uncorrected values

Figure 9A:
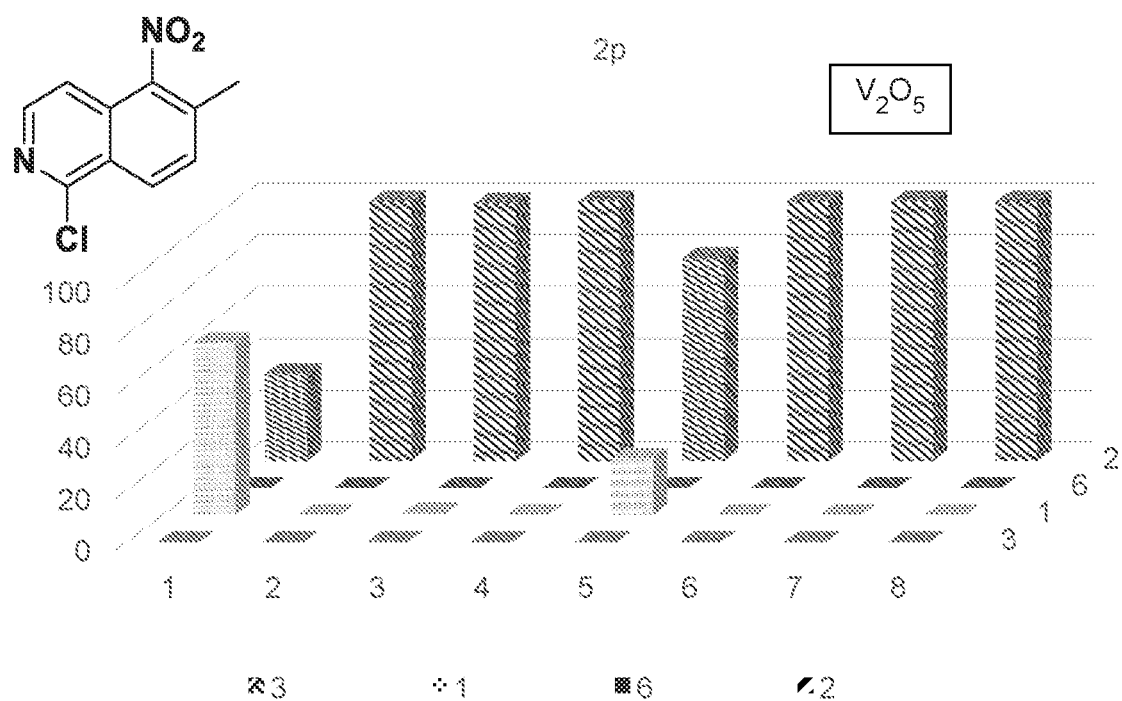
FIG. 9A shows percentage conversion of example isoquinoline substrate 2p to the corresponding product using a catalyst comprising a nitroreductase (NR-4, NR-14, NR-17, NR-24) and vanadium (V) oxide ($V_2O_5$).

The nitro-isoquinoline derivative 2p was tested in the same conditions, however the biocatalyzed reaction yielded disappointing results. Only NR-4_showed limited conversion of the starting material to the amine 1p (FIG. 9A).

The use of vanadium did not improve the reaction outcome. The results can be partially explained by the very poor solubility of the substrate and also by its bulkiness, which makes it difficult to fit in the enzyme's active site.

In this condition, the experiments were carried out using substrate in a 10 mM concentration:

Experimental protocol: Nitrochloroisoquinoline 2p (17.7 mg, 0.08 mmoles, final concentration 20 mM) were dissolved in 0.4 mL DMSO and added to the reaction mixture (4 mL) containing NR-4 5 mg/mL, NADP$^+$1 mM, NAD$^+$, GDH 1 mg/mL and glucose 100 mM, in phosphate buffer pH 7. The reaction mixture was stirred at 35° C. for 20h, after which it was extracted in DCM (2×5 mL), washed with brine (1×10 mL) and concentrated in vacuo to obtain a dark yellow powder (33.9 mg).

In order to optimise the reactions towards synthesis of the desired products, additional nitroreductases were screened as shown in Table. Due to the very poor solubility of the substrate 2p, the reactions were performed on a 10 mM substrate concentration scale, rather than 20 mM as previous substrates:

Experimental protocol: Each reaction contained 325 µL of buffer 250 mM potassium phosphate (pH 7)+1 mM NADP$^+$ and 1 mM NAD$^+$, 100 mM D-glucose, 1 mg/mL GDH+5 mg/mL NR enzyme+25 L substrate 2p solution (0.2 M in DMSO, final concentration of substrate 10 mM)+50 µL $V_2O_5$ (20 mM stock, final concentration 2 mM). The reactions were shaken at 35° C. for 18 hours. The reactions were quenched with ACN (1 mL), vortexed and centrifuged. Samples were then collected and analysed by HPLC. For the reactions without the metal additive, the amount of master mix (buffer, cofactor, GDH, glucose) was 375 µL, with all the other components identical as above.

TABLE 22

Screening of nitroreductases using 2p as substrate

| Example | Nitro (2) | Enzyme | $V_2O_5$ (mM) | 3 (%)[a] | 1 (%)[a] | 6 (%)[a] | 2 (%)[a] | Other (%) |
|---|---|---|---|---|---|---|---|---|
| 1 | 2p | NR-4 | 0 | nd | 75.9 | nd | 8.1 | 15.9 |
| 2 | 2p | NR-17 | 0 | nd | 10.5 | nd | 89.5 | 0 |
| 3 | 2p | NR-20 | 0 | nd | 83.1 | nd | 0.5 | 16.3 |
| 4 | 2p | NR-23 | 0 | nd | 23.2 | nd | 76.8 | 0 |
| 5 | 2p | NR-24 | 0 | nd | 10.1 | nd | 89.8 | 0 |
| 6 | 2p | NR-4 | 2 | nd | 77.5 | nd | 22.5 | 15.9 |
| 7 | 2p | NR-17 | 2 | nd | 0.7 | nd | 99.3 | 0 |
| 8 | 20 | NR-20 | 2 | nd | 12.5 | nd | 87.5 | 10.7 |
| 9 | 2p | NR-23 | 2 | nd | 1.2 | nd | 98.8 | 0 |
| 10 | 2p | NR-24 | 2 | nd | 2.5 | nd | 97.5 | 0 |

[a]Uncorrected values

Interestingly, a couple of other enzymes showed decent activity on this substrate, mainly NR-17, NR-23 and NR-24, in addition to NR-4. The nitroreductase NR-20 showed an impressive conversion of 83% conversion to the amine, with only traces of starting material detected during analysis. However, both NR-4 and NR-20 show some side-product accounting for approximately 15% of the mass balance.

Figure 9B:
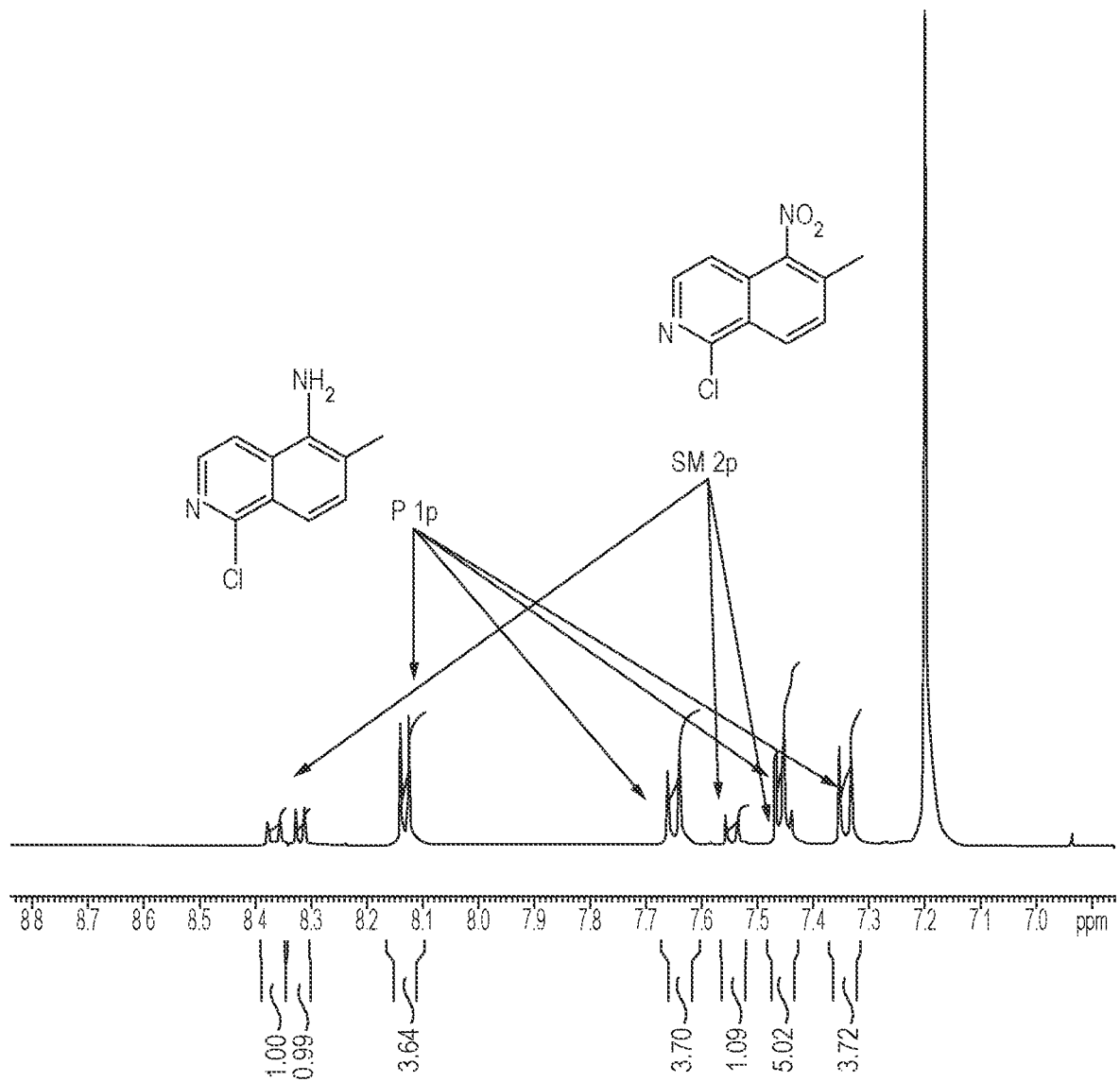
FIG. 9B is a 1H NMR of the reaction mixture for the example using a catalyst comprising NR-4 as nitroreductase.

Compared to the initial scaled up reaction, NR-4 shows a much better conversion on the small scale in presence on vanadium additive, which was confirmed by the $^1$HNMR analysis (FIG. 9B).

REFERENCES

A number of publications are cited above in order to more fully describe and disclose the invention and the state of the art to which the invention pertains. Full citations for these references are provided below. The entirety of each of these references is incorporated herein.

Boymans et al., 2015, "A study on the selective hydrogenation of nitroaromatics to N-arylhydroxylamines using a supported Pt nanoparticle catalyst" Catal. Sci. Technol., Vol. 5, pp. 176-83.
Corma and Serna, 2006, "Chemoselective Hydrogenation of Nitro Compounds with Supported Gold Catalysts", Science, Vol. 313, pp. 332-334.
Gallagher et al., 2012, "The Development of a Scalable, Chemoselective Nitro Reduction", Org. Process Res. Dev., Vol. 16, pp. 1665-1668.
Haber, 1898, Elektrochem. Angew. Phys. Chem., Vol. 22, pp. 506.
Hoogenraad at al., 2004, "Accelerated Process Development of Pharmaceuticals: Selective Catalytic Hydrogenations of Nitro Compounds Containing Other Functionalities", Org. Process Res. Dev., Vol. 8, pp. 469-476.
Kadam et al., 2015, "Advancement in methodologies for reduction of nitroarenes", RSC Adv., Vol. 5, pp. 83391-83407.
Kasparian et al., 2011, "Selective Catalytic Hydrogenation of Nitro Groups in the Presence of Activated Heteroaryl Halides" J. Org. Chem., Vol. 76, pp. 9841-9844.
Miller et al., 2018, "Informing Efforts to Develop Nitroreductase for Amine Production", Molecules Vol. 23, pp. 211.
Orlandi et al., 2016, "Recent Developments in the Reduction of Aromatic and Aliphatic Nitro Compounds to Amines", Org. Process Res. Dev., Vol. 22, pp. 430-445.
Pitsawong et al., 2014, "Understanding the Broad Substrate Repertoire of Nitroreductase Based on Its Kinetic Mechanism", J. Biol. Chem., Vol. 289, pp. 15203-15214
Studer et al., 2000, "Modulating the hydroxylamine accumulation in the hydrogenation of substituted nitroarenes using vanadium-promoted RNi catalysts", Topics in Catalysis, Vol. 13, pp. 205-212.
Studer and Baumeister, 1996, "Process for the Catalytic Hydrogeneration of Aromatic Nitro Compounds", WO 96/36597 A1, published 21 Nov. 1996.
Toogood and Scrutton, 2002, "Discovery, Characterization, Engineering, and Applications of Ene-Reductases for Industrial Biocatalysis", ACS Catal., Vol. 8, pp. 3532-3549.
Williams and Bruce, 2002, "'New uses for an Old Enzyme'—the Old Yellow Enzyme family of flavoenzymes", Microbiology, Vol. 148, pp. 1607-1614.
Yanto et al., 2010, "Nitroreductase from Salmonella typhimurium: characterization and catalytic activity", Org. Biomol. Chem., Vol. 8, pp. 1826.

The invention claimed is:

1. A method of reducing an aromatic nitro compound comprising the step of:
    (i) contacting an aromatic nitro compound with a catalyst, wherein, the catalyst comprises:
        (a) disproportionation agent comprising a transition metal selected from vanadium, chromium, molybdenum, iron, nickel, cobalt, and copper;
        (b) a biocatalyst that is a nitroreductase, wherein the biocatalyst comprises a polypeptide having at least 70% sequence identity to SEQ ID NO: 1 [NR-4], SEQ ID NO:2 [NR-14], SEQ ID NO:3 [NR-17] or SEQ ID NO:4 [NR-24]; and
        (c) a co-substrate which provides hydride for the reduction.

2. The method of claim 1, wherein the disproportionation agent is selected from $CuCl_2$, $Cu(OAc)_2$, $CuO_2$, copper metal, $FeCl_2$, $FeCl_3$, $Fe(acac)_3$, $FeCl_2$, $FeSO_4$, iron metal, $NaMoO_4$, $NH_4VO_3$, $VOSO_4$, $V(acac)_3$, $V_2O_5$, vanadium metal, and $CoCl_2$.

3. The method of claim 1, wherein the biocatalyst is or comprises a polypeptide having the following motif (1)

(1)    A-x(3,4)-G-x-[ADEGQST]-x(4)-[ADEGNQST]-
       [AEGNQST]

wherein:
    x denotes any amino acid residue,
    x(n) denotes a segment consisting of any amino acid residues of length n;
    [ab] denotes a single residue selected from a or b; and
    amino acids are denoted by their single letter codes.

4. The method of claim 1, wherein the biocatalyst is or comprises a polypeptide having at least 9 amino acid residues that are identical to or represent a conservative substitution for those of SEQ ID NO: 1 [NR-4] at the positions corresponding to:
    15, 39, 40, 41, 42, 64, 65, 67, 112, 132, 135, 136, 138, 220, 224, 229, 230 of SEQ ID NO: 1 [NR-4].

5. The method of claim 1, wherein the biocatalyst is or comprises a polypeptide having at least 15 amino acid residues that are identical to or represent a conservative substitution for those of SEQ ID NO: 1 [NR-4] at the positions corresponding to:

13, 15, 38, 39, 40, 41, 42, 43, 64, 65, 67, 69, 104, 112, 132, 133, 134, 135, 136, 137, 138, 139, 172, 220, 221, 224, 225, 229, 230, 233 of SEQ ID NO: 1 [NR-4].

6. The method of claim 1, wherein the biocatalyst is or comprises a polypeptide having at least 70% similarity or identity to SEQ ID NO: 1 [NR-4] and having the following amino acids at the residues corresponding to the following positions in SEQ ID NO: 1 [NR-4]:

| | |
|---|---|
| 41 | [SIMVAHNTWL]; |
| 136 | [GSAN]; |
| 224 | [KATYFREGIQV]; |
| 229 | [SKRYAQCGHNTV]; |
| 230 | [RKYE], | wherein:

[ab] denotes a single residue selected from a or b; and amino acids are denoted by their single letter codes.

7. The method of claim 1, wherein the method is a method of reducing an aromatic nitro compound to produce an aromatic hydroxylamine compound or the method is a method of reducing an aromatic nitro compound to produce an aromatic amine compound.

8. The method of claim 1, further comprising the step(s) of:
   (i) isolating the product; and/or
   (ii) isolating the catalyst; and/or
   (iii) contacting the biocatalyst with a co-substrate.

9. The method of claim 8, wherein when the method comprises step (iii) the co-substrate is a cofactor, and optionally further comprising the step of regenerating the cofactor using a reduced cofactor regenerating system.

10. The method of claim 1, wherein the step of contacting the aromatic nitro compound with the catalyst comprises adding discreet portions of the aromatic nitro compound to the catalyst or continuously adding the aromatic nitro compound to the catalyst.

11. The method of claim 1, wherein the temperature is maintained in the range 0 to 100° C. and/or the pH is maintained in the range 3.0 to 9.0.

12. A kit comprising:
   (a) a disproportionation agent comprising a transition metal selected from vanadium, chromium, molybdenum, iron, nickel, cobalt, and copper;
   (b) a biocatalyst that is a nitroreductase, wherein the biocatalyst comprises a polypeptide having at least 70% sequence identity to SEQ ID NO: 1 [NR-4], SEQ ID NO:2 [NR-14], SEQ ID NO: 3 [NR-17] or SEQ ID NO:4 [NR-24]; and
   (c) a co-substrate which provides hydride for the reduction.

13. The method according to claim 1, wherein the co-substrate is a co-factor.

14. The method according to claim 1, wherein the co-substrate is a co-factor selected from NADH, and NADPH.

* * * * *

SEQUENCE LISTING

```
<160> NUMBER OF SEQ ID NOS: 23

<210> SEQ ID NO 1
<211> LENGTH: 245
<212> TYPE: PRT
<213> ORGANISM: Artificial Sequence
<220> FEATURE:
<223> OTHER INFORMATION: NR-4 (NCBI RefSeq: WP_003178951.1)

<400> SEQUENCE: 1

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Ile Asn Gly Gln Gln Val Thr Val
        35                  40                  45

Ile Thr Val Gln Asp Glu Glu Arg Lys Lys Lys Ile Ala Glu Leu Ala
```

```
            50                  55                  60
Gly Gly Gln Val Trp Ile Glu Gln Ala Pro Val Phe Leu Leu Phe Cys
 65                  70                  75                  80

Ala Asp Phe Asn Arg Ala Lys Ile Ala Leu Glu Lys Asn Gly Glu Thr
                 85                  90                  95

Leu Ala Ile Thr Asp Gly Met Glu Ser Val Leu Val Gly Ala Val Asp
                100                 105                 110

Ala Gly Ile Ala Leu Gly Thr Ala Thr Ala Ala Glu Ser Met Gly
                115                 120                 125

Leu Gly Thr Val Pro Ile Gly Ala Val Arg Gly Arg Ala Glu Glu Leu
                130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
                180                 185                 190

Leu Ile Asp Ala Tyr Asp Glu Ile Ser Glu Tyr Met Thr Lys Arg
                195                 200                 205

Thr Asn Gly Gln Glu Thr Arg Asn Trp Ser Gln Gly Ile Ser Ala Tyr
210                 215                 220

Tyr Asn Lys Val Tyr Tyr Pro His Ile Arg Glu Met Leu Glu Lys Gln
225                 230                 235                 240

Gly Phe Lys Leu Glu
                245

<210> SEQ ID NO 2
<211> LENGTH: 240
<212> TYPE: PRT
<213> ORGANISM: Artificial Sequence
<220> FEATURE:
<223> OTHER INFORMATION: NR-14 (NCBI RefSeq:WP_006881391.1)

<400> SEQUENCE: 2

Met Asn Ser Thr Ile Glu Thr Ile Leu Gly His Arg Ser Ile Arg Lys
 1               5                  10                  15

Phe Thr Pro Glu Pro Ile Glu His Glu Gln Leu Gln Thr Ile Ile Gln
                20                  25                  30

Ala Gly Leu Ala Ala Ser Ser Ser Met Leu Gln Val Val Ser Ile
                35                  40                  45

Ile Arg Val Thr Asp Ser Glu Lys Arg Lys Gln Leu Ala Glu Cys Ala
 50                  55                  60

Gly Asn Gln Ala Tyr Val Glu Ser Ala Ala Glu Phe Leu Val Phe Cys
 65                  70                  75                  80

Ile Asp Tyr Gln Arg His Ser Thr Ile Lys Pro Asp Val Gln Val Asp
                 85                  90                  95

Phe Thr Glu Leu Thr Leu Ile Gly Ala Val Asp Ser Gly Ile Met Ala
                100                 105                 110

Gln Asn Cys Leu Leu Ala Ala Glu Ser Met Gly Leu Gly Gly Val Tyr
                115                 120                 125

Ile Gly Gly Leu Arg Asn Asn Ala Ala Arg Val Asp Glu Ile Leu Ser
                130                 135                 140

Leu Pro Gly Asn Thr Ala Ile Leu Phe Gly Met Cys Leu Gly His Pro
145                 150                 155                 160

Asp Gln Asn Pro Glu Val Lys Pro Arg Leu Pro Ile Asp Val Ile Met
```

```
                        165                 170                 175
His Glu Asn Gln Tyr Gln Thr Leu Asn Leu Asp Thr Ile Gln Ala Tyr
            180                 185                 190

Asp Gln Ala Met Gln Asp Tyr Tyr Ala Asn Arg Ser Ser Asn Gln Lys
        195                 200                 205

Gln Ser Thr Trp Ser Gln Glu Val Thr Gly Lys Leu Thr Gly Glu Ser
    210                 215                 220

Arg Pro His Ile Leu Pro Tyr Leu Asn Ser Lys Gly Leu Ala Lys Arg
225                 230                 235                 240

<210> SEQ ID NO 3
<211> LENGTH: 254
<212> TYPE: PRT
<213> ORGANISM: Artificial Sequence
<220> FEATURE:
<223> OTHER INFORMATION: NR-17 (NCBI RefSeq: WP_003683965.1)

<400> SEQUENCE: 3

Met Leu His Asn Pro Val Val Asp Gln Ile Thr Asn His Arg Ser Ile
1               5                   10                  15

Arg Lys Phe Lys Asp Gln Thr Leu Thr Ala Glu Gln Leu Gln Thr Leu
            20                  25                  30

Tyr Ala Ala Ala Ser Gln Thr Ser Thr Ser Met Phe Met Gln Gln Phe
        35                  40                  45

Ser Ile Leu His Val Thr Asp Glu Lys Leu Arg Glu Gly Val Arg Asn
    50                  55                  60

Ile Ser Gly Gln Pro Tyr Ile Gly Ala Asn Gly Asp Leu Phe Val Phe
65                  70                  75                  80

Val Val Asp Leu Tyr Arg Asn Gln Gln Ile Arg Gln Leu Gly Lys
            85                  90                  95

Asp Asp Gly Arg Leu His Thr Asp Ile Phe Phe Gln Ala Val Glu
        100                 105                 110

Asp Thr Val Leu Ala Leu Gln Asn Phe Leu Thr Ala Ala Glu Ser Leu
        115                 120                 125

Gly Leu Gly Gly Val Val Leu Gly Ser Ile Lys Asp Asp Pro Ala Glu
    130                 135                 140

Leu Val Lys Val Leu Asn Met Pro Lys Met Thr Leu Pro Leu Leu Gly
145                 150                 155                 160

Leu Gln Val Gly Val Pro Asp Gln Glu Pro Gln Leu Lys Pro Arg Leu
            165                 170                 175

Pro Gln Asn Gln Ile Ala Phe Glu Asn His Tyr Pro Thr Asp Phe Lys
        180                 185                 190

Val Gly Asp Leu Lys Asp Tyr Asp Glu Val Val Thr Thr Tyr Tyr Asp
    195                 200                 205

Leu Arg Asp Ala Asn Arg Arg Ile Asp Ser Phe Thr Lys Gln Ile Ser
    210                 215                 220

Gly Ala Lys Leu Ala Val His Asp Thr Thr Arg Asp Lys Leu Ala Ala
225                 230                 235                 240

Thr Ile Gln Ala Gln Gly Met Ala Leu Asp Trp Gly Lys Asn
            245                 250

<210> SEQ ID NO 4
<211> LENGTH: 251
<212> TYPE: PRT
<213> ORGANISM: Artificial Sequence
<220> FEATURE:
<223> OTHER INFORMATION: NR-20
```

<400> SEQUENCE: 4

```
Met Asn Asp Met Asn Glu Val Leu Gln Leu Leu Thr Asp His Arg Ser
1               5                   10                  15

Ile Arg Ser Tyr Thr Asp Glu Pro Val Ser Asp Glu Gln Leu Asp Leu
            20                  25                  30

Ile Ile Gln Ala Ala Gln Ala Ala Pro Thr Ser Ile Asn Gly Gln Gln
        35                  40                  45

Phe Thr Val Ile Ala Val Lys Asp Lys Glu Arg Lys Lys Lys Ile Ser
    50                  55                  60

Glu Leu Ala Gly Gly Gln Pro Trp Ile Asp Gln Ala Pro Val Phe Leu
65              70                  75                  80

Leu Phe Cys Ala Asp Phe Asn Arg Ala Lys Ile Ala Leu Glu Glu Tyr
                85                  90                  95

Asn Asp Thr Pro Leu Glu Ile Thr Asn Gly Leu Glu Ser Val Leu Val
            100                 105                 110

Gly Ala Val Asp Val Gly Ile Ala Leu Gly Thr Ala Thr Ala Ala Ala
        115                 120                 125

Glu Ser Met Gly Leu Gly Thr Val Pro Ile Gly Ala Val Arg Gly Lys
130                 135                 140

Pro Asp Glu Leu Ile Glu Leu Leu Lys Leu Pro Lys Tyr Val Phe Pro
145                 150                 155                 160

Val Ser Gly Leu Val Ile Gly His Pro Ala Asp Arg Ser Ala Lys Lys
                165                 170                 175

Pro Arg Leu Pro Gln Ala Ala Val Leu His His Glu Thr Tyr Gln Glu
            180                 185                 190

Glu Asp Val Arg Thr His Ile Glu Ala Tyr Asp Lys Gln Met Ser Glu
        195                 200                 205

Tyr Met Lys Lys Arg Thr Asp Gly Gln Glu Thr Arg Asn Trp Ser Gln
210                 215                 220

Gly Ile Thr Ser Tyr Tyr Lys Gln Leu Tyr Tyr Pro His Ile Arg Glu
225                 230                 235                 240

Met Leu Glu Lys Gln Gly Phe Lys Thr Asp Lys
                245                 250
```

<210> SEQ ID NO 5
<211> LENGTH: 241
<212> TYPE: PRT
<213> ORGANISM: Artificial Sequence
<220> FEATURE:
<223> OTHER INFORMATION: NR-23 (NCBI RefSeq: WP_011705684.1)

<400> SEQUENCE: 5

```
Met Asn Pro Thr Leu Asp Leu Ile Leu Ala His Arg Ser Ile Arg Gln
1               5                   10                  15

Phe Thr Ala Glu Pro Ile Thr Asp Ile Gln Leu Asp Gln Ile Leu Ser
            20                  25                  30

Ala Ala Gln Ala Ala Ser Ser Ser Phe Leu Gln Ala Asn Ser Ile
        35                  40                  45

Ile Arg Val Thr Asp Lys Ala Leu Arg Ser Arg Leu Ala Glu Leu Ala
    50                  55                  60

Gly Tyr Gln Ala Tyr Val Ala Gln Ala Glu Phe Leu Leu Phe Cys
65              70                  75                  80

Ala Asp Tyr His Arg His Cys Glu Val Val Pro Asp Ala Gln Thr Gly
                85                  90                  95
```

Phe Val Glu Gln Leu Leu Ile Gly Ala Ile Asp Gly Ala Leu Met Ala
                100                 105                 110

Gln Asn Ala Leu Leu Ala Ala Gln Ser Met Gly Leu Gly Gly Val Tyr
            115                 120                 125

Ile Gly Gly Ile Arg Asn Asn Pro Ala Ala Val Ser Glu Ala Val Gly
        130                 135                 140

Leu Pro His Gln Val Ile Pro Leu Phe Gly Leu Cys Leu Gly His Pro
145                 150                 155                 160

Ala Gln Ala Pro Glu Gln Lys Pro Arg Leu Pro Arg Ala Leu Val Val
                165                 170                 175

His Glu Asn Arg Tyr Gln Thr Glu Leu Asp Arg Glu Leu Leu Ala Gly
            180                 185                 190

Tyr Asp Gln Gln Ile Glu Ala Tyr Tyr Gln Ser Arg Ser Ser Asn Asn
        195                 200                 205

Lys Gln Gln Ser Trp Ser Gly Gln Ile Arg Gly Ile Leu Gly Lys Glu
            210                 215                 220

Ala Arg Pro Phe Met Gln Asp Phe Leu Arg Ser Arg Gly Phe Asn Leu
225                 230                 235                 240

Lys

<210> SEQ ID NO 6
<211> LENGTH: 217
<212> TYPE: PRT
<213> ORGANISM: Artificial Sequence
<220> FEATURE:
<223> OTHER INFORMATION: NR-24 (NCBI RefSeq: WP_011135791.1

<400> SEQUENCE: 6

Met Asn Ile Ala His Tyr Ala Gln Thr Arg Tyr Thr Thr Lys Ala Phe
1               5                   10                  15

Asp Pro Gly Phe Arg Leu Ser Ala Gly Gln Ile Glu Gln Ile Glu Thr
            20                  25                  30

Leu Leu Arg His Ser Pro Ser Ser Thr Asn Ser Gln Pro Trp His Phe
        35                  40                  45

Phe Ile Ala Gly Ser Asp Glu Ser Lys Ala Arg Val Ala Lys Ala Thr
    50                  55                  60

Ala Asp Gly Tyr Ala Phe Asn Gln Ala Lys Val Leu Asn Ala Ser His
65                  70                  75                  80

Val Val Val Phe Cys Thr Arg Ala Ala Leu Asp Asp Ala Tyr Leu Arg
                85                  90                  95

Thr Leu Leu Asp Gln Glu Glu Arg Asp Gly Arg Phe Ala Ser Pro Glu
            100                 105                 110

Ala Arg Ala Gly Gln His Lys Gly Arg Ser His Phe Ala Asp Met His
        115                 120                 125

Arg Phe Glu Leu Arg Asp Ala Pro His Trp Met Glu Lys Gln Val Tyr
    130                 135                 140

Leu Ala Val Gly Thr Leu Leu Leu Gly Ala Ala Ala Leu Glu Ile Asp
145                 150                 155                 160

Ala Cys Pro Ile Glu Gly Phe Asp Gln Arg Thr Leu Gly Glu Glu Leu
                165                 170                 175

Gly Leu Arg Glu Lys Gly Leu Ile Ala Ser Val Ile Val Ala Leu Gly
            180                 185                 190

Arg Arg Ser Asp Glu Asp Phe Asn Ala Arg Leu Pro Lys Ser Arg Leu
        195                 200                 205

Pro Ala Glu Ala Val Ile Thr Arg Leu

<210> SEQ ID NO 7
<211> LENGTH: 201
<212> TYPE: PRT
<213> ORGANISM: Artificial Sequence
<220> FEATURE:
<223> OTHER INFORMATION: NR-31

<400> SEQUENCE: 7

```
Met Ser Lys Val Leu Val Leu Lys Ser Ser Ile Leu Ala Gly Tyr Ser
1               5                   10                  15

Gln Ser Asn Gln Leu Ser Asp Tyr Phe Val Glu Gln Trp Arg Glu Lys
            20                  25                  30

His Ser Ala Asp Glu Ile Thr Val Arg Asp Leu Ala Ala Asn Pro Ile
        35                  40                  45

Pro Val Leu Asp Gly Glu Leu Val Gly Ala Leu Arg Pro Ser Asp Ala
    50                  55                  60

Pro Leu Thr Pro Arg Gln Gln Glu Ala Leu Ala Leu Ser Asp Glu Leu
65                  70                  75                  80

Ile Ala Glu Leu Lys Ala His Asp Val Ile Val Ala Ala Pro Met
                85                  90                  95

Tyr Asn Phe Asn Ile Ser Thr Gln Leu Lys Asn Tyr Phe Asp Leu Val
                100                 105                 110

Ala Arg Ala Gly Val Thr Phe Arg Tyr Thr Glu Asn Gly Pro Glu Gly
            115                 120                 125

Leu Val Thr Gly Lys Lys Ala Ile Val Ile Thr Ser Arg Gly Gly Ile
    130                 135                 140

His Lys Asp Gly Pro Thr Asp Leu Val Thr Pro Tyr Leu Ser Thr Phe
145                 150                 155                 160

Leu Gly Phe Ile Gly Ile Thr Asp Val Lys Phe Val Phe Ala Glu Gly
                165                 170                 175

Ile Ala Tyr Gly Pro Glu Met Ala Ala Lys Ala Gln Ser Asp Ala Lys
            180                 185                 190

Ala Ala Ile Asp Ser Ile Val Ser Ala
        195                 200
```

<210> SEQ ID NO 8
<211> LENGTH: 217
<212> TYPE: PRT
<213> ORGANISM: Artificial Sequence
<220> FEATURE:
<223> OTHER INFORMATION: NR-36 (NCBI RefSeq: WP_000351487.1)

<400> SEQUENCE: 8

```
Met Asp Ile Ile Ser Val Ala Leu Lys Arg His Ser Thr Lys Ala Phe
1               5                   10                  15

Asp Ala Ser Lys Lys Leu Thr Pro Glu Gln Ala Glu Gln Ile Lys Thr
            20                  25                  30

Leu Leu Gln Tyr Ser Pro Ser Ser Thr Asn Ser Gln Pro Trp His Phe
        35                  40                  45

Ile Val Ala Ser Thr Glu Glu Gly Lys Ala Arg Val Ala Lys Ser Ala
    50                  55                  60

Ala Gly Asn Tyr Val Phe Asn Glu Arg Lys Met Leu Asp Ala Ser His
65                  70                  75                  80

Val Val Val Phe Cys Ala Lys Thr Ala Met Asp Asp Val Trp Leu Lys
                85                  90                  95
```

```
Leu Val Val Asp Gln Glu Asp Ala Asp Gly Arg Phe Ala Thr Pro Glu
            100                 105                 110

Ala Lys Ala Ala Asn Asp Lys Gly Arg Lys Phe Phe Ala Asp Met His
        115                 120                 125

Arg Lys Asp Leu His Asp Ala Glu Trp Met Ala Lys Gln Val Tyr
    130                 135                 140

Leu Asn Val Gly Asn Phe Leu Leu Gly Val Ala Ala Leu Gly Leu Asp
145                 150                 155                 160

Ala Val Pro Ile Glu Gly Phe Asp Ala Ala Ile Leu Asp Ala Glu Phe
                165                 170                 175

Gly Leu Lys Glu Lys Gly Tyr Thr Ser Leu Val Val Pro Val Gly
            180                 185                 190

His His Ser Val Glu Asp Phe Asn Ala Thr Leu Pro Lys Ser Arg Leu
            195                 200                 205

Pro Gln Asn Ile Thr Leu Thr Glu Val
            210                 215

<210> SEQ ID NO 9
<211> LENGTH: 245
<212> TYPE: PRT
<213> ORGANISM: Artificial Sequence
<220> FEATURE:
<223> OTHER INFORMATION: NR-I-A5

<400> SEQUENCE: 9

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Ile Asn Gly Gln Gln Val Thr Val
        35                  40                  45

Ile Thr Val Gln Asp Glu Glu Arg Lys Lys Lys Ile Ala Glu Leu Ala
    50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Glu Ser Met Gly
        115                 120                 125

Leu Gly Thr Val Pro Ile Gly Ala Val Arg Gly Arg Ala Glu Glu Leu
    130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
        195                 200                 205

Thr Asn Gly Gln Glu Thr Arg Asn Trp Ser Gln Gly Ile Ser Ala Tyr
    210                 215                 220

Tyr Asn Lys Val Tyr Glu Pro His Ile Arg Glu Met Leu Glu Lys Gln
225                 230                 235                 240
```

```
Gly Phe Lys Leu Glu
            245

<210> SEQ ID NO 10
<211> LENGTH: 245
<212> TYPE: PRT
<213> ORGANISM: Artificial Sequence
<220> FEATURE:
<223> OTHER INFORMATION: NR-I-A11

<400> SEQUENCE: 10

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Thr Asn Gly Gln Gln Val Thr Val
        35                  40                  45

Ile Thr Val Gln Asp Glu Glu Arg Lys Lys Lys Ile Ala Glu Leu Ala
    50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Glu Ser Met Gly
        115                 120                 125

Leu Gly Thr Val Pro Ile Gly Ala Val Arg Gly Arg Ala Glu Glu Leu
    130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
        195                 200                 205

Thr Asn Gly Gln Glu Thr Arg Asn Trp Ser Gln Gly Ile Ser Ala Tyr
    210                 215                 220

Tyr Asn Lys Val Tyr Tyr Pro His Ile Arg Glu Met Leu Glu Lys Gln
225                 230                 235                 240

Gly Phe Lys Leu Glu
            245

<210> SEQ ID NO 11
<211> LENGTH: 245
<212> TYPE: PRT
<213> ORGANISM: Artificial Sequence
<220> FEATURE:
<223> OTHER INFORMATION: NR-I-A12

<400> SEQUENCE: 11

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Ile Asn Gly Gln Gln Val Thr Val
        35                  40                  45
```

```
Ile Thr Val Gln Asp Glu Glu Arg Lys Lys Lys Ile Ala Glu Leu Ala
        50                  55                  60

Gly Gly Gln Val Trp Ile Glu Gln Ala Pro Val Phe Leu Leu Phe Cys
 65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Glu Ser Met Gly
        115                 120                 125

Leu Gly Thr Val Pro Ile Gly Ala Val Arg Gly Arg Ala Glu Glu Leu
        130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
                180                 185                 190

Leu Ile Asp Ala Tyr Asp Glu Glu Ile Ser Glu Tyr Met Thr Lys Arg
            195                 200                 205

Thr Asn Gly Gln Glu Thr Arg Asn Trp Ser Gln Gly Ile Ser Ala His
        210                 215                 220

Tyr Asn Lys Val Tyr Tyr Pro His Ile Arg Glu Met Leu Glu Lys Gln
225                 230                 235                 240

Gly Phe Lys Leu Glu
                245

<210> SEQ ID NO 12
<211> LENGTH: 245
<212> TYPE: PRT
<213> ORGANISM: Artificial Sequence
<220> FEATURE:
<223> OTHER INFORMATION: NR-I-C3

<400> SEQUENCE: 12

Met Asn Glu Val Leu Lys Thr Leu Lys Asp His Arg Ser Ile Arg Ser
 1               5                  10                  15

Tyr Thr Asp Glu Pro Val Ser Pro Glu Gln Leu Asp Asp Ile Ile Gln
                20                  25                  30

Ala Val Gln Ala Ala Pro Asn Ser Ile Asn Gly Gln Gln Val Thr Val
            35                  40                  45

Ile Thr Val Gln Asp Glu Glu Arg Lys Lys Lys Ile Ala Glu Leu Ala
        50                  55                  60

Gly Gly Gln Val Trp Ile Glu Gln Ala Pro Val Phe Leu Leu Phe Cys
 65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Glu Ser Met Gly
        115                 120                 125

Leu Gly Thr Val Pro Ile Gly Gly Val Arg Gly Arg Ala Glu Glu Leu
        130                 135                 140

Ile Lys Leu Leu Asn Ile Pro Glu Tyr Val Phe Pro Val Ala Gly Leu
145                 150                 155                 160
```

```
Val Val Gly His Pro Ala Asp Arg Ser Ala Lys Lys Pro Arg Leu Pro
            165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
            195                 200                 205

Thr Asn Gly Gln Glu Thr Arg Asn Trp Ser Gln Gly Ile Ser Ala Tyr
210                 215                 220

Tyr Asn Lys Val Asn Tyr Pro His Ile Arg Glu Met Leu Glu Lys Gln
225                 230                 235                 240

Gly Phe Lys Leu Glu
            245

<210> SEQ ID NO 13
<211> LENGTH: 245
<212> TYPE: PRT
<213> ORGANISM: Artificial Sequence
<220> FEATURE:
<223> OTHER INFORMATION: NR-I-D6

<400> SEQUENCE: 13

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Ile Asn Gly Gln Gln Val Thr Val
        35                  40                  45

Ile Thr Val Gln Asp Glu Glu Arg Lys Lys Lys Ile Ala Glu Leu Ala
50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Ala Glu Ser Met Gly
        115                 120                 125

Leu Gly Thr Val Pro Ile Gly Ala Val Arg Gly Arg Ala Glu Glu Leu
        130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
            165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
            195                 200                 205

Thr Asn Gly Gln Glu Thr Arg Asn Trp Ser Gln Gly Ile Ser Ala His
210                 215                 220

Tyr Asn Lys Val Tyr Tyr Pro His Ile Arg Glu Met Leu Glu Lys Gln
225                 230                 235                 240

Gly Phe Lys Leu Glu
            245

<210> SEQ ID NO 14
```

<211> LENGTH: 245
<212> TYPE: PRT
<213> ORGANISM: Artificial Sequence
<220> FEATURE:
<223> OTHER INFORMATION: NR-I-E7

<400> SEQUENCE: 14

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Ile Asn Gly Gln Gln Val Thr Val
        35                  40                  45

Ile Thr Val Gln Asp Glu Glu Arg Lys Lys Lys Ile Ala Glu Leu Ala
50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Glu Ser Met Gly
        115                 120                 125

Leu Gly Thr Val Pro Ile Gly Gly Val Arg Gly Arg Ala Glu Glu Leu
130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
        195                 200                 205

Thr Asn Gly Gln Glu Thr Arg Asn Trp Ser Gln Gly Ile Ser Ala Lys
210                 215                 220

Tyr Asn Lys Val Asn Tyr Pro His Ile Arg Glu Met Leu Glu Lys Gln
225                 230                 235                 240

Gly Phe Lys Leu Glu
            245

<210> SEQ ID NO 15
<211> LENGTH: 245
<212> TYPE: PRT
<213> ORGANISM: Artificial Sequence
<220> FEATURE:
<223> OTHER INFORMATION: NR-I-F5

<400> SEQUENCE: 15

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Val Asn Gly Gln Gln Val Thr Val
        35                  40                  45

Ile Thr Val Gln Asp Glu Glu Arg Lys Lys Lys Ile Ala Glu Leu Ala
50                  55                  60

Gly Gly Gln Val Trp Ile Glu Gln Ala Pro Val Phe Leu Leu Phe Cys

```
            65                  70                  75                  80
Ala Asp Phe Asn Arg Ala Lys Ile Ala Leu Glu Lys Asn Gly Glu Thr
                    85                  90                  95

Leu Ala Ile Thr Asp Gly Met Glu Ser Val Leu Val Gly Ala Val Asp
                100                 105                 110

Ala Gly Ile Ala Leu Gly Thr Ala Thr Ala Ala Glu Ser Met Gly
                115                 120                 125

Leu Gly Thr Val Pro Ile Gly Gly Val Arg Gly Arg Ala Glu Glu Leu
            130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
            195                 200                 205

Thr Asn Gly Gln Glu Thr Arg Asn Trp Ser Gly Gly Ile Ser Ala Tyr
210                 215                 220

Tyr Asn Lys Val Arg Lys Pro His Ile Arg Glu Met Leu Glu Lys Gln
225                 230                 235                 240

Gly Phe Lys Leu Glu
                245

<210> SEQ ID NO 16
<211> LENGTH: 245
<212> TYPE: PRT
<213> ORGANISM: Artificial Sequence
<220> FEATURE:
<223> OTHER INFORMATION: NR-I-H5

<400> SEQUENCE: 16

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
                20                  25                  30

Ala Val Gln Ala Ala Pro Asn Ser His Asn Gly Gln Gln Val Thr Val
            35                  40                  45

Ile Thr Val Gln Asp Glu Glu Arg Lys L

```
                    180                 185                 190
Leu Ile Asp Ala Tyr Asp Glu Glu Ile Ser Glu Tyr Met Thr Lys Arg
            195                 200                 205

Thr Asn Gly Gln Glu Thr Arg Asn Trp Ser Gln Gly Ile Ser Ala Phe
        210                 215                 220

Tyr Asn Lys Val Lys Lys Pro His Ile Arg Glu Met Leu Glu Lys Gln
225                 230                 235                 240

Gly Phe Lys Leu Glu
                245

<210> SEQ ID NO 17
<211> LENGTH: 245
<212> TYPE: PRT
<213> ORGANISM: Artificial Sequence
<220> FEATURE:
<223> OTHER INFORMATION: NR-II-A1

<400> SEQUENCE: 17

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Ser Asn Gly Gln Gln Val Thr Val
        35                  40                  45

Ile Thr Val Gln Asp Glu Glu Arg Lys Lys Lys Ile Ala Glu Leu Ala
    50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Ala Glu Ser Met Gly
        115                 120                 125

Leu Gly Thr Val Pro Ile Gly Gly Val Arg Gly Arg Ala Glu Glu Leu
    130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Gly Thr Tyr Gln Pro Asp Leu Lys Pro
            180                 185                 190

Leu Ile Asp Ala Tyr Asp Glu Glu Ile Ser Glu Tyr Met Thr Lys Arg
        195                 200                 205

Thr Asn Gly Gln Glu Thr Arg Asn Trp Ser Gln Gly Ile Ser Ala Lys
    210                 215                 220

Tyr Asn Lys Val Gln Lys Pro His Ile Arg Glu Met Leu Glu Lys Gln
225                 230                 235                 240

Gly Phe Lys Leu Glu
                245

<210> SEQ ID NO 18
<211> LENGTH: 245
<212> TYPE: PRT
<213> ORGANISM: Artificial Sequence
<220> FEATURE:
<223> OTHER INFORMATION: NR-II-B10
```

<400> SEQUENCE: 18

```
Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Val Asn Gly Gln Gln Val Thr Val
        35                  40                  45

Ile Thr Val Gln Asp Glu Glu Arg Lys Lys Lys Ile Ala Glu Leu Ala
50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Ala Glu Ser Met Gly
        115                 120                 125

Leu Gly Thr Val Pro Ile Gly Gly Val Arg Gly Arg Ala Glu Glu Leu
130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
        195                 200                 205

Thr Asn Gly Gln Glu Thr Arg Asn Trp Ser Gln Gly Ile Ser Ala Met
210                 215                 220

Tyr Asn Lys Val Asn Lys Pro His Ile Arg Glu Met Leu Glu Lys Gln
225                 230                 235                 240

Gly Phe Lys Leu Glu
                245
```

<210> SEQ ID NO 19
<211> LENGTH: 245
<212> TYPE: PRT
<213> ORGANISM: Artificial Sequence
<220> FEATURE:
<223> OTHER INFORMATION: NR-II-D4

<400> SEQUENCE: 19

```
Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser Val Asn Gly Gln Gln Val Thr Val
        35                  40                  45

Ile Thr Val Gln Asp Glu Glu Arg Lys Lys Lys Ile Ala Glu Leu Ala
50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95
```

Leu Ala Ile Thr Asp Gly Met Glu Ser Val Leu Val Gly Ala Val Asp
                100                 105                 110

Ala Gly Ile Ala Leu Gly Thr Ala Thr Ala Ala Glu Ser Met Gly
            115                 120                 125

Leu Gly Thr Val Pro Ile Gly Gly Val Arg Gly Arg Ala Glu Glu Leu
        130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
        195                 200                 205

Thr Asn Gly Gln Glu Thr Arg Asn Trp Ser Gln Gly Ile Ser Ala Lys
        210                 215                 220

Tyr Asn Lys Val Tyr Phe Pro His Ile Arg Glu Met Leu Glu Lys Gln
225                 230                 235                 240

Gly Phe Lys Leu Glu
            245

<210> SEQ ID NO 20
<211> LENGTH: 245
<212> TYPE: PRT
<213> ORGANISM: Artificial Sequence
<220> FEATURE:
<223> OTHER INFORMATION: NR-II-D11

<400> SEQUENCE: 20

Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
            20                  25                  30

Ala Val Gln Ala Ala Pro Asn Ser His Asn Gly Gln Gln Val Thr Val
        35                  40                  45

Ile Thr Val Gln Asp Glu Glu Arg Lys Lys Lys Ile Ala Glu Leu Ala
    50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Glu Ser Met Gly
        115                 120                 125

Leu Gly Thr Val Pro Ile Gly Gly Val Arg Gly Arg Ala Glu Glu Leu
    130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
        195                 200                 205

```
Thr Asn Gly Gln Glu Thr Arg Asn Trp Ser Gln Gly Ile Ser Ala Tyr
    210                 215                 220

Tyr Asn Lys Val Lys Tyr Pro His Ile Arg Glu Met Leu Glu Lys Gln
225                 230                 235                 240

Gly Phe Lys Leu Glu
                245
```

<210> SEQ ID NO 21
<211> LENGTH: 245
<212> TYPE: PRT
<213> ORGANISM: Artificial Sequence
<220> FEATURE:
<223> OTHER INFORMATION: NR-II-D12

<400> SEQUENCE: 21

```
Met Asn Glu Val Leu Lys Thr Leu Lys Asp His Arg Ser Ile Arg Ser
1               5                   10                  15

Tyr Thr Asp Glu Pro Val Ser Pro Glu Gln Leu Asp Asp Ile Ile Gln
                20                  25                  30

Ala Val Gln Ala Ala Pro Asn Ser Ser Asn Gly Gln Gln Val Thr Val
            35                  40                  45

Ile Thr Val Gln Asp Glu Glu Arg Lys Lys Lys Ile Ala Glu Leu Ala
50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
                100                 105                 110

Ala Gly Ile Ala Leu Gly Thr Ala Thr Ala Ala Ala Glu Ser Met Gly
            115                 120                 125

Leu Gly Thr Val Pro Ile Gly Gly Val Arg Gly Arg Ala Glu Glu Leu
130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Glu Tyr Met Thr Lys Arg
195                 200                 205

Thr Asn Gly Gln Glu Thr Arg Asn Trp Ser Gln Gly Ile Ser Ala Phe
210                 215                 220

Tyr Asn Lys Val Lys Phe Pro His Ile Arg Glu Met Leu Glu Lys Gln
225                 230                 235                 240

Gly Phe Lys Leu Glu
                245
```

<210> SEQ ID NO 22
<211> LENGTH: 245
<212> TYPE: PRT
<213> ORGANISM: Artificial Sequence
<220> FEATURE:
<223> OTHER INFORMATION: NR-II-E1

<400> SEQUENCE: 22

```
Met Asn Glu Val Leu Lys Thr Leu Lys Asp His Arg Ser Ile Arg Ser
1               5                   10                  15
```

Tyr Thr Asp Glu Pro Val Ser Pro Glu Gln Leu Asp Asp Ile Ile Gln
                20                  25                  30

Ala Val Gln Ala Ala Pro Asn Ser Ser Asn Gly Gln Gln Val Thr Val
            35                  40                  45

Ile Thr Val Gln Asp Glu Glu Arg Lys Lys Lys Ile Ala Glu Leu Ala
        50                  55                  60

Gly Gly Gln Val Trp Ile Glu Gln Ala Pro Val Phe Leu Leu Phe Cys
65                  70                  75                  80

Ala Asp Phe Asn Arg Ala Lys Ile Ala Leu Glu Lys Asn Gly Glu Thr
                85                  90                  95

Leu Ala Ile Thr Asp Gly Met Glu Ser Val Leu Val Gly Ala Val Asp
            100                 105                 110

Ala Gly Ile Ala Leu Gly Thr Ala Thr Ala Ala Glu Ser Met Gly
        115                 120                 125

Leu Gly Thr Val Pro Ile Gly Gly Val Arg Gly Arg Ala Glu Glu Leu
130                 135                 140

Ile Lys Leu Leu Asn Ile Pro Glu Tyr Val Phe Pro Val Ala Gly Leu
145                 150                 155                 160

Val Val Gly His Pro Ala Asp Arg Ser Ala Lys Lys Pro Arg Leu Pro
                165                 170                 175

Glu Gln Ala Val Arg His Ser Glu Thr Tyr Gln Pro Asp Leu Lys Pro
            180                 185                 190

Leu Ile Asp Ala Tyr Asp Glu Glu Ile Ser Gly Tyr Met Thr Lys Arg
        195                 200                 205

Thr Asn Gly Gln Glu Thr Arg Asn Trp Ser Gln Gly Ile Ser Ala Tyr
210                 215                 220

Tyr Asn Lys Val Lys Tyr Pro His Ile Arg Glu Met Leu Glu Lys Gln
225                 230                 235                 240

Gly Phe Lys Leu Glu
                245

<210> SEQ ID NO 23
<211> LENGTH: 376
<212> TYPE: PRT
<213> ORGANISM: Artificial Sequence
<220> FEATURE:
<223> OTHER INFORMATION: ENE-101

<400> SEQUENCE: 23

Met Ser His Thr Leu Phe Asp Pro Val Gln Ala Gly Asp Leu Gln Leu
1               5                   10                  15

Ala Asn Arg Ile Ala Met Ala Pro Leu Thr Arg Asn Arg Ser Pro Asn
                20                  25                  30

Ala Val Pro Lys Asp Ile Thr Ala Thr Tyr Tyr Ala Gln Arg Ala Thr
            35                  40                  45

Ala Gly Leu Leu Ile Thr Glu Ala Thr Ala Ile Ser His Gln Gly Gln
        50                  55                  60

Gly Tyr Ala Asp Val Pro Gly Leu Tyr Ser Thr Glu Gln Leu Asp Gly
65                  70                  75                  80

Trp Lys Lys Val Thr Ala Ala Val His Glu Arg Gly Gly Arg Ile Val
                85                  90                  95

```
Thr Gln Leu Trp His Val Gly Arg Ile Ser His Asn Asp Leu Gln Pro
            100                 105                 110

Asp Gly Gly Ala Pro Val Ala Pro Ser Ala Ile Ala Ala Lys Ser Lys
            115                 120                 125

Thr Tyr Leu Ile Asp Lys Ala Thr Gly Gln Gly His Phe Ala Ala Thr
            130                 135                 140

Ser Glu Pro Arg Ala Leu Asp Ala Glu Glu Leu Pro Gly Ile Val His
145                 150                 155                 160

Asp Tyr Ala Ala Ala Arg Asn Ala Val Glu Thr Ala Gly Phe Asp
                165                 170                 175

Gly Val Glu Ile His Gly Ala Asn Gly Tyr Leu Leu Asp Gln Phe Leu
            180                 185                 190

Lys Thr Gly Ala Asn Arg Arg Thr Asp Asp Tyr Gly Gly Ser Ile Glu
            195                 200                 205

Asn Arg Ala Arg Leu Leu Leu Glu Ala Thr Arg Ala Val Val Asp Ala
        210                 215                 220

Ile Gly Gly Gly Lys Val Gly Ile Arg Leu Ser Pro Val Thr Pro Ala
225                 230                 235                 240

Asn Asp Ile Val Asp Ala Asp Pro Gln Pro Leu Phe Asp Tyr Val Ile
                245                 250                 255

Arg Gln Leu Ala Pro Leu Gly Leu Ala Tyr Val His Val Ile Glu Gly
            260                 265                 270

Ser Thr Gly Gly Pro Arg Glu Leu Glu Asp Arg Pro Phe Asp Tyr Glu
        275                 280                 285

Ala Leu Lys Thr Ala Tyr Arg Glu Ala Gly Lys Gly Ala Trp Met
290                 295                 300

Val Asn Asn Ala Tyr Asp Arg Ala Leu Ala Met Glu Ala Val Ala Ser
305                 310                 315                 320

Gly Arg Ala Asp Ile Val Ala Phe Gly Lys Ala Phe Ile Ser Asn Pro
                325                 330                 335

Asp Leu Val Glu Arg Leu Arg Gln Asp Ala Pro Leu Asn Pro Trp Asp
            340                 345                 350

Ser Lys Thr Phe Tyr Gly Gly Gly Glu Lys Gly Tyr Thr Asp Tyr Pro
        355                 360                 365

Thr Leu Gly Glu Ser Ala Lys Gly
370                 375
```